(12) United States Patent
Gambacorti-Passerini et al.

(10) Patent No.: US 9,428,500 B2
(45) Date of Patent: Aug. 30, 2016

(54) ALPHA-CARBOLINES FOR THE TREATMENT OF CANCER

(71) Applicants: UNIVERSITA' DEGLI STUDI DI MILANO—BICOCCA, Milan (IT); UNIVERSITÉ DE GENÈVE, Geneva (CH); UNIVERSITÉ CLAUDE BERNARD—LYON 1, Villeurbanne (FR)

(72) Inventors: Carlo Gambacorti-Passerini, Monza (IT); Luca Mologni, Vedano Al Lambro (IT); Leonardo Scapozza, Genève (CH); William Bisson, Genève (CH); Shaheen Ahmed, Genève (CH); Peter Goekjian, Villeurbanne (FR); Sébastien Tardy, Villeurbanne (FR); Alexandre Orsato, Villeurbanne (FR); David Gueyrard, Villeurbanne (FR); Joseph Benoit, Villeurbanne (FR)

(73) Assignees: UNIVERSITA DEGLI STUDI DI MILANO—BICOCCA, Milan (IT); UNIVERSITE DE GENEVE, Geneva (CH); UNIVERSITE CLAUDE BERNARD—LYON, Villeurbanne (FR)

( * ) Notice: Subject to any disclaimer, the term of this patent is extended or adjusted under 35 U.S.C. 154(b) by 0 days.

(21) Appl. No.: 14/399,925

(22) PCT Filed: May 10, 2013

(86) PCT No.: PCT/EP2013/059721
§ 371 (c)(1),
(2) Date: Nov. 7, 2014

(87) PCT Pub. No.: WO2013/167730
PCT Pub. Date: Nov. 14, 2013

(65) Prior Publication Data
US 2015/0105554 A1    Apr. 16, 2015

(30) Foreign Application Priority Data

May 11, 2012 (EP) .................................... 12167755

(51) Int. Cl.
*C07D 471/04* (2006.01)
*A61K 31/44* (2006.01)
*C07F 7/08* (2006.01)

(52) U.S. Cl.
CPC .............. *C07D 471/04* (2013.01); *A61K 31/44* (2013.01); *C07F 7/0812* (2013.01)

(58) Field of Classification Search
CPC ............................ C07D 471/04; A61K 31/437
USPC ...................... 544/361, 126; 514/300; 546/79
See application file for complete search history.

(56) References Cited

U.S. PATENT DOCUMENTS 8,895,744 B2 * 11/2014 Gambacorti Passerini et al. ............................... 546/79

FOREIGN PATENT DOCUMENTS

| EP | 2161271 A1 | 3/2010 |
|----|------------|--------|
| EP | 2161271 * | 10/2010 |
| WO | WO 2006/040451 A2 | 4/2006 |

OTHER PUBLICATIONS

International Search Report of PCT/EP2013/059721 dated Sep. 25, 2013.

* cited by examiner

*Primary Examiner* — Rita Desai
(74) *Attorney, Agent, or Firm* — Arent Fox LLP

(57) ABSTRACT

The present invention relates to inhibitors of the oncogenic protein kinase ALK of formula (I) as herein described and pharmaceutical compositions thereof, as well as to key intermediates towards their synthesis. The compounds of formula (I) are useful in the preparation of a medicament, in particular for the treatment of cancer.

13 Claims, 1 Drawing Sheet

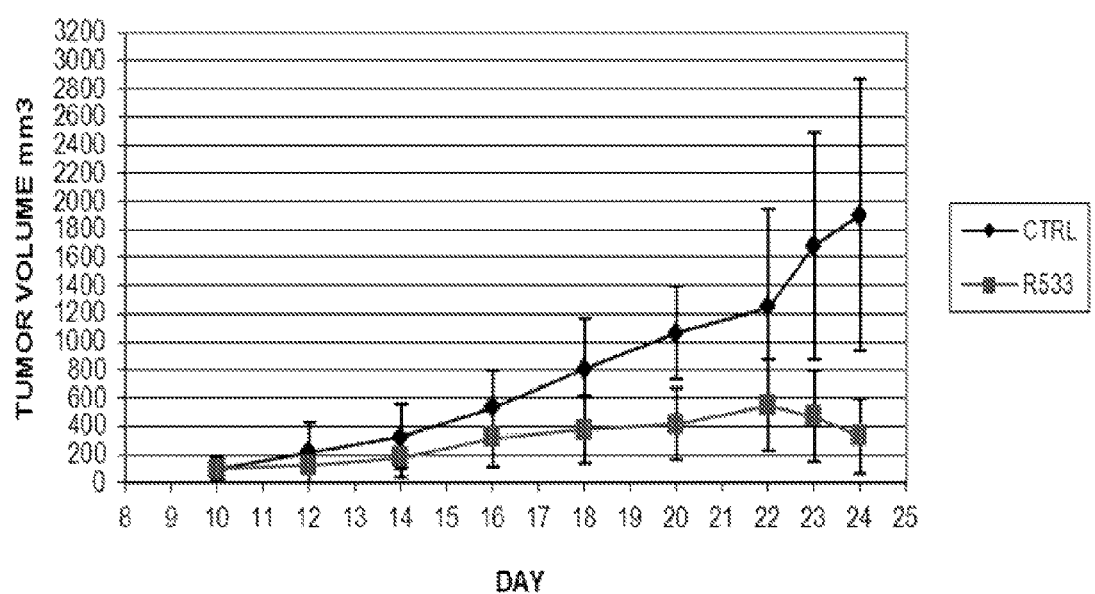

ALPHA-CARBOLINES FOR THE TREATMENT OF CANCER

This application is based upon and claims the benefit of priority of the prior International Application PCT/EP2013/059721, filed on May 10, 2013, and European Patent application 12167755.3, filed on May 11, 2012, the entire contents of which are incorporated herein by reference.

The present invention relates to α-carboline derivatives having ALK kinase inhibitory activity, to their pharmaceutical uses and to key intermediates thereof.

Such inhibitors can be used for the treatment of hyperproliferative diseases such as cancer, in particular for the treatment of ALK fusion protein positive cancers, such as anaplastic large cell lymphoma (ALCL), diffuse large B cell lymphoma, inflammatory myofibroblastic tumours, non-small cell lung cancer (NSCLC), oesophageal squamous cell carcinoma, renal medullary carcinoma, myeloid leukaemia, breast cancer and colorectal carcinoma.

BACKGROUND OF THE INVENTION

Cancer results from the subversion of processes that control the normal growth, location and mortality of cells. This loss of normal control mechanisms arises from the acquisition of mutations that lead to the oncogenic activation of proteins that are involved in the normal regulation of such processes.

Protein kinases are enzymes that catalyse the transfer of phosphate from adenosine-5'-triphosphate (ATP) to specific amino acid residues in many proteins. Generally, the phosphorylation of a protein changes its functionality, from inactive to active in some cases, and from active to inactive in others. Protein kinases are thus involved in the regulation of many aspects of cell function, as most of the signal transduction pathways controlling cell growth, survival, differentiation and motility are mediated by phosphorylation. Abnormal activity of protein kinases has been implicated in many cancers as well as in other diseases. The human genome encodes at least 518 kinases, of which approximately 90 specifically phosphorylate the phenolic hydroxyl of tyrosine residues. Tyrosine kinases are particularly involved in cell proliferation and survival processes, and their aberrant activation most often leads to oncogenic transformation.

For example, structural alterations in ALK produced by the chromosomal rearrangement t(2q23; 5q35) generates the NPM/ALK oncogenic fusion protein associated with ALCL (Rabbitss, T. H. *Nature*, 1994, 372, 143).

Large cell lymphomas represent about 25% of all non-Hodgkin's lymphomas; about one-third of these tumors are anaplastic large cell lymphoma (ALCL). In turn, the majority of ALCL patients (60-80%) possess a chromosomal translocation that leads to the in-frame juxtaposition of the 5' portion of the nucleophosmin (NPM) gene with the sequence encoding for the catalytic domain of ALK kinase. The resulting chimaeric gene, under the control of the strong NPM promoter, drives the expression of the NPM/ALK oncogenic fusion protein. An additional 10% of ALCL patients carry other ALK fusion proteins. To date, 11 ALK fusions have been described. In all cases, the ALK kinase domain sequence is fused to an aminoterminal protein-protein interaction domain of a protein that is highly expressed in the target cell. Thus, the fusion partner provides constitutive expression (through its promoter) and activation (via oligomerisation). In addition, ALK fusion proteins show anomalous cellular localisation. For example, NPM/ALK is mainly found in the cytoplasm and the nucleus. By contrast, wild-type ALK is a tightly regulated, integral membrane protein that is only activated in the presence of a specific extracellular ligand.

About 5-8% of NSCLC patients carry the EML4/ALK fusion. As with NPM/ALK, the 5' fusion partner EML4 provides high expression and constitutive activation of the ALK kinase. The population of ALK+ NSCLC patients, although representing a minority of all NSCLC patients, is estimated to be about 50-70,000 new cases worldwide each year. In addition to fusion proteins, activating point mutants of ALK have been described and validated in familial (90% of cases) and sporadic (~10%) neuroblastoma and in anaplastic thyroid carcinoma (10% of patients).

ALK is normally expressed in the nervous system during embryonic development and is strongly down-regulated at birth, resulting in barely detectable levels in adult tissues. It has been extensively demonstrated that constitutively active NPM/ALK is a potent oncogene with transforming and tumourigenic properties (Morris et al., *Science*, 1994, 263, 1281-1284).

Moreover, rearrangement of ALK kinase is a very early event in tumour formation and is necessary for survival of transformed cells. The high level of expression of NPM/ALK and other ALK fusion protein variants in lymphoma cells and their direct role in lymphomagenesis, combined with the fact that normal ALK is expressed at low levels in the human body, suggests that ALK could potentially be an ideal target for therapy.

There is currently only one drug clinically available for the treatment of ALK-positive cancer. Crizotinib is a dual MET/ALK inhibitor recently approved for ALK+ NSCLC. It potently inhibits ALK phosphorylation and induces apoptosis in ALK+ cancer cells. Initial clinical trials showed excellent activity and tolerability in advanced NSCLC patients (Shaw et al., Lancet Oncol 2011; 12: 1004-12). However, clinical resistance develops in a significant fraction of patients (Choi et al., N Engl J Med 2010; 363: 1734-9). At least half of the patients show either amplification of ALK gene or acquisition of a secondary mutation that renders ALK insensitive to Crizotinib. In particular, the gatekeeper mutant L1196M showed high resistance to Crizotinib. Therefore, there is urgent need for second-generation compounds, with higher potency and selectivity, able to inhibit Crizotinib-resistant mutants and to circumvent clinical resistance. Moreover, it would be desirable to develop compounds which are non-ATP competitive.

EP2161271, in the name of the same applicant, discloses α-carboline derivatives inhibitors of NMP-ALK, RET, and Bcr-Abl.

BRIEF DESCRIPTION OF THE DRAWINGS

FIG. 1: Comparison of tumour growth curves with and without treatment with a compound of this invention in an NPM/ALK+ Karpas299 orthotopic mouse model.

DETAILED DESCRIPTION OF THE INVENTION

In a first aspect of this invention, there is provided compounds of formula (I)

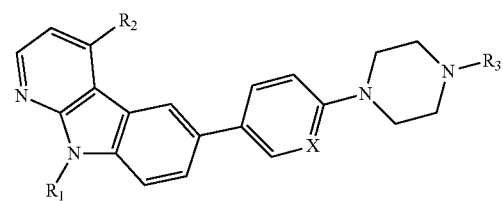

(I)

wherein:
R1 is H or C1-C3 alkyl
R2 is either halogen or

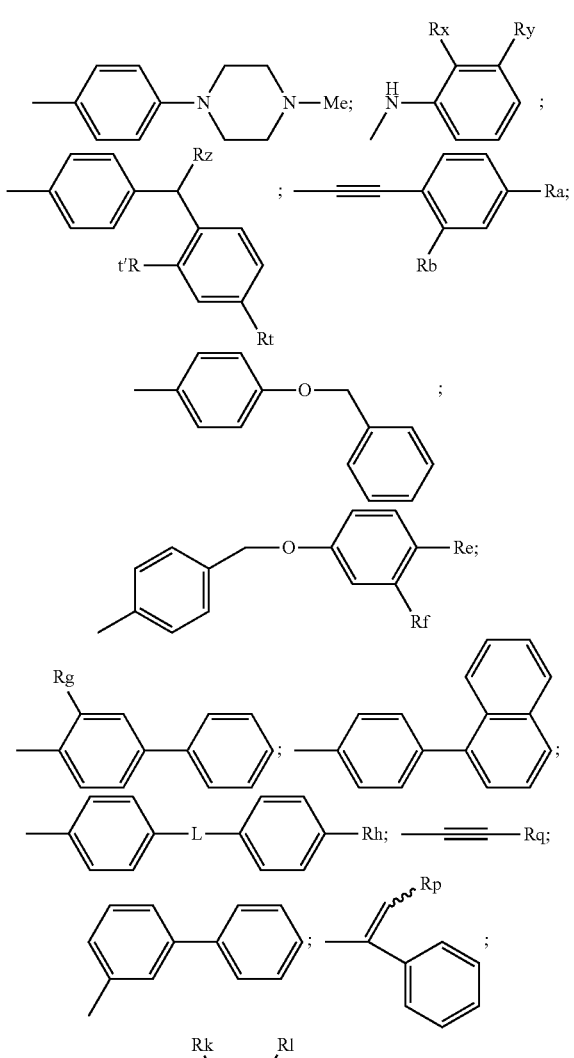

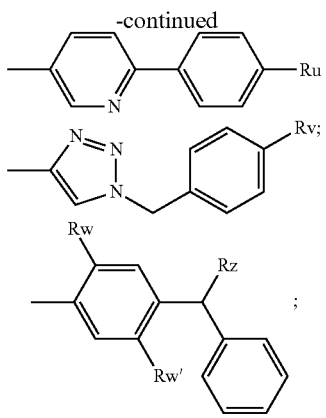

X is either CH or N
R3 is either $C_1$-$C_3$ alkyl or (1-methylpiperidin-4-yl)
Rx and Ry are either H or nitro
Rz and Rz' are H, OH, or oxo
Rt and R't can be the same or different and are H or $C_1$-$C_3$ alkoxy
Ra is H or F
Rb is H, C1-C3 alkoxy, trifluoromethyl, or halogen
Re is H or halogen
Rf is H, C1-C3 alkyl or trifluoromethyl
Rg is H or F
Rk is H, halogen, trifluoromethyl, C1-C3 alkoxy, C1-C3 alkylsulfonamino
Rl is H or F
Rm is H, C1-C3 alkoxy, F or trifluoromethyl
Rn is H, C1-C3 alkyl or a 5- to 6-membered aromatic or heteroaromatic ring
Rp is either C1-C3 alkyl or 5- to 6-membered aromatic or heteroaromatic ring
Rq is either H or tri($C_1$-$C_4$)alkylsilyl
Rs is tri($C_1$-$C_4$)alkylsilyl
Rh is either H, C1-C3 alkoxy or C1-C3 alkylcarbonylamino
Ru is either H or F
Rv is C1-C3 alkyl
Rw and Rw' can be the same or different and are hydroxyl or C1-C3 alkoxy
L and L' are O, S, SO or $SO_2$;
Z is either C or N
In one embodiment (embodiment A1), there is provided compounds of formula I wherein
R1 is H or methyl
R2 is Cl or

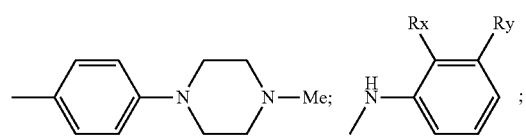

-continued

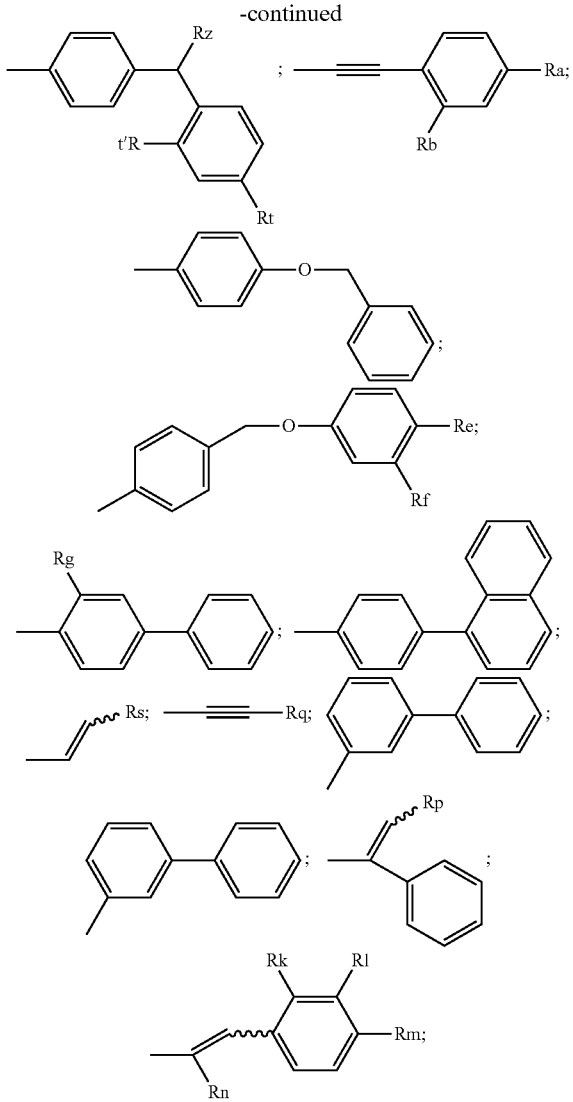

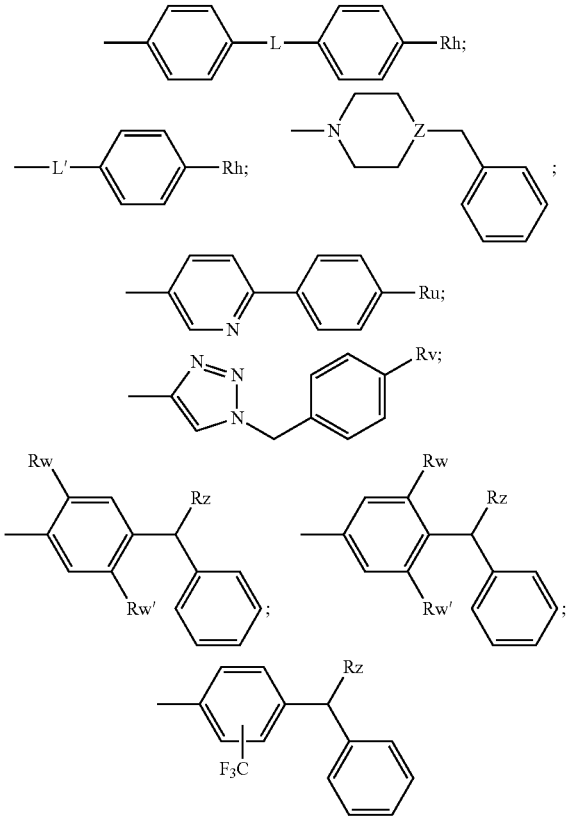

X is either CH or N
R3 is either methyl or 1-methylpiperidin-4-yl
Rx and Ry are either H or nitro
Rz is H, OH or oxo
Rt and R't can be the same or different and can be H or methoxy
Ra is H or F
Rb is H, methoxy, trifluoromethyl, F or Cl
Re is H or Cl
Rf is H, methyl or trifluoromethyl
Rg is H or F
Rk is H, Cl, F, trifluoromethyl, methoxy, methylsulfonamino
Rl is H or F
Rm is H, methoxy, F or trifluoromethyl
Rn is H, methyl, ethyl or phenyl
Rp is ethyl or phenyl
Rq either H or triisopropylsilyl
Rs is triisopropylsilyl.

In another embodiment (Embodiment A2) there is provided compounds of formula (I) wherein
R1 is H or methyl
R2 is Cl or Rz' is H
Ru is F
Rv is methyl
Rw and Rw' are either hydroxyl and methoxy, respectively or both are methoxy
Z is either C or N
L is O and Rh is H
L' is S and Rh is methoxy In another embodiment (Embodiment A3) there are provided compounds of embodiments A1 and A2.

In another embodiment (embodiment B1), there is provided compounds of formula I wherein
R1 is H
R2 is

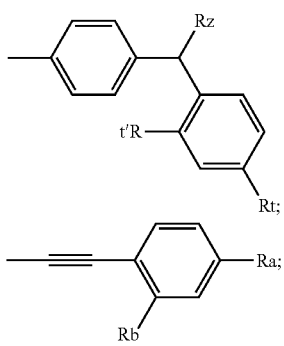

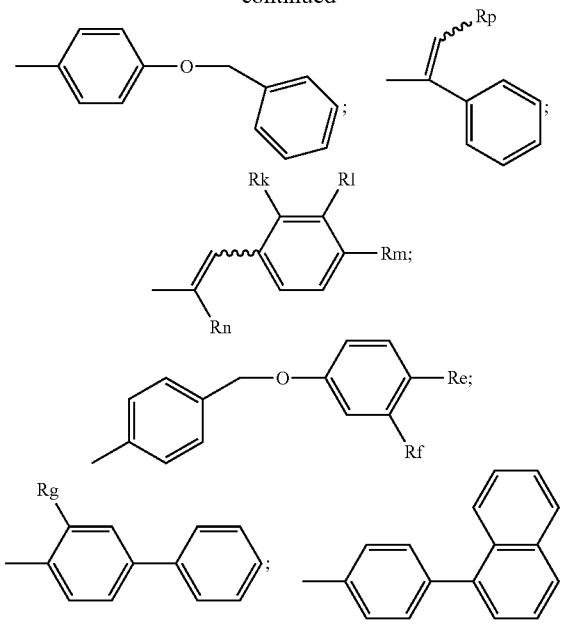

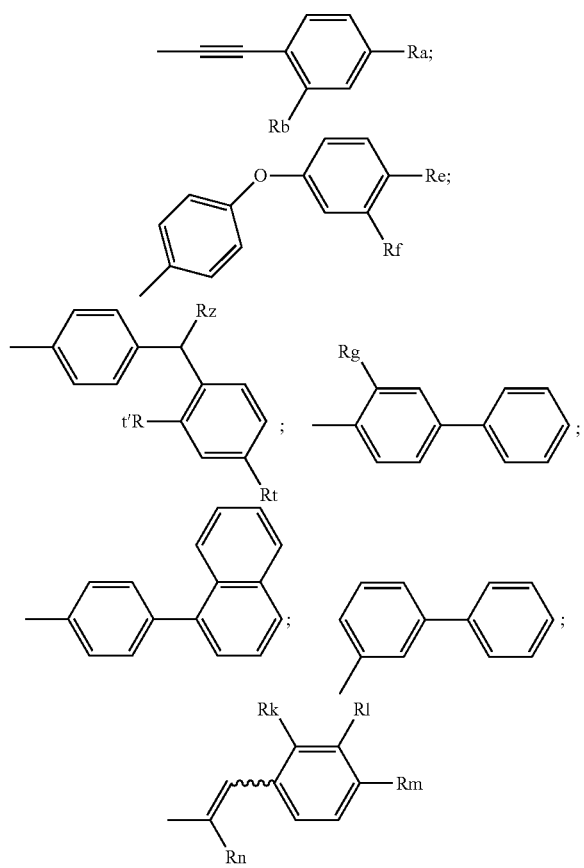

X is CH and R3, Ra, Rb, Re, Rf, Rg, Rk, Rl, Rm, Rn, Rz, Rt, R't and Rp are as defined under formula (I) or embodiment A1.

In another embodiment (embodiment B2), there is provided compounds of formula I wherein R2 is selected from and R1, R3, X, Ra, Rb, Re, Rf, Rg, Rk, Rl, Rm, Rn, Rz, Rt and R't are as defined under formula (I) or embodiment A1.

In another embodiment (embodiment B3), there is provided compounds of formula (I) wherein R2 is selected from

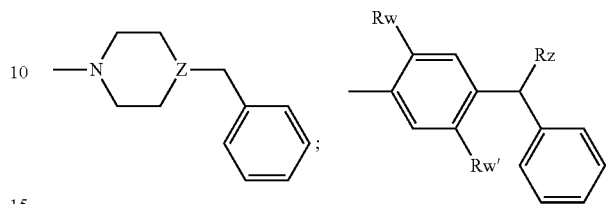

and wherein Z, Rw, Rw' and Rz are defined under formula (I) or embodiment A2 or embodiment A3.

In another embodiment (Embodiment B4), there is provided compounds of embodiments B2 and B3.

In a particular aspect (embodiment C1) of formula (I), embodiment A1 or embodiment B1, or embodiment B2, embodiment B4, when R2 is

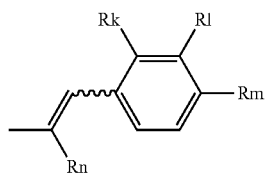

then two of Rk, Rl and Rm are H while the third is as defined under formula (I), embodiment A1, embodiment B1, embodiment B2, or embodiment B4.

In a particular aspect of embodiment C1 (embodiment C2), Rn is H.

In a particular aspect of embodiments B1, B2, B4, C1 or C2 (embodiment D), R2 is

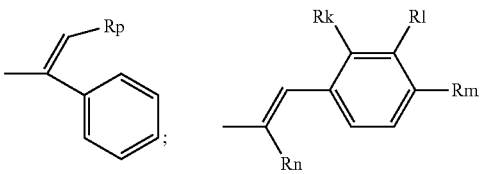

and Rk, Rl, Rm, Rn and Rp are as defined under embodiments B1, B2, B4, C1 or C2.

In a particular aspect R3 is methyl and R1, R2, X, L, L', Z, Rx, Ry, Ra, Rb, Re, Rf, Rg, Rh, Rk, Rl, Rm, Rn, Rp, Rq, Rs, Rz, Rz' Rt, R't, Ru, Rv, Rw and Rw' are as defined in under formula (I), embodiment A1, embodiment A2, embodiment B1, embodiment B2, embodiment B3, embodiment B4, embodiment C1, embodiment C2, or embodiment D.

In another particular aspect, R3 is (1-methylpiperidin-4yl) and R1, R2, X, L, L', Z, Rx, Ry, Ra, Rb, Re, Rf, Rg, Rh, Rk, Rl, Rm, Rn, Rp, Rq, Rs, Rz, Rz' Rt, R't, Ru, Rv, Rw and Rw' are as defined under formula (I), embodiment A1, embodiment A2 embodiment B1, embodiment B2, embodiment B3, embodiment B4 embodiment C1, embodiment C2 or embodiment D.

In another embodiment (Embodiment GO, there is provided a compound selected from the list of:
- (E)-6-[4-(4-Methylpiperazin-1-yl)phenyl]-4-(2-phenylvinyl)-9H-pyrido[2,3-b]indole (R500a);
- (E)-6-[6-(4-Methylpiperazin-1-yl)-pyridin-3-yl]-4-(2-phenylvinyl)-9H-pyrido[2,3-b]indole (R505);
- 4-Biphenyl-4-yl-6-[4-(4-methylpiperazin-1-yl)phenyl]-9H-pyrido[2,3-b]indole (R510a);
- (E)-4-[2-(3-Fluorophenyl)vinyl]-6-[4-(4-methylpiperazin-1-yl)phenyl]-9H-pyrido[2,3-b]indole (R511);
- (E)-4-[2-(4-Methoxyphenyl)vinyl]-6-[4-(4-methylpiperazin-1-yl)phenyl]-9H-pyrido[2,3-b]indole (R517);
- 4-(4-Benzyloxyphenyl)-6-[4-(4-methylpiperazin-1-yl)phenyl]-9H-pyrido[2,3-b]indole (R518);
- 6-[4-(4-Methylpiperazin-1-yl)phenyl]-4-[4-(3-(trifluoromethyl)-phenoxymethyl)phenyl]-9H-pyrido[2,3-b]indole (R519);
- (E)-4-(2-(2-Methoxyphenyl)vinyl))-6-(4-(4-methylpiperazin-1-yl)phenyl)-9H-pyrido[2,3-b]indole (R520);
- (E)-6-(4-(4-Methylpiperazin-1-yl)phenyl)-4-(2-(2-(trifluoromethyl)phenyl)vinyl)-9H-pyrido[2,3-b]indole (R521);
- 4-[4-(4-Chloro-3-methyl-phenoxymethyl)phenyl]-6-[4-(4-methylpiperazin-1-yl)phenyl]-9H-pyrido[2,3-b]indole (R522);
- 6-[4-(4-Methylpiperazin-1-yl)phenyl]-4-phenylethynyl-9H-pyrido[2,3-b]indole (R523);
- (E)-4-(2-(4-Fluorophenyl)vinyl))-6-(4-(4-methylpiperazin-1-yl)phenyl)-9H-pyrido[2,3-b]indole (R527);
- (E)-6-(4-(4-Methylpiperazin-1-yl)phenyl)-4-(2-(4-(trifluoromethyl)phenyl)vinyl))-9H-pyrido[2,3-b]indole (R528);
- 4-(3-Fluorobiphenyl-4-yl)-6-[4-(4-methylpiperazin-1-yl)phenyl]-9H-pyrido[2,3-b]indole (R532);
- 4-(4-Benzylphenyl)-6-[4-(4-methylpiperazin-1-yl)phenyl]-9H-pyrido[2,3-b]indole (R533);
- 4-Biphenyl-3-yl-6-[4-(4-methylpiperazin-1-yl)phenyl]-9H-pyrido[2,3-b]indole (R534);
- 4-((2-Methoxyphenyl)ethynyl)-6-[4-(4-methylpiperazin-1-yl)phenyl]-9H-pyrido[2,3-b]indole (R538);
- 6-[4-(4-Methylpiperazin-1-yl)phenyl]-4-((2-(trifluoromethyl)phenyl)ethynyl)-9H-pyrido[2,3-b]indole (R539);
- 4-((4-Fluorophenyl)ethynyl)-6-[4-(4-methylpiperazin-1-yl)phenyl]-9H-pyrido[2,3-b]indole (R540);
- 4-((2-Fluorophenyl)ethynyl)-6-[4-(4-methylpiperazin-1-yl)phenyl]-9H-pyrido[2,3-b]indole (R541);
- (E)-4-(2-(2-Fluorophenyl)vinyl))-6-(4-(4-methylpiperazin-1-yl)phenyl)-9H-pyrido[2,3-b]indole (R542);
- (E)-4-(2-(2-Chlorophenyl)vinyl))-6-(4-(4-methylpiperazin-1-yl)phenyl)-9H-pyrido[2,3-b]indole (R543);
- 6-(4-(4-Methylpiperazin-1-yl)phenyl)-N-(3-nitrophenyl)-9H-pyrido[2,3-b]indol-4-amine(R547);
- 6-(4-(4-Methylpiperazin-1-yl)phenyl)-N-(2-nitrophenyl)-9H-pyrido[2,3-b]indol-4-amine (R548);
- 4-((2-Chlorophenyl)ethynyl)-6-[4-(4-methylpiperazin-1-yl)phenyl]-9H-pyrido[2,3-b]indole (R549);
- 4-((2-Methoxyphenyl)ethynyl)-9-methyl-6-[4-(4-methylpiperazin-1-yl)phenyl]-9H-pyrido[2,3-b]indole (R555);
- 4,6-Bis-[4-(4-methylpiperazin-1-yl)phenyl]-9H-pyrido[2,3-b]indole (R556);
- 4-(4-Benzylphenyl)-6-(4-(4-(1-methylpiperidin-4-yl)piperazin-1-yl)phenyl)-9H-pyrido[2,3-b]indole (R559);
- (E)-6-(4-(4-(1-Methylpiperidin-4-yl)piperazin-1-yl)phenyl)-4-(2-(2-(trifluoromethyl)phenyl)vinyl))-9H-pyrido[2,3-b]indole (R566);
- 6-(4-(4-(1-methylpiperidin-4-yl)piperazin-1-yl)phenyl)-N-(2-nitrophenyl)-9H-pyrido[2,3-b]indol-4-amine (R567);
- (E)-6-(4-(4-Methylpiperazin-1-yl)phenyl)-4-(1-phenylprop-1-en-2-yl)-9H-pyrido[2,3-b]indole (R569);
- (4-{6-[4-(4-Methylpiperazin-1-yl)phenyl]-9H-pyrido[2,3-b]indol-4-yl}-phenyl)phenyl-methanol (R570);
- (4-{6-[4-(4-Methylpiperazin-1-yl)phenyl]-9H-pyrido[2,3-b]indol-4-yl}-phenyl)phenyl-methanone (R571);
- 4-Chloro-6-[4-(4-methylpiperazin-1-yl)phenyl]-9H-pyrido[2,3-b]indole (R588);
- (E)-N-[2-(2-{6-[4-(4-Methylpiperazin-1-yl)phenyl]-9H-pyrido[2,3-b]indol-4-yl}-vinyl)phenyl]-methanesulfonamide (R589);
- 6-[4-(4-Methylpiperazin-1-yl)phenyl]-4-(4-naphthalen-1-yl-phenyl)-9H-pyrido[2,3-b]indole (R590);
- (E)-4-(1,2-Diphenylvinyl)-6-[4-(4-methylpiperazin-1-yl)phenyl]-9H-pyrido[2,3-b]indole (R593);
- (E)-6-[4-(4-Methylpiperazin-1-yl)phenyl]-4-(1-phenyl-but-1-enyl)-9H-pyrido[2,3-b]indole (R594);
- (E)-6-(4-(4-Methylpiperazin-1-yl)phenyl)-4-(1-phenylbut-1-en-2-yl)-9H-pyrido[2,3-b]indole;
- 4-[4-(2,4-Dimethoxybenzyl)phenyl]-6-[4-(4-methylpiperazin-1-yl)phenyl]-9H-pyrido[2,3-b]indole (R596);
- (E)-4-[1-(2-Methoxyphenyl)-prop-1-en-2-yl]-6-[4-(4-methylpiperazin-1-yl)phenyl]-9H-pyrido[2,3-b]indole (R604);
- (E)-6-[4-(4-Methylpiperazin-1-yl)-phenyl]-4-[1-(2-(trifluoromethyl)phenyl)-prop-1-en-2-yl]-9H-pyrido[2,3-b]indole (R605);
- 6-(4-(4-methylpiperazin-1-yl)phenyl)-4-((triisopropylsilyl)ethynyl)-9H-pyrido[2,3-b]indole (R606);
- (E) and/or (Z)-6-(4-(4-methylpiperazin-1-yl)phenyl)-4-(2-(triisopropylsilyl)vinyl)-9H-pyrido[2,3-b]indole R(607) and
- 4-ethynyl-6-(4-(4-methylpiperazin-1-yl)phenyl)-9H-pyrido[2,3-b]indole R(608).

In yet another embodiment (Embodiment G2), there is provided a compound selected from the list of:
- 4-(4-Methoxy-phenylsulfanyl)-6-[4-(4-methyl-piperazin-1-yl)-phenyl]-9H-pyrido[2,3-b]indole (R619);
- 4-(1-(4-methylbenzyl)-1H-1,2,3-triazol-4-yl)-6-(4-(4-methylpiperazin-1-yl)phenyl)-9H-pyrido[2,3-b]indole (R620);
- 6-(4-(4-methylpiperazin-1-yl)phenyl)-4-(4-phenoxyphenyl)-9H-pyrido[2,3-b]indole (R621);
- 4-(6-(4-fluorophenyl)pyridin-3-yl)-6-(4-(4-methylpiperazin-1-yl)phenyl)-9H-pyrido[2,3-b]indole (R650);
- (2,5-dimethoxy-4-(6-(4-(4-methylpiperazin-1-yl)phenyl)-9H-pyrido[2,3-b]indol-4-yl)phenyl)(phenyl)methanone (R654);
- (2-hydroxy-5-methoxy-4-(6-(4-(4-methylpiperazin-1-yl)phenyl)-9H-pyrido[2,3-b]indol-4-yl)phenyl)(phenyl)methanone (R656);
- 4-(4-benzyl-2,5-dimethoxyphenyl)-6-(4-(4-methylpiperazin-1-yl)phenyl)-9H-pyrido[2,3-b]indole (R666);
- 2-benzyl-4-methoxy-5-(6-(4-(4-methylpiperazin-1-yl)phenyl)-9H-pyrido[2,3-b]indol-4-yl)phenol (R667);
- 4-(4-benzyl-3-(trifluoromethyl)phenyl)-6-(4-(4-methylpiperazin-1-yl)phenyl)-9H-pyrido[2,3-b]indole (R686);
- 4-(4-benzyl-2-(trifluoromethyl)phenyl)-6-(4-(4-methylpiperazin-1-yl)phenyl)-9H-pyrido[2,3-b]indole (R687);
- 4-(4-benzyl-3,5-dimethoxyphenyl)-6-(4-(4-methylpiperazin-1-yl)phenyl)-9H-pyrido[2,3-b]indole (R696);
- (2,5-dimethoxy-4-(6-(4-(4-methylpiperazin-1-yl)phenyl)-9H-pyrido[2,3-b]indol-4-yl)phenyl)(phenyl)methanol (R655);
- 4-(4-benzylpiperidin-1-yl)-6-(4-(4-methylpiperazin-1-yl)phenyl)-9H-pyrido[2,3-b]indole (R664) and
- 4-(4-benzylpiperazin-1-yl)-6-(4-(4-methylpiperazin-1-yl)phenyl)-9H-pyrido[2,3-b]indole (R665)

In yet another embodiment (Embodiment G3), there is provided a compound selected from the list of:

4-(1-(4-methylbenzyl)-1H-1,2,3-triazol-4-yl)-6-(4-(4-methylpiperazin-1-yl)phenyl)-9H-pyrido[2,3-b]indole (R620);
6-(4-(4-methylpiperazin-1-yl)phenyl)-4-(4-phenoxyphenyl)-9H-pyrido[2,3-b]indole (R621);
4-(6-(4-fluorophenyl)pyridin-3-yl)-6-(4-(4-methylpiperazin-1-yl)phenyl)-9H-pyrido[2,3-b]indole (R650);
(2,5-dimethoxy-4-(6-(4-(4-methylpiperazin-1-yl)phenyl)-9H-pyrido[2,3-b]indol-4-yl)phenyl)(phenyl)methanone (R654);
(2-hydroxy-5-methoxy-4-(6-(4-(4-methylpiperazin-1-yl)phenyl)-9H-pyrido[2,3-b]indol-4-yl)phenyl)(phenyl)methanone (R656);
4-(4-benzyl-2,5-dimethoxyphenyl)-6-(4-(4-methylpiperazin-1-yl)phenyl)-9H-pyrido[2,3-b]indole (R666);
2-benzyl-4-methoxy-5-(6-(4-(4-methylpiperazin-1-yl)phenyl)-9H-pyrido[2,3-b]indol-4-yl)phenol (R667);
4-(4-benzyl-3-(trifluoromethyl)phenyl)-6-(4-(4-methylpiperazin-1-yl)phenyl)-9H-pyrido[2,3-b]indole (R686);
4-(4-benzyl-2-(trifluoromethyl)phenyl)-6-(4-(4-methylpiperazin-1-yl)phenyl)-9H-pyrido[2,3-b]indole (R687);
4-(4-benzyl-3,5-dimethoxyphenyl)-6-(4-(4-methylpiperazin-1-yl)phenyl)-9H-pyrido[2,3-b]indole (R696);
(2,5-dimethoxy-4-(6-(4-(4-methylpiperazin-1-yl)phenyl)-9H-pyrido[2,3-b]indol-4-yl)phenyl)(phenyl)methanol (R655);
4-(4-benzylpiperidin-1-yl)-6-(4-(4-methylpiperazin-1-yl)phenyl)-9H-pyrido[2,3-b]indole (R664) and
4-(4-benzylpiperazin-1-yl)-6-(4-(4-methylpiperazin-1-yl)phenyl)-9H-pyrido[2,3-b]indole (R665)

In yet another embodiment (embodiment G4), there is provided a compound selected from the list of:
4-Biphenyl-4-yl-6-[4-(4-methylpiperazin-1-yl)phenyl]-9H-pyrido[2,3-b]indole (R510a);
(E)-4-(2-(2-Methoxyphenyl)vinyl))-6-(4-(4-methylpiperazin-1-yl)phenyl)-9H-pyrido[2,3-b]indole (R520);
(E)-6-(4-(4-Methylpiperazin-1-yl)phenyl)-4-(2-(2-(trifluoromethyl)phenyl)vinyl)-9H-pyrido[2,3-b]indole (R521);
4-[4-(4-Chloro-3-methylphenoxymethyl)phenyl]-6-[4-(4-methylpiperazin-1-yl)phenyl]-9H-pyrido[2,3-b]indole (R522);
(E)-4-(2-(4-Fluorophenyl)vinyl))-6-(4-(4-methylpiperazin-1-yl)phenyl)-9H-pyrido[2,3-b]indole (R527);
4-(4-Benzylphenyl)-6-[4-(4-methylpiperazin-1-yl)phenyl]-9H-pyrido[2,3-b]indole (R533);
4-Biphenyl-3-yl-6-[4-(4-methylpiperazin-1-yl)phenyl]-9H-pyrido[2,3-b]indole (R534);
4-((2-Methoxyphenyl)ethynyl)-6-[4-(4-methylpiperazin-1-yl)phenyl]-9H-pyrido[2,3-b]indole (R538);
6-(4-(4-Methylpiperazin-1-yl)phenyl)-N-(3-nitrophenyl)-9H-pyrido[2,3-b]indol-4-amine(R547);
(4-{6-[4-(4-Methylpiperazin-1-yl)phenyl]-9H-pyrido[2,3-b]indol-4-yl}-phenyl)phenyl-methanol (R570);
(4-{6-[4-(4-Methylpiperazin-1-yl)phenyl]-9H-pyrido[2,3-b]indol-4-yl}-phenyl)phenyl-methanone (R571);
6-[4-(4-Methylpiperazin-1-yl)phenyl]-4-(4-naphthalen-1-yl-phenyl)-9H-pyrido[2,3-b]indole (R590).

In yet another embodiment (Embodiment G5), there is provided a compound selected from the list of:
4-(4-benzylpiperidin-1-yl)-6-(4-(4-methylpiperazin-1-yl)phenyl)-9H-pyrido[2,3-b]indole (R664);
4-(4-benzylpiperazin-1-yl)-6-(4-(4-methylpiperazin-1-yl)phenyl)-9H-pyrido[2,3-b]indole (R665) and
4-(4-benzyl-2,5-dimethoxyphenyl)-6-(4-(4-methylpiperazin-1-yl)phenyl)-9H-pyrido[2,3-b]indole (R666)

In yet a further embodiment, there is provided a compound selected from the lists of embodiments G4 and G5.

In a particular embodiment (embodiment G6), there is provided a compound selected from the list of:
4-((4-Methoxyphenyl)thio)-6-(4-(4-methylpiperazin-1-yl)phenyl)-9H-pyrido[2,3-b]indole (R619).

In a particular embodiment of formula (I) or embodiment A1, R2 is selected from

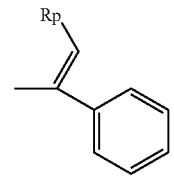

and Rp is as defined under formula (I) or embodiment A1.

In a particular embodiment of formula (I) or embodiment A1, R2 is selected from

and Rs is as defined under formula (I) or embodiment A1.

In a particular embodiment of formula (I) or embodiment A1, R2 is selected from

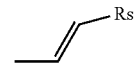

and Rs is as defined under formula (I) or embodiment A1.

In a particular aspect of formula (I), embodiment A1, embodiment C1, or embodiment C2, R2 is selected from

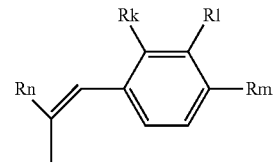

and Rk, Rl, Rm and Rn are as defined under formula (I), embodiment A1 or embodiment C1 or embodiment C2.

In a particular embodiment of formula (I) (embodiment E), —R2 is selected from

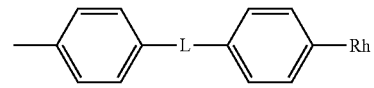

and L and Rh are as defined under formula (I).

In a particular aspect of embodiment E, L is selected from the list of S, SO and SO$_2$.

In a particular aspect of embodiment E, L is O.

In a particular embodiment of formula (I) (Embodiment F), R2 is selected from

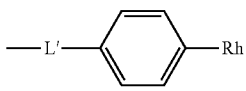

and L' and Rh are as defined under formula (I).

In a particular aspect of embodiment F, L' is selected from the list of S, SO and $SO_2$.

In a particular aspect of embodiment F, L' is O.

In another aspect of this invention, there is provided compounds of formula (II), wherein R3 and X are as defined under formula (I) or embodiment A or embodiment B above, which are useful intermediates towards the synthesis of compounds of formula (I).

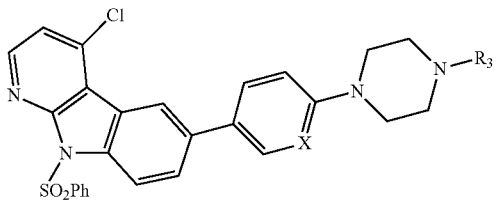

(II)

In a particular embodiment of formula (II), there is provided a compound selected from the list of:

9-Benzenesulfonyl-4-chloro-6-[4-(4-methylpiperazin-1-yl)-phenyl]-9H-pyrido[2,3-b]indole (Building block A);

9-Benzenesulfonyl-4-chloro-6-[4-(6-methylpiperazin-1-yl)-pyridin-3-yl]-9H-pyrido[2,3-b]indole (Building block B);

9-Benzenesulfonyl-4-chloro-6-(4-(4-(1-methylpiperidin-4-yl)piperazin-1-yl)phenyl)-9H-pyrido[2,3-b]indole (Building block C).

All embodiments may be combined.

In the above embodiments, when R2 is

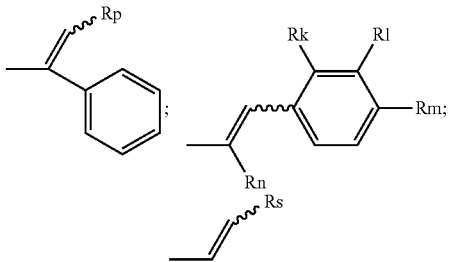

the wavy bond is intended to encompass the E-stereoisomer, the Z-stereoisomer and mixtures thereof.

General Route to Compounds of the Invention

Compounds of the invention may be obtained starting from intermediate X below, which synthesis is described in EP2161271.

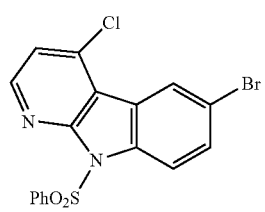

X

Intermediate X can then be transformed into building block Y via Suzuki coupling as summarized below and better illustrated further.

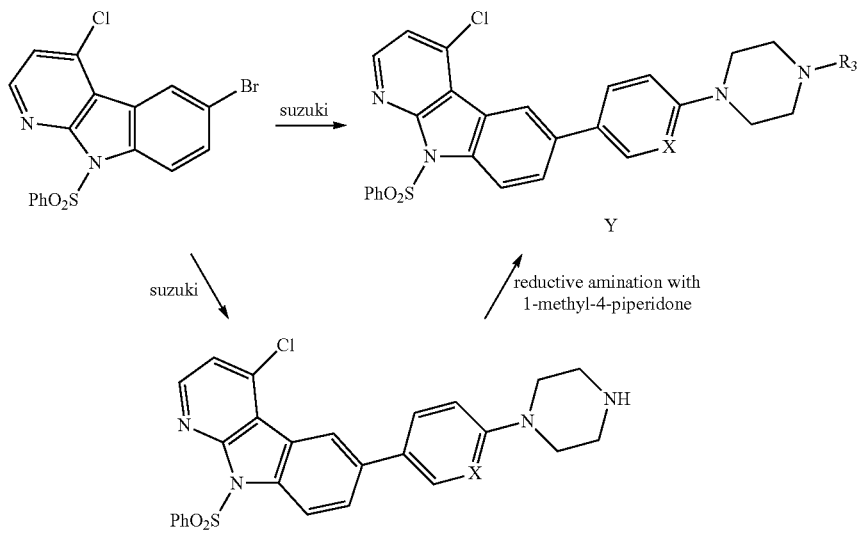

Compounds where R2 is

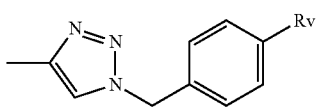

can be obtained via a copper catalyzed azide-alkyne cycloaddition on the compound where R2 is ethynyl.

In all other cases, R2 can then be introduced via a Pd catalysed coupling reaction to yield intermediate Z below.

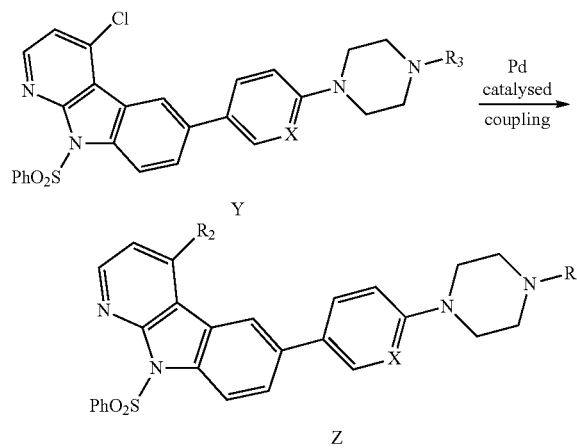

When R2 is

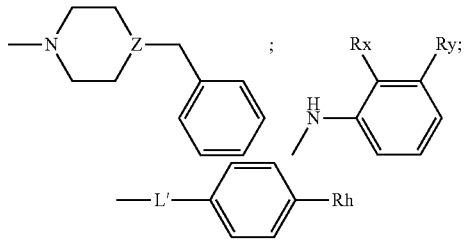

and L' is S, it can be introduced via a Buchwald coupling or by nucleophilic substitution.

When R2 is

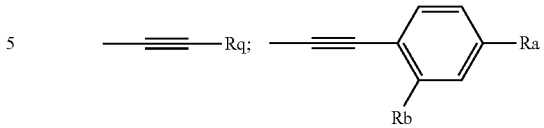

it can be introduced via a Sonogashira coupling. Such compounds can also be obtained by Sonogashira coupling on a compound where Rq is H.

In all other cases R2 can be introduced via a Suzuki coupling.

The subsequent deprotection of intermediate Z from the benzenesulfonyl group under standard conditions yields compounds with R1=H. These may further be alkylated using suitable standard procedures.

Compounds where L or L' are SO or $SO_2$ can also be obtained by oxidation of the corresponding thioether where L or L' is S.

Compounds where Rz and Rz' are hydroxyl can be obtained by the reduction of the corresponding compounds where Rz or Rz' are oxo Alternative Routes When R2 is

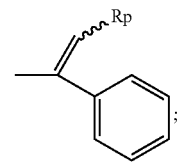

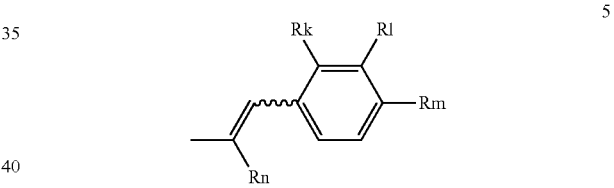

the route above described may result in mixtures of regio- and stereo-isomers.

A regiospecific route to these compounds may involve an olefination reaction such as stereoselective modified Julia reaction (Julia-Kocienski vs Julia-Charette), as depicted below for Rp or Rn being ethyl.

The stereochemistry can also be controlled by thermodynamic equilibration.

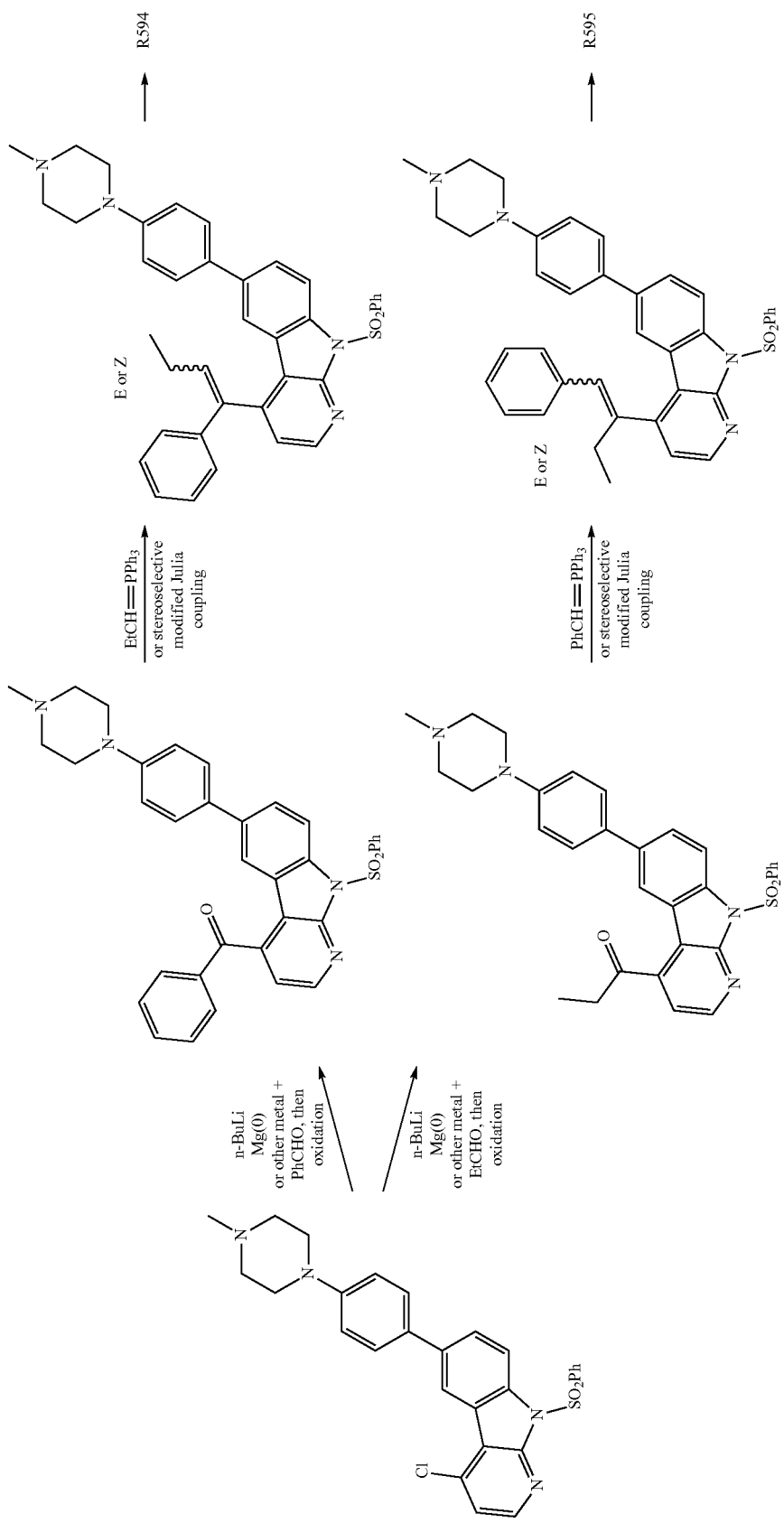

A stereoselective route to these compounds may pass by addition to alpha-alkoxy ketones under either Felkin-Ahn or Cram Chelate selectivity and anti elimination reactions, as depicted below for Rp or Rn being ethyl:

Biological Evaluation

The compounds of the invention may be tested in a relevant animal model or in the following assays.

ELISA-Based In Vitro Kinase Assay

GST-tagged recombinant wild-type or L1196M mutated ALK kinase (rALK) was expressed in Sf9 insect cells using the pBacPAK baculovirus vector system (Clontech) and purified using Glutathione Sepharose 4B affinity beads (GE Healthcare). Recombinant 3C protease was used to remove the GST tag. Purified ALK was used to screen inhibitors in the ELISA-based kinase assay, as follows: Nunc-Immuno 96-well plates were incubated overnight at 30° C. with coating solution containing 2 µg of a specific ALK peptide substrate (ARDIYRASFFRKGGCAMLPVK) in PBS. Wells were then washed with 200 µL of wash buffer (PBS-Tween 0.05%) and incubated with 4% BSA in PBS for at least 2 h at 30° C. The kinase reaction was performed in the presence of 50 mM Tris pH 7.5, 5 mM $MnCl_2$, 5 mM $MgCl_2$, 0.3 mM ATP and purified rALK in a total volume of 100 µL/well at 30° C. for 15 min. For inhibitor testing the reaction mix was preincubated with inhibitor or vehicle for 10 min at room temperature before transferring to the ELISA plate. After the reaction, the wells were washed 5 times with 200 uL of wash buffer. Phosphorylated peptide was detected using 100 µL/well of a mouse monoclonal anti-phosphotyrosine antibody (clone 4G10 UpstateBiotech Ltd) diluted 1:2000 in PBS+4% BSA. After 30 min incubation at room temperature the antibody was removed and wells were washed as described above. 100 µL of a secondary antibody (anti-mouse IgG, Horseradish Peroxidase linked whole antibody, Amersham Pharmacia Biotech) diluted 1:1000 in PBS+4% BSA was added to each well and the plate was incubated again for 30 min at room temperature before washing as above. The plate was developed using 100 µL/well TMB Substrate Solution (Pierce) and the reaction was stopped by adding an equal volume of 1M $H_2SO_4$. Finally, the absorbance was read at 450 nm using an ELISA plate reader (Bio-Rad). The concentration of inhibitor showing 50% inhibition as compared with the control was expressed as $IC_{50}$ (µM).

Tritiated Thymidine Uptake Cell Proliferation Assay

The following procedure uses parental untransformed BaF3 cells, BaF3 cells transformed with the oncogenic fusion protein NPM/ALK, BaF3 cells transformed with the mutated oncogenic fusion protein NPM/ALK carrying the substitution L1196M, human NPM/ALK-positive SUDHL-1 and Karpas-299 cells, human ALK-negative U937 and HL-60 leukemic cells. The parent untransformed BaF3 cells and ALK-negative cells are used as controls. Cells are seeded in U-bottomed 96-well plates at 10 000 cells/well in a volume of 100 µL in supplemented medium. In the case of the parent untransformed BaF3 cells, the medium is supplemented with IL-3. Serial dilutions of inhibitors are added to the appropriate wells and volumes adjusted to 200 pt. Controls were treated with the equivalent volume of vehicle, DMSO, alone. Plates are incubated at 37° C. for 72 h. $^3$[H]-thymidine (1 µLCi/well) is added for the last 8 h of incubation. Cells are harvested on to paper filters and $^3$[H]-thymidine incorporation is measured using a β scintillation counter (1430 MicroBeta, Wallac, Turku, Finland). The 50% inhibitory concentration ($IC_{50}$) is defined as the concentration of inhibitor, expressed in micromolar, that give a 50% decrease in $^3$[H]-thymidine uptake compared with controls.

Formulation and Administration

Compounds under formula I are formulated preferably in admixture with a pharmaceutically acceptable carrier, excipient or the like. In general, it is preferable to administer the pharmaceutical composition in orally-administrable form, but certain formulations may be administered via a parenteral, intravenous, intramuscular, transdermal, buccal, subcutaneous, suppository, nasal or other route. One of ordinary skill in the art may modify the formulations within the teachings of the specification to provide numerous formulations for a particular route of administration without rendering the compositions of the present invention unstable or compromising their therapeutic activity. In particular, the modification of the present compounds to render them more soluble in water or other vehicle, for example, may be easily accomplished by minor modifications (salt formulation, esterification, etc.) which are well within the ordinary skill in the art. It is also well within the routineer's skill to modify the route of administration and dosage regimen of a particular compound in order to manage the pharmacokinetics of the present compounds for maximum beneficial effect in patients. In certain pharmaceutical dosage forms, the pro-drug form of the compounds, especially including ester and ether derivatives, as well as various salt forms of the present compounds, are preferred. One of ordinary skill in the art will recognize how to readily modify the present compounds to pro-drug forms to facilitate delivery of active compounds to a targeted site within the host organism or patient. The routineer also will take advantage of favourable pharmacokinetic parameters of the pro-drug forms, where applicable, in delivering the present compounds to a targeted site within the host organism or patient to maximize the intended effect of the compound. Actual methods of preparing such dosage forms are known, or will be apparent, to those skilled in this art; for example, see Remington's Pharmaceutical Sciences, Mack Publishing Company, Easton, Pa., 15th Edition, 1975. The composition or formulation to be administered will, in any event, contain a quantity of the active compound in an amount effective to alleviate the symptoms of the subject being treated. While human dosage levels have yet to be optimized for the compounds of the invention, generally, a daily dose is from about 0.05 mg/kg to about 100 mg/kg of body weight. The amount of active compound administered will, of course, be dependent on the subject and disease state being treated, the severity of the affliction, the manner and schedule of administration and the judgment of the prescribing physician. For purposes of the present invention, a prophylactically or preventive effective amount of the compositions according to the present invention (i.e., an amount which substantially reduces the risk that a patient will either succumb to a disease state or condition or that the disease state or condition will worsen) falls within the same concentration range as set forth above for therapeutically effective amounts and is usually the same as a therapeutically effective amount. In some embodiments of the present invention, one or more compounds of formula (I) are administered in combination with one or more other pharmaceutically active agents. The phrase "in combination", as used herein, refers to agents that are simultaneously administered to a subject. It will be appreciated that two or more agents are considered to be administered "in combination" whenever a subject is simultaneously exposed to both (or more) of the agents. Each of the two or more agents may be administered according to a different schedule; it is not required that individual doses of different agents be administered at the same time, or in the same composition.

Rather, so long as both (or more) agents remain in the subject's body, they are considered to be administered "in combination".

EXAMPLES

Synthesis of Building Blocks a, B and C

Building block A: 9-Benzenesulfonyl-4-chloro-6[4-(4-methylpiperazin-1-yl)-phenyl]-9H-pyrido[2,3-1)]indole To a 0.03 M solution of 9-Benzenesulfonyl-6-bromo-4-chloro-9H-pyrido[2,3-b]indole in THF, at room temperature and under inert atmosphere, Pd(PPh$_3$)$_4$ (0.15 equiv.), K$_2$CO$_3$ (3 equiv.) and the boronic pinacol ester (1.1 equiv.) were added. The mixture was heated to 70° C. and degassed H$_2$O mQ (25% of the volume of THF used) was added. After stirring at 70° C. for 4 h, the reaction mixture was cooled to room temperature, diluted with EtOAc (1 volume) and then filtered through Celite. The pad of Celite was washed with EtOAc and the filtrate was evaporated to dryness. The residue was dissolved in EtOAc and washed twice with H$_2$O mQ. The organic layer was dried over MgSO$_4$, filtered and evaporated to dryness. The residue was suspended in a minimum volume of methanol, triturated and filtered, and the solid washed with methanol, to afford the desired compound

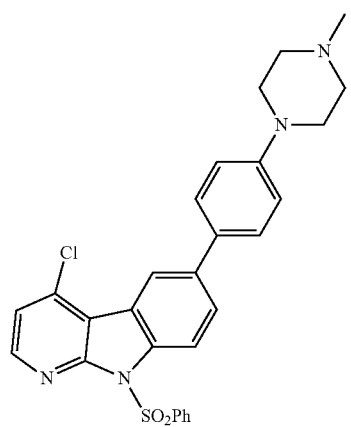

The trituration procedure afforded the desired compound in 77% yield as a yellowish solid. $^1$H-NMR (300 MHz, CDCl$_3$) δ=8.57 (d, J=1.6 Hz, 1H), 8.54 (d, J=8.8 Hz, 1H), 8.43 (d, J=5.4 Hz, 1H), 8.20-8.12 (m, 2H), 7.82 (dd, J=8.8, 1.9 Hz, 1H), 7.60 (d, J=8.8 Hz, 2H), 7.58-7.49 (m, 1H), 7.43 (t, J=7.6 Hz, 2H), 7.30 (d, J=5.4 Hz, 1H), 7.05 (d, J=8.8 Hz, 2H), 3.41-3.29 (m, 4H), 2.77-2.64 (m, 4H), 2.44 (s, 3H). $^{13}$C-NMR (75 MHz, CDCl$_3$) δ=151.88 (CH), 150.80 (Cq), 146.75 (CH), 138.54 (Cq), 138.48 (Cq), 137.44 (Cq), 136.49 (Cq), 134.25 (CH), 131.60 (Cq), 129.11 (2 CH), 128.06 (2 CH), 127.80 (CH), 127.72 (2 CH), 122.42 (Cq), 120.96 (CH), 120.36 (CH), 116.86 (Cq), 116.27 (2 CH), 114.96 (Cq), 55.15 (2 CH$_2$), 48.93 (2 CH$_2$), 46.28 (CH$_3$). ESI-MS: 517.1 m/z [M+H]$^+$.

Building block B: 9-Benzenesulfonyl-4-chloro-6[6-(4-methylpiperazin-1-yl)-pyridin-3-yl]-9H-pyrido[2,3-b]indole

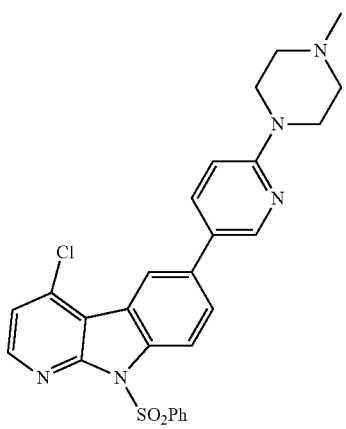

In an analogous procedure to the one described for building block A above, the trituration procedure afforded the desired compound in 73% yield as a yellowish solid. $^1$H NMR (400 MHz, CDCl$_3$) δ 8.60-8.51 (m, 3H), 8.44 (d, J=5.3 Hz, 1H), 8.19-8.13 (m, 2H), 7.81 (dd, J=8.8, 2.5 Hz, 1H), 7.77 (dd, J=8.8, 1.9 Hz, 1H), 7.58-7.51 (m, 1H), 7.47-7.40 (m, 2H), 7.30 (d, J=5.4 Hz, 1H), 6.78 (d, J=8.8 Hz, 1H), 3.74-3.64 (m, 4H), 2.69-2.59 (m, 4H), 2.43 (s, J=6.4 Hz, 3H). $^{13}$C-NMR (101 MHz, CDCl$_3$) δ=158.7 (C), 151.9 (C), 147.0 (CH), 146.5 (CH), 138.6 (C), 136.7 (C), 136.5 (CH), 134.8 (C), 134.3 (CH), 129.2 (2 CH), 128.5 (C), 127.8 (2 CH), 127.4 (CH), 126.0 (C), 122.6 (C), 120.8 (CH), 120.4 (CH), 116.7 (C), 115.3 (CH), 107.1 (CH), 54.9 (2 CH$_2$), 46.2 (CH$_3$), 45.1 (2 CH$_2$). ESI-MS: 518.2 m/z [M+H]$^+$.

Building block C: 9-Benzenesulfonyl-4-chloro-6-(4-(4-(1-methylpiperidin-4-yl)piperazin-1-yl)phenyl)-9H-pyrido[2,3-b]indole Method A:

9-Benzenesulfonyl-4-chloro-6-(4-(piperazin-1-yl)phenyl)-9H-pyrido[2,3-b]indole

In a Schlenk tube, at r.t. and under inert atmosphere, Pd(Ph$_3$)$_4$ (0.1 eq), K$_2$CO$_3$ (3 eq) and boronic acid (1.3 eq) were added to a 0.04M suspension of 9-benzenesulfonyl-6-bromo-4-chloro-9H-pyrido[2,3-b]indole in THF/H$_2$O 4:1 mixture. This solution was stirred at 70° C. for 15 h. After cooling to r.t. and diluting with EtOAc, the mixture was filtered through a Celite® pad. The solvents were removed under reduced pressure. The crude product was triturated in MeOH and filtered. Then, the remaining solid was purified by silica gel flash chromatography (DCM/MeOH 90:10) to afford the desired compound in 38% yield as a white solid.

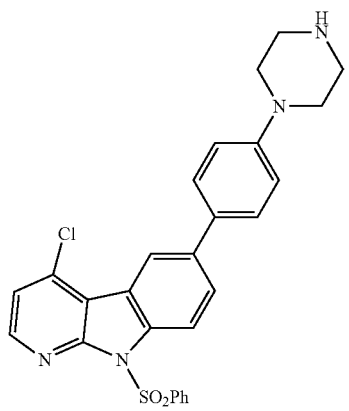

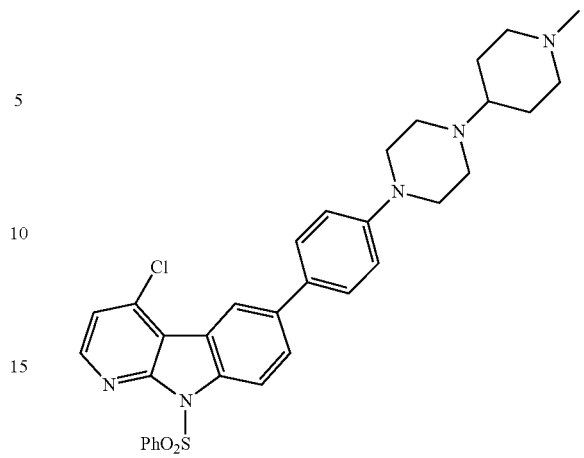

¹H NMR (300 MHz, CDCl₃) δ 8.57 (d, J=1.8 Hz, 1H), 8.54 (d, J=8.9 Hz, 1H), 8.43 (d, J=5.4 Hz, 1H), 8.19-8.12 (m, 2H), 7.81 (dd, J=8.8, 1.9 Hz, 1H), 7.59 (d, J=8.7 Hz, 2H), 7.53 (t, J=7.4 Hz, 1H), 7.42 (t, J=7.6 Hz, 2H), 7.28 (d, J=5.4 Hz, 1H), 7.03 (d, J=8.8 Hz, 2H), 3.23 (dd, J=6.2, 3.7 Hz, 4H), 3.08 (dd, J=6.1, 3.7 Hz, 4H), 2.25 (s, 1H); ¹³C NMR (75 MHz, CDCl₃) δ 151.9 (C), 151.3 (C), 146.8 (CH), 138.6 (C), 138.5 (C), 137.4 (C), 136.5 (C), 134.2 (CH), 131.7 (C), 129.1 (CH), 128.0 (CH), 127.8 (CH), 127.7 (CH), 122.4 (C), 120.9 (CH), 120.4 (CH), 116.8 (C), 116.4 (CH), 115.0 (CH), 50.1 (CH₂), 46.1 (CH₂); MS (ESI) m/z: 503.1 [M+H]⁺.

9-Benzenesulfonyl-4-chloro-6-(4-(4-(1-methylpiperidin-4-yl)piperazin-1-yl)phenyl)-9H-pyrido[2,3-b]indole Under an inert atmosphere 9-benzenesulfonyl-4-chloro-6-(4-(piperazin-1-yl)phenyl)-9H-pyrido[2,3-b]indole (30 mg, 0.0596 mmol) was dissolved in anhydrous DCM (1.2 mL, c=0.05M). N-methyl-4-piperidone (22 µL, 3 eq) was added, followed by the addition of two drops of glacial acetic acid. The mixture was stirred for 1 h15 at r.t. and then cooled to 0° C. Sodium triacetoxyborohydride (38 mg, 3eq) was added in portions and the resultant mixture was allowed to warm to room temperature, and then stirred 22 h. The reaction mixture was then quenched with water and saturated aq. NaHCO₃. The aqueous layer was extracted with EtOAc (3×7 mL). The combined organic layers were washed with brine, dried over MgSO₄, filtered and concentrated in vacuo to yield the desired compound (33 mg, 93%) as a white solid that was used without further purification.

Method B: In a Schlenk tube, at r.t. and under inert atmosphere, Pd(Ph₃)₄ (0.1 eq), K₂CO₃ (3 eq) and 1-(1-methylpiperidin-4-yl)-4-(4-(4,4,5,5-tetramethyl-1,3,2-dioxaborolan-2-yl)phenyl)piperazine (1.3 eq) were added to a 0.04M suspension of 9-benzenesulfonyl-6-bromo-4-chloro-9H-pyrido[2,3-b]indole in THF/H₂O 6:1 mixture. This solution was stirred at 70° C. for 15 h. After cooling to r.t. and diluting with EtOAc, the mixture was filtered through a Celite® pad. The solvents were removed under reduced pressure in vacuo. A white solid was obtained in 74% yield after trituration of the crude product in MeOH and filtration.

¹H NMR (400 MHz, CDCl₃) δ 8.56 (d, J=1.8 Hz, 1H), 8.53 (d, J=8.8 Hz, 1H), 8.42 (d, J=5.4 Hz, 1H), 8.15 (d, J=7.6 Hz, 2H), 7.80 (dd, J=8.8, 1.8 Hz, 1H), 7.58 (d, J=8.7 Hz, 2H), 7.52 (t, J=7.4 Hz, 1H), 7.42 (t, J=7.8 Hz, 2H), 7.28 (d, J=5.4 Hz, 1H), 7.02 (d, J=8.7 Hz, 2H), 3.33-3.21 (m, 4H), 2.98 (d, J=11.7 Hz, 2H), 2.79-2.71 (m, 4H), 2.32 (s, 4H), 2.06 (t, J=10.8 Hz, 2H), 1.88 (d, J=12.1 Hz, 2H), 1.70 (dd, J=20.6, 11.3 Hz, 2H); ¹³C NMR (101 MHz, CDCl₃) δ 151.9 (C), 150.9 (C), 146.7 (CH), 138.6 (C), 138.5 (C), 137.4 (C), 136.5 (C), 134.2 (CH), 131.5 (C), 129.1 (CH), 128.0 (CH), 127.8 (CH), 127.7 (CH), 122.4 (C), 120.9 (CH), 120.3 (CH), 116.8 (C), 116.2 (CH), 114.9 (CH), 61.2 (CH), 55.5, 55.2 (CH₂), 49.3 (CH₂), 49.2 (CH₂), 46.0, 45.6 (NCH₃), 27.9 (CH₂); MS (ESI) m/z: 600.2 [M+H]⁺, 1198.9 [2M+H]⁺.

Typical Procedure a: Deprotection from the Benzenesulfonyl Group

To a 0.11 M solution of 4,6-substituted alfa-carboline in THF, at room temperature and under an inert atmosphere, MeOH (in a 7:4 ratio MeOH/THF) and NaOMe (15 equiv.) were added. The reaction mixture was allowed to stir at 65° C. with a reflux condenser for 1.6 h. Then the reaction mixture was cooled to room temperature and quenched with H₂O (1 mL). The mixture was diluted with CH₂Cl₂ (20 mL) and washed twice with H₂O (20 mL) The organic layer was dried over MgSO₄, filtered and evaporated to dryness. The residue was suspended in a minimum volume of methanol, triturated and filtered, and the solid washed with methanol, to afford the desired final compounds. When the trituration was not able to afford acceptable purity, the desired compound was purified by silica gel flash chromatography.

Typical Procedure B: Suzuki Coupling

To a 0.1 M solution of 9-Benzenesulfonyl-6-substituted-4-chloro-9H-pyrido[2,3-b]indole in dioxane, at room temperature and under inert atmosphere, Pd(PPh₃)₄ (0.15 equiv.), K₂CO₃ (3 equiv.), the boronic acid or pinacol ester (2 equiv.) and degassed H₂O mQ (20% of the volume of dioxane) were added. An oil-bath was placed and the mixture was heated to 100° C. After stirring overnight at 100° C., the reaction mixture was cooled to room temperature, diluted with EtOAc (3 volumes) and then filtered through Celite. The pad of Celite was washed with EtOAc and the filtrate was washed twice with H₂O mQ. The organic layer was dried over MgSO₄, filtered and evaporated to dryness. The residue was suspended in a minimum volume of methanol, triturated and filtered, and the solid washed with methanol.

Example 1

4-Chloro-6-[4-(4-methylpiperazin-1-yl)-phenyl]-9H-pyrido[2,3-b]indole (R588)

Building block A was deprotected under typical procedure A.

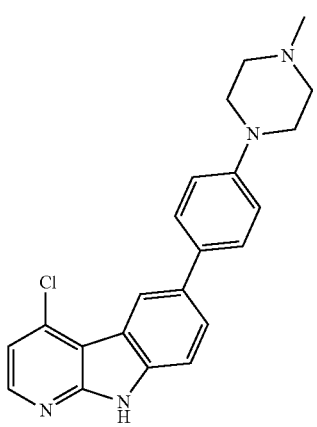 [SMILES: CN1CCN(c2ccc(-c3ccc4[nH]c5nccc(Cl)c5c4c3)cc2)CC1]

Purification by silica gel flash chromatography (CH$_2$Cl$_2$/MeOH 95:5) afforded the desired compound in 57% yield as a yellow solid. $^1$H-NMR (300 MHz, CDCl$_3$/MeOD 5:2) δ=8.56 (d, J=1.3 Hz, 1H), 8.22 (d, J=5.5 Hz, 1H), 7.72 (dd, J=8.5, 1.8 Hz, 1H), 7.59 (d, J=8.8 Hz, 3H), 7.17 (d, J=5.5 Hz, 1H), 7.04 (d, J=8.8 Hz, 2H), 3.30-3.24 (m, 4H), 2.75-2.67 (m, 4H), 2.41 (s, 3H). $^{13}$C-NMR (101 MHz, CDCl$_3$/MeOD 5:2) δ=153.38 (Cq), 150.33 (Cq), 145.83 (CH), 139.15 (Cq), 138.79 (Cq), 134.48 (Cq), 134.23 (Cq), 128.46 (2 CH), 127.21 (CH), 121.36 (CH), 120.97 (Cq), 117.42 (2 CH), 116.49 (CH), 115.28 (Cq), 112.09 (CH), 55.22 (2 CH$_2$), 49.27 (2 CH$_2$), 45.70 (CH$_3$). HRMS (ESI): calcd. for C$_{22}$H$_{22}$N$_4$Cl: 377.1528. found: 377.1518.

Example 2

(E)-6-[4-(4-Methylpiperazin-1-yl)-phenyl]-4-(2-phenylvinyl)-9H-pyrido[2,3-b]indole (R500a)

9-Benzenesulfonyl-6-[4-(4-methylpiperazin-1-yl)-phenyl]-4-(2-phenylvinyl)-9H-pyrido[2,3-1)]indole Building block A underwent typical procedure B to afford the desired compound in 73% yield as a yellow solid.

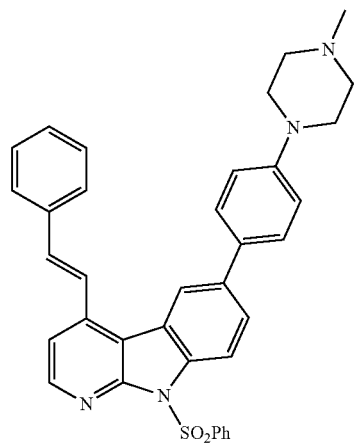

$^1$H-NMR (300 MHz, CDCl$_3$) δ=8.58 (d, J=8.8 Hz, 1H), 8.52 (d, J=5.2 Hz, 1H), 8.24 (d, J=1.4 Hz, 1H), 8.20-8.13 (m, 2H), 7.85 (d, J=16.2 Hz, 1H), 7.76 (dd, J=8.8, 1.8 Hz, 1H), 7.65-7.55 (m, 4H), 7.56-7.49 (m, 1H), 7.48-7.35 (m, 6H), 7.36 (d, J=16.4 Hz, 1H), 7.04 (d, J=8.7 Hz, 2H), 3.36-3.23 (m, 4H), 2.67-2.56 (m, 4H), 2.38 (s, 3H). $^{13}$C-NMR (75 MHz, CDCl$_3$) δ=151.98 (C), 150.77 (C), 146.66 (CH), 141.64 (C), 138.93 (C), 137.31 (C), 136.74 (C), 136.33 (C), 135.78 (CH), 134.01 (CH), 132.00 (C), 129.20 (3 CH), 129.02 (2 CH), 128.03 (2 CH), 127.76 (2 CH), 127.31 (2 CH), 127.01 (CH), 124.08 (C), 123.49 (CH), 120.98 (CH), 116.37 (2 CH), 116.05 (C), 116.01 (CH), 115.27 (CH), 55.22 (2$_2$), 48.99 (2 CH$_2$), 46.33 (CH$_3$). ESI-MS: 585.2 m/z

(E)-6-[4-(4-Methylpiperazin-1-yl)-phenyl]-4-(2-phenylvinyl)-9H-pyrido[2,3-b]indole 9-Benzenesulfonyl-6-[4-(4-methylpiperazin-1-yl)-phenyl]-4-(2-phenylvinyl)-9H-pyrido[2,3-b]indole underwent typical procedure A to afford the desired compound in 74% yield as a yellow solid.

$^1$H-NMR (300 MHz, DMSO) δ=11.89 (s, 1H), 8.39 (d, J=5.2 Hz, 1H), 8.35 (d, J=1.6 Hz, 1H), 8.16 (d, J=16.2 Hz, 1H), 7.87-7.79 (m, 2H), 7.70 (dd, J=8.5, 1.6 Hz, 1H), 7.67-7.53 (m, 4H), 7.53-7.46 (m, 3H), 7.39 (t, J=7.3 Hz, 1H), 7.05 (d, J=8.8 Hz, 2H), 3.23-3.14 (m, 4H), 2.49-2.43 (m, 4H), 2.24 (s, 3H). $^{13}$C-NMR (126 MHz, DMSO) δ=153.02 (Cq), 149.90 (Cq), 146.01 (CH), 140.26 (Cq), 138.06 (Cq), 136.48 (Cq), 134.67 (CH), 132.33 (Cq), 131.75

(Cq), 129.06 (2 CH), 128.79 (CH), 127.31 (4 CH), 125.18 (CH), 124.21 (CH), 121.05 (Cq), 120.30 (CH), 115.83 (2 CH), 112.51 (Cq), 111.66 (CH), 111.43 (CH), 54.65 (2 CH$_2$), 48.08 (2 CH$_2$), 45.82 (CH$_3$). HRMS (ESI): calcd. for C$_{30}$H$_{29}$N$_4$: 445.2387. found: 445.2378.

Examples 3-32 were synthesised in a similar fashion to example 2, starting from building blocks A, B or C, accordingly.

Example 3

(E)-6-[4-(4-Methylpiperazin-1-yl)-phenyl]-4-[1-(2-(trifluoromethyl)phenyl)prop-1-en-2-yl]-9H-pyrido[2,3-b]indole (R605)

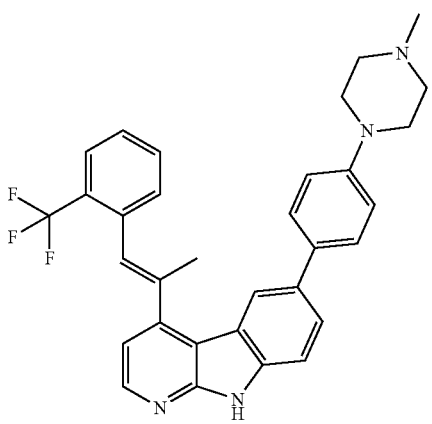 [SMILES: C/C(=C\c1ccccc1C(F)(F)F)c1ccnc2[nH]c3ccc(-c4ccc(N5CCN(C)CC5)cc4)cc3c12]

A yellow solid was obtained in 89% yield after trituration of the crude product in MeOH and filtration. $^1$H NMR (500 MHz, CDCl$_3$) δ 10.07 (s, 1H), 8.51 (d, J=4.9 Hz, 1H), 8.28 (s, 1H), 7.77 (d, J=7.9 Hz, 1H), 7.70 (dd, J=8.4, 1.2 Hz, 1H), 7.68-7.62 (m, 2H), 7.59 (d, J=8.4 Hz, 1H), 7.53 (d, J=8.6 Hz, 2H), 7.47 (t, J=7.4 Hz, 1H), 7.11 (d, J=5.0 Hz, 1H), 7.01 (s, 1H), 7.00 (d, J=8.5 Hz, 2H), 3.41-3.23 (m, 4H), 2.78-2.61 (m, 4H), 2.44 (s, 3H), 2.25 (s, 3H); $^{13}$C NMR (75 MHz, CDCl$_3$) δ 152.9 (C), 150.0 (C), 148.2 (C), 146.0 (CH), 138.7 (C), 137.8 (C), 136.3 (d, J=1.8 Hz, C), 133.7 (C), 133.5 (C), 131.8 (CH), 131.1 (CH), 129.1 (q, 29.5 Hz, C), 128.0 (CH), 127.4 (CH), 127.1 (CH), 126.3 (q, J=5.4 Hz, CH), 126.0 (CH), 124.4 (q, J=274.0 Hz, C), 121.3 (C), 121.0 (CH), 116.6 (CH), 115.3 (CH), 113.5 (C), 111.4 (CH), 55.1 (2CH$_2$), 49.0 (2CH$_2$), 46.1 (NCH$_3$), 18.8 (CH$_3$); HRMS calcd for C$_{32}$H$_{30}$F$_3$N$_4$ [M+H]$^+$ 527.2417 found 527.2402.

Example 4

(E)-6-[6-(4-Methylpiperazin-1-yl)-pyridin-3-yl]-4-(2-phenylvinyl)-9H-pyrido[2,3-b]indole (R505)

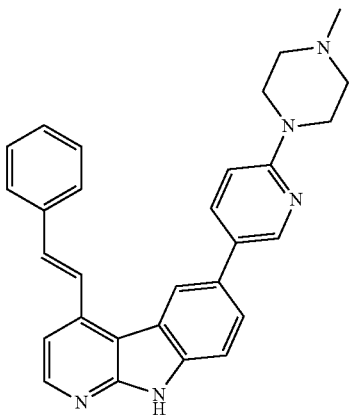 [SMILES: CN1CCN(c2ccc(-c3ccc4[nH]c5nccc(/C=C/c6ccccc6)c5c4c3)cn2)CC1]

The trituration procedure afforded the desired compound in 61% yield as a brown solid. $^1$H-NMR (300 MHz, DMSO) δ=11.92 (s, 1H), 8.54 (d, J=2.4 Hz, 1H), 8.40 (d, J=5.2 Hz, 1H), 8.36 (d, J=1.0 Hz, 1H), 8.17 (d, J=16.3 Hz, 1H), 7.95 (dd, J=8.8, 2.6 Hz, 1H), 7.85 (d, J=7.3 Hz, 2H), 7.70 (dd, J=8.5, 1.5 Hz, 1H), 7.63 (d, J=16.3 Hz, 1H), 7.58 (d, J=8.4 Hz, 1H), 7.53-7.44 (m, 3H), 7.38 (t, J=7.3 Hz, 1H), 6.96 (d, J=8.8 Hz, 1H), 3.60-3.48 (m, 4H), 2.46-2.37 (m, 4H), 2.23 (s, 3H). $^{13}$C-NMR (75 MHz, DMSO) δ=157.98 (Cq), 152.99 (Cq), 146.05 (CH), 145.51 (CH), 140.32 (Cq), 138.16 (Cq), 136.44 (Cq), 136.03 (CH), 134.78 (CH), 129.62 (Cq), 128.97 (2 CH), 128.74 (CH), 127.39 (2 CH), 126.33 (Cq), 124.97 (CH), 124.13 (CH), 121.08 (Cq), 120.30 (CH), 112.37 (Cq), 111.73 (CH), 111.40 (CH), 107.18 (CH), 54.44 (2 CH$_2$), 45.87 (CH$_3$), 44.78 (2 CH$_2$). HRMS (ESI): calcd. for C$_{29}$H$_{28}$N$_5$: 446.2339. found: 446.2323.

Example 5

4-Biphenyl-4-yl-6-[4-(4-methylpiperazin-1-yl)-phenyl]-9H-pyrido[2,3-b]indole (R510a)

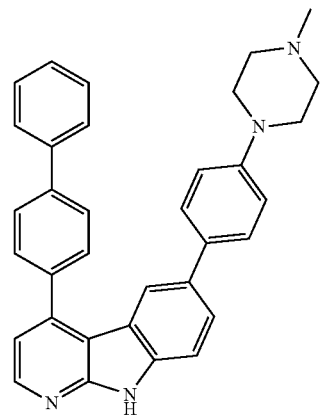 [SMILES: CN1CCN(c2ccc(-c3ccc4[nH]c5nccc(-c6ccc(-c7ccccc7)cc6)c5c4c3)cc2)CC1]

The trituration procedure afforded the desired compound in 88% yield as a beige solid. $^1$H NMR (500 MHz, DMSO)

δ 12.01 (s, 1H), 8.48 (d, J=3.9 Hz, 1H), 7.96 (d, J=7.3 Hz, 2H), 7.90-7.76 (m, 5H), 7.66 (d, J=7.6 Hz, 1H), 7.60-7.50 (m, 3H), 7.48-7.41 (m, 1H), 7.34 (d, J=7.6 Hz, 2H), 7.17 (d, J=4.1 Hz, 1H), 6.93 (d, J=8.0 Hz, 2H), 3.19-3.05 (m, 4H), 2.45-2.39 (m, 4H), 2.20 (s, 3H). $^{13}$C-NMR (126 MHz, DMSO) δ=152.77 (Cq), 149.75 (Cq), 146.18 (CH), 143.90 (Cq), 140.57 (Cq), 139.56 (Cq), 138.00 (Cq), 137.48 (Cq), 131.65 (Cq), 131.34 (Cq), 129.24 (2 CH), 129.11 (2 CH), 127.82 (CH), 127.01 (2 CH), 126.85 (2 CH), 126.82 (2 CH), 125.22 (CH), 120.37 (Cq), 119.08 (CH), 115.81 (CH), 115.64 (2 CH), 112.29 (Cq), 111.70 (CH), 54.54 (2 $CH_2$), 47.91 (2 $CH_2$), 45.74 ($CH_3$). HRMS (ESI): calcd. for $C_{34}H_{31}N_4$: 495.2543. found: 495.2543.

Example 6

(E)-4-[2-(3-Fluorophenyl)vinyl]-6-[4-(4-methylpiperazin-1-yl)-phenyl]-9H-pyrido[2,3-b]indole (R511)

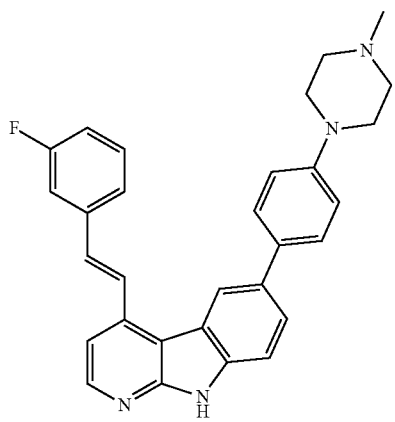 [SMILES: CN1CCN(c2ccc(-c3ccc4[nH]c5nccc(/C=C/c6cccc(F)c6)c5c4c3)cc2)CC1]

The trituration procedure afforded the desired compound in 81% yield as a yellow solid. 1H-NMR (500 MHz, DMSO) δ=11.90 (s, 1H), 8.40 (d, J=5.2 Hz, 1H), 8.36 (d, J=1.6 Hz, 1H), 8.23 (d, J=16.3 Hz, 1H), 7.74 (m 1H), 7.70 (dd, J=8.4, 1.6 Hz, 1H), 7.66 (d, J=7.8 Hz, 1H), 7.64-7.61 (m, 2H), 7.61 (d, J=15.9 Hz, 1H), 7.56 (d, J=8.4 Hz, 1H), 7.52 (dt, J=14.2, 7.1 Hz, 1H), 7.47 (d, J=5.2 Hz, 1H), 7.21 (td, J=8.5, 2.2 Hz, 1H), 7.04 (d, J=8.8 Hz, 2H), 3.22-3.15 (m, 4H), 2.49-2.43 (m, 4H), 2.24 (s, 3H). $^{13}$C-NMR (126 MHz, DMSO) δ=162.65 (d, J=243.3 Hz, Cq), 152.95 (Cq), 149.84 (Cq), 145.96 (CH), 139.86 (Cq), 139.09 (d, J=8.0 Hz, Cq), 138.02 (Cq), 133.41 (d, J=2.4 Hz, CH), 132.27 (Cq), 131.72 (Cq), 130.84 (d, J=8.4 Hz, CH), 127.31 (2 CH), 125.89 (CH), 125.21 (CH), 123.64 (d, J=2.2 Hz, CH), 120.89 (Cq), 120.45 (CH), 115.72 (2 CH), 115.31 (d, J=21.5 Hz, CH), 113.51 (d, J=21.9 Hz, CH), 112.56 (Cq), 111.54 (CH), 111.53 (CH), 54.58 (2 $CH_2$), 48.03 (2 $CH_2$), 45.75 ($CH_3$). HRMS (ESI): calcd. for C30H28FN4: 463.2293. found: 463.2282.

Example 7

(E)-4-[2-(4-Methoxyphenyl)vinyl]-6-[4-(4-methylpiperazin-1-yl)-phenyl]-9H-pyrido[2,3-b]indole (R517)

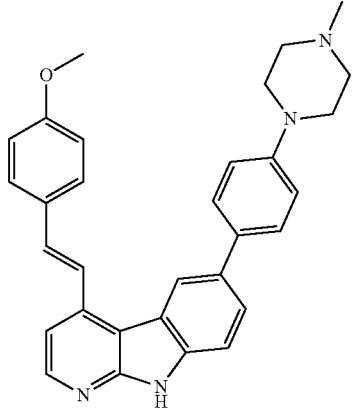 [SMILES: COc1ccc(/C=C/c2ccnc3[nH]c4ccc(-c5ccc(N6CCN(C)CC6)cc5)cc4c23)cc1]

The trituration procedure in MeOH followed by the same procedure in $CH_2Cl_2$ afforded the desired compound in 66% yield as a yellow solid. $^1$H-NMR (500 MHz, DMSO) δ=11.85 (s, 1H), 8.36 (d, J=5.2 Hz, 1H), 8.34 (d, J=1.5 Hz, 1H), 7.98 (d, J=16.2 Hz, 1H), 7.77 (d, J=8.7 Hz, 2H), 7.68 (dd, J=8.4, 1.5 Hz, 1H), 7.64-7.53 (m, 4H), 7.46 (d, J=5.3 Hz, 1H), 7.42 (d, J=8.7 Hz, 1H), 7.05 (d, J=8.0 Hz, 4H), 6.94-6.88 (m, 1H), 3.23-3.14 (m, 4H), 2.49-2.43 (m, 4H), 2.23 (s, 3H). $^{13}$C-NMR (126 MHz, DMSO) δ=159.85 (Cq), 153.03 (Cq), 149.82 (Cq), 145.87 (CH), 140.59 (Cq), 137.94 (Cq), 134.29 (CH), 132.22 (Cq), 131.75 (Cq), 129.08 (Cq), 128.75 (2 CH), 127.44 (CH), 127.27 (2 CH), 121.66 (CH), 121.12 (Cq), 120.21 (CH), 115.78 (2 CH), 114.48 (2 CH), 114.21 (CH), 112.25 (Cq), 111.05 (CH), 55.28 ($CH_3$), 54.62 (2 $CH_2$), 48.05 (2 $CH_2$), 45.78 ($CH_3$). HRMS (ESI): calcd. for $C_{31}H_{31}N_4O$: 475.2492. found: 475.2475.

Example 8

4-(4-Benzyloxyphenyl)-6-[4-(4-methylpiperazin-1-yl)-phenyl]-9H-pyrido[2,3-b]indole (R518)

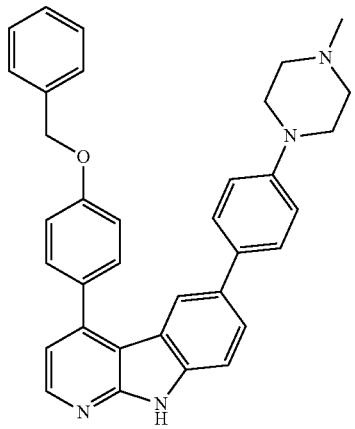 [SMILES: CN1CCN(c2ccc(-c3ccc4[nH]c5nccc(-c6ccc(OCc7ccccc7)cc6)c5c4c3)cc2)CC1]

The trituration procedure in MeOH followed by the same procedure in toluene afforded the desired compound in 32% yield as a brown solid. $^1$H-NMR (500 MHz, DMSO) δ=11.94 (s, 1H), 8.42 (d, J=5.0 Hz, 1H), 7.81 (d, J=1.3 Hz, 1H), 7.70 (d, J=8.6 Hz, 2H), 7.65 (dd, J=8.4, 1.7 Hz, 1H), 7.56-7.50 (m, 3H), 7.44-7.39 (m, 2H), 7.38-7.32 (m, 3H), 7.28 (d, J=8.7 Hz, 2H), 7.08 (d, J=5.0 Hz, 1H), 6.97 (d, J=8.8 Hz, 2H), 5.25 (s, 2H), 3.19-3.11 (m, 4H), 2.47-2.41 (m, 4H), 2.22 (s, 3H). $^{13}$C-NMR (126 MHz, DMSO) δ=158.89 (Cq), 152.80 (Cq), 149.73 (Cq), 146.08 (CH), 144.12 (Cq), 137.91 (Cq), 136.98 (Cq), 131.55 (Cq), 131.43 (Cq), 130.79 (Cq), 129.98 (2 CH), 128.46 (2 CH), 127.86 (CH), 127.71 (2 CH), 126.87 (2 CH), 125.05 (CH), 120.50 (Cq), 119.07 (CH), 115.88 (CH), 115.69 (2 CH), 115.08 (2 CH), 112.30 (Cq), 111.61 (CH), 69.43 (CH$_2$), 54.57 (2 CH$_2$), 47.97 (2 CH$_2$), 45.75 (CH$_3$). HRMS (ESI): calcd. for $C_{35}H_{33}N_4O$: 525.5649. found: 525.2640.

Example 9

6-[4-(4-Methylpiperazin-1-yl)-phenyl]-4-[4-(3-trifluoromethyl-phenoxymethyl)-phenyl]-9H-pyrido[2,3-b]indole (R519)

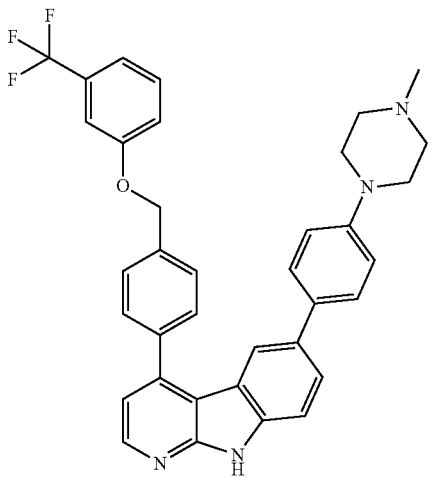 [SMILES: CN1CCN(c2ccc(-c3ccc4[nH]c5nccc(-c6ccc(COc7cccc(C(F)(F)F)c7)cc6)c5c4c3)cc2)CC1]

The trituration procedure in MeOH afforded the desired compound in 87% yield as a dark green solid. $^1$H-NMR (400 MHz, DMSO) δ=12.00 (s, 1H), 8.46 (d, J=5.0 Hz, 1H), 7.82-7.69 (m, 5H), 7.65 (dd, J=8.5, 1.6 Hz, 1H), 7.59-7.50 (m, 2H), 7.43-7.36 (m, 2H), 7.35-7.28 (m, 3H), 7.13 (d, J=5.0 Hz, 1H), 6.92 (d, J=8.8 Hz, 2H), 5.35 (s, 2H), 3.16-3.05 (m, 4H), 2.47-2.39 (m, 4H), 2.21 (s, 3H). $^{13}$C-NMR (101 MHz, DMSO) δ=158.78 (Cq), 152.81 (Cq), 149.80 (Cq), 146.28 (CH), 144.08 (Cq), 138.12 (d, J=7.5 Hz, Cq), 137.33 (Cq), 131.69 (Cq), 131.42 (Cq), 130.87 (CH), 130.64 (Cq), 130.33 (Cq), 128.90 (2 CH), 128.24 (2 CH), 126.94 (2 CH), 125.30 (CH), 122.75 (Cq), 120.42 (Cq), 119.13 (d, J=5.3 Hz, CH), 117.49 (d, J=7.3 Hz, CH), 115.95 (CH), 115.74 (2 CH), 114.99 (CH), 112.40 (Cq), 111.83 (CH), 111.54 (d, J=4.0 Hz, CH), 69.54 (CH$_2$), 54.61 (2 CH$_2$), 48.00 (2 CH$_2$), 45.82 (CH$_3$). HRMS (ESI): calcd. for $C_{36}H_{32}F_3N_4O$: 593.2523. found: 593.2526.

Example 10

(E)-4-(2-(2-Methoxyphenyl)vinyl)-6-(4-(4-methylpiperazin-1-yl)phenyl)-9H-pyrido[2,3-b]indole (R520)

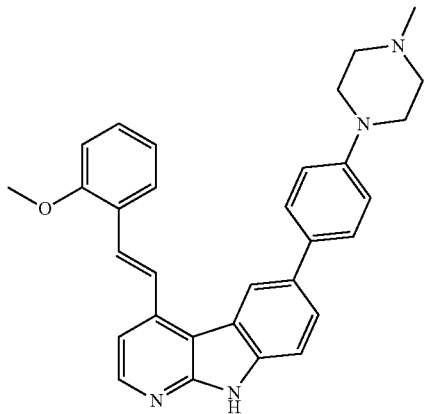 [SMILES: COc1ccccc1/C=C/c1ccnc2[nH]c3ccc(-c4ccc(N5CCN(C)CC5)cc4)cc3c12]

A yellow solid was obtained in 66% yield after trituration of the crude product in MeOH and filtration.
$^1$H NMR (400 MHz, DMSO) δ 11.88 (s, NH), 8.38 (d, J=5.2 Hz, 1H), 8.36 (s, 1H), 8.32 (d, J=16.3 Hz, 1H), 7.78 (dd, J=7.6, 1.4 Hz, 1H), 7.72 (d, J=16.5 Hz, 1H), 7.69 (dd, J=8.7 Hz, 1H), 7.59 (d, J=8.7 Hz, 2H), 7.56 (d, J=8.5 Hz, 1H), 7.48 (d, J=5.3 Hz, 1H), 7.41-7.35 (m, 1H), 7.15 (d, J=8.2 Hz, 1H), 7.07 (t, J=7.3 Hz, 1H), 7.05 (d, J=8.8 Hz, 2H), 3.94 (s, 3H), 3.22-3.14 (m, 4H), 2.49-2.44 (m, 4H), 2.23 (s, 3H); $^{13}$C NMR (101 MHz, DMSO) δ 157.6 (C), 153.1 (C), 149.9 (C), 146.0 (CH), 140.7 (C), 138.0 (C), 132.3 (C), 131.7 (C), 130.5 (CH), 130.0 (CH), 129.4 (CH), 127.3 (CH), 125.4 (CH), 125.1 (CH), 124.6 (C), 121.1 (C), 120.9 (CH), 120.0 (CH), 115.7 (CH), 112.3 (C), 111.7 (CH), 111.6 (CH), 110.8 (CH), 55.8 (CH$_3$), 54.6 (CH$_2$), 48.0 (CH$_2$), 45.8 (CH$_3$); HRMS calcd for $C_{31}H_{31}N_4O$ [M+H]$^+$ 475.2492 found 475.2499.

Example 11

(E)-6-(4-(4-Methylpiperazin-1-yl)phenyl)-4-(2-(2-(trifluoromethyl)phenyl)vinyl)-9H-pyrido[2,3-b]indole (R521)

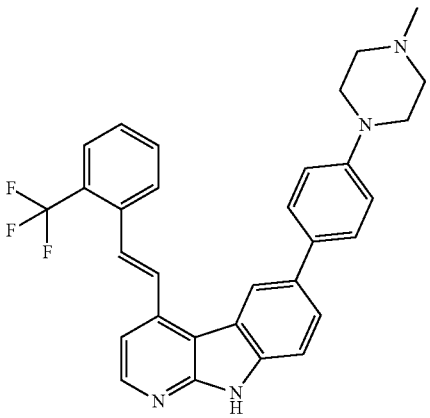 [SMILES: CN1CCN(c2ccc(-c3ccc4[nH]c5nccc(/C=C/c6ccccc6C(F)(F)F)c5c4c3)cc2)CC1]

A yellow solid was obtained in 78% yield after trituration of the crude product in MeOH and filtration.

$^1$H NMR (400 MHz, DMSO) δ 11.96 (s, NH), 8.44 (d, J=5.2 Hz, 1H), 8.31 (s, 1H), 8.28 (d, J=8.4 Hz, 1H), 8.24 (d, J=16.2 Hz, 1H), 7.87-7.80 (m, 2H), 7.74-7.66 (m, 2H), 7.65-7.55 (m, 4H), 7.41 (d, J=5.2 Hz, 1H), 7.03 (d, J=8.8 Hz, 2H), 3.21-3.14 (m, 4H), 2.48-2.44 (m, 4H), 2.23 (s, 3H); $^{13}$C NMR (101 MHz, DMSO) δ 152.9 (C), 149.9 (C), 146.3 (CH), 139.4 (C), 138.1 (C), 134.9 (d, J=1.6 Hz, C), 133.2 (CH), 132.3 (C), 131.6 (C), 129.2 (CH), 129.1 (q, J=2.8 Hz, CH), 128.8 (CH), 128.2 (CH), 127.3 (CH), 126.4 (q, J=29.2 Hz, C), 126.1 (q, J=6.1 Hz, CH), 125.4 (CH), 124.4 (q, J=274.2 Hz, C), 120.7 (C), 120.3 (CH), 115.7 (CH), 112.6 (C), 111.7 (CH), 111.4 (CH), 54.6 (CH$_2$), 48.0 (CH$_2$), 45.8 (CH$_3$); HRMS calcd for $C_{31}H_{28}F_3N_4O$ [M+H]$^+$ 513.2261 found 513.2273.

Example 12

4-[4-(4-Chloro-3-methyl-phenoxymethyl)-phenyl]-6-[4-(4-methylpiperazin-1-yl)-phenyl]-9H-pyrido[2,3-b]indole (R522)

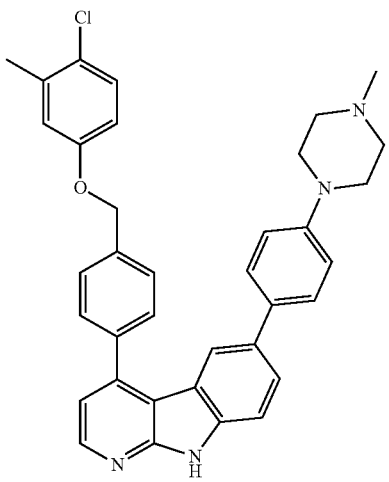 [SMILES: Cc1cc(OCc2ccc(-c3ccnc4[nH]c5ccc(-c6ccc(N7CCN(C)CC7)cc6)cc5c34)cc2)ccc1Cl]

The trituration procedure in MeOH afforded the desired compound in 66% yield as a yellow solid. $^1$H-NMR (400 MHz, DMSO) δ=12.00 (s, 1H), 8.46 (d, J=5.0 Hz, 1H), 7.77 (d, J=8.0 Hz, 2H), 7.73-7.67 (m, 3H), 7.65 (dd, J=8.7, 1.2 Hz, 1H), 7.55 (d, J=8.4 Hz, 1H), 7.34-7.27 (m, 3H), 7.13 (d, J=5.0 Hz, 1H), 7.10 (d, J=2.9 Hz, 1H), 6.93 (m, 3H), 5.25 (s, 2H), 3.16-3.08 (m, 4H), 2.47-2.40 (m, 4H), 2.30 (s, 3H), 2.22 (s, 3H). $^{13}$C-NMR (101 MHz, DMSO) δ=157.16 (Cq), 152.75 (Cq), 149.77 (Cq), 146.19 (CH), 144.03 (Cq), 138.01 (Cq), 137.95 (Cq), 137.65 (Cq), 136.58 (Cq), 131.61 (Cq), 131.37 (Cq), 129.52 (2 CH), 128.80 (2 CH), 127.99 (2 CH), 126.87 (2 CH), 125.20 (CH), 124.83 (Cq), 120.36 (Cq), 119.06 (CH), 117.76 (2 CH), 115.68 (2 CH), 113.92 (CH), 112.35 (Cq), 69.25 (CH$_2$), 54.60 (2 CH$_2$), 47.98 (2 CH$_2$), 45.80 (CH$_3$), 19.84 (CH$_3$). HRMS (ESI): calcd. for $C_{36}H_{34}ClN_4O$: 573.2416. found: 573.2424.

Example 13

(E)-4-(2-(4-Fluorophenyl)vinyl)-6-(4-(4-methylpiperazin-1-yl)phenyl)-9H-pyrido[2,3-b]indole (R527)

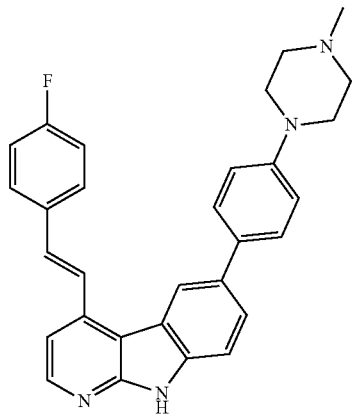 [SMILES: CN1CCN(c2ccc(-c3ccc4[nH]c5nccc(/C=C/c6ccc(F)cc6)c5c4c3)cc2)CC1]

A yellow solid was obtained in 74% yield after trituration of the crude product in MeOH and filtration. $^1$H NMR (300 MHz, DMSO) δ 11.88 (s, NH), 8.39 (d, J=5.2 Hz, 1H), 8.35 (s, 1H), 8.11 (d, J=16.3 Hz, 1H), 7.90 (dd, J=8.7, 5.7 Hz, 2H), 7.70 (dd, J=8.5, 1.6 Hz, 1H), 7.62 (d, J=16.1 Hz, 1H), 7.62 (d, J=8.8 Hz, 2H), 7.56 (d, J=8.4 Hz, 1H), 7.47 (d, J=5.2 Hz, 1H), 7.33 (t, J=8.9 Hz, 2H), 7.05 (d, J=8.8 Hz, 2H), 3.24-3.14 (m, 4H), 2.49-2.44 (m, 4H), 2.24 (s, 3H); $^{13}$C NMR (126 MHz, DMSO) δ 162.3 (d, J=246.4 Hz, C), 153.0 (C), 149.8 (C), 145.9 (CH), 140.2 (C), 138.0 (C), 133.4 (CH), 133.1 (d, J=3.0 Hz, C), 132.2 (C), 131.7 (C), 129.3 (d, J=8.3 Hz, CH), 127.3 (CH), 125.1 (CH), 124.1 (d, J=2.3 Hz, CH), 121.0 (C), 120.3 (CH), 115.9 (d, J=21.7 Hz, CH), 115.8 (CH), 112.4 (C), 111.5 (CH), 111.3 (CH), 54.6 (CH$_2$), 48.1 (CH$_2$), 45.8 (CH$_3$); HRMS calcd for $C_{30}H_{28}FN_4$ [M+H]$^+$ 463.2293 found 463.2282.

Example 14

(E)-6-(4-(4-Methylpiperazin-1-yl)phenyl)-4-(2-(4-(trifluoromethyl)phenyl)vinyl)-9H-pyrido[2,3-b]indole (R528)

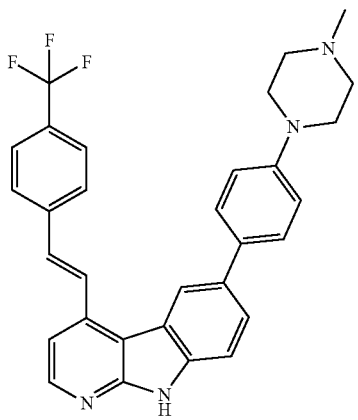 [SMILES: CN1CCN(c2ccc(-c3ccc4[nH]c5nccc(/C=C/c6ccc(C(F)(F)F)cc6)c5c4c3)cc2)CC1]

A brown solid was obtained in 83% yield after trituration of the crude product in MeOH and filtration. $^1$H NMR (500 MHz, DMSO) δ 11.92 (s, NH), 8.42 (d, J=5.1 Hz, 1H), 8.36 (s, 1H), 8.31 (d, J=16.3 Hz, 1H), 8.05 (d, J=8.0 Hz, 2H), 7.83 (d, J=8.1 Hz, 2H), 7.71 (d, J=15.9 Hz, 1H), 7.71 (d, J=8.7 Hz, 1H), 7.62 (d, J=8.7 Hz, 2H), 7.57 (d, J=8.4 Hz, 1H), 7.52 (d, J=5.2 Hz, 1H), 7.05 (d, J=8.7 Hz, 2H), 3.22-3.15 (m, 4H), 2.49-2.45 (m, 4H), 2.23 (s, 3H); $^{13}$C NMR (126 MHz, DMSO) δ 153.0 (C), 149.8 (C), 146.0 (CH), 140.5 (C), 139.6 (C), 138.1 (C), 133.0 (CH), 132.3 (C), 131.6 (C), 128.4 (q, J=31.3 Hz, C), 127.9 (CH), 127.3 (CH), 127.0 (CH), 125.8 (q, J=3.5 Hz, CH), 125.3 (CH), 124.3 (q, J=271.8 Hz, C), 120.8 (C), 120.4 (CH), 115.8 (CH), 112.6 (C), 111.6 (q, J=10.0 Hz, CH), 54.6 (CH$_2$), 48.0 (CH$_2$), 45.8 (CH$_3$); HRMS calcd for $C_{31}H_{28}F_3N_4O$ [M+H]$^+$ 513.2261 found 513.2248.

Example 15

4-(3-Fluoro-biphenyl-4-yl)-6-[4-(4-methylpiperazin-1-yl)-phenyl]-9H-pyrido[2,3-b]indole (R532)

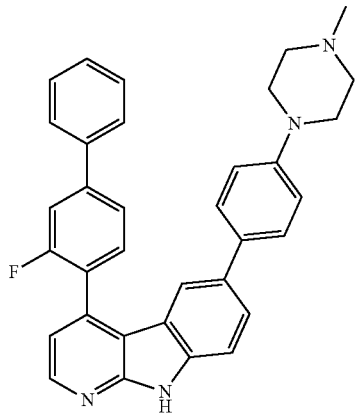 [SMILES: CN1CCN(c2ccc(-c3ccc4[nH]c5nccc(-c6ccc(-c7ccccc7)cc6F)c5c4c3)cc2)CC1]

The trituration procedure in MeOH afforded the desired compound in 89% yield as a dark yellow solid. $^1$H-NMR (400 MHz, DMSO) δ=12.06 (s, 1H), 8.50 (d, J=5.0 Hz, 1H), 7.84-7.76 (m, 2H), 7.76-7.65 (m, 4H), 7.65-7.52 (m, 3H), 7.52-7.41 (m, 2H), 7.36 (d, J=8.7 Hz, 2H), 7.21 (d, J=5.0 Hz, 1H), 6.95 (d, J=8.8 Hz, 2H), 3.16-3.09 (m, 4H), 2.46-2.39 (m, 4H), 2.20 (s, 3H). $^{13}$C-NMR (101 MHz, DMSO) δ=159.17 (d, J=247.4 Hz, Cq), 152.78 (Cq), 149.84 (Cq), 146.29 (CH), 142.50 (Cq), 139.84 (Cq), 139.72 (d, J=8.0 Hz, Cq) 138.11 (Cq), 134.66 (Cq), 131.77 (Cq), 131.31 (Cq), 131.17 (d, J=3.9 Hz, CH), 128.96 (CH), 128.93 (CH), 128.86 (2 CH), 128.79 (CH), 128.76 (CH), 128.74 (CH), 128.25 (2 CH), 126.87 (CH), 125.39 (d, J=5.7 Hz, CH), 120.16 (Cq), 119.04 (CH), 115.73 (CH), 115.69 (CH), 112.23 (Cq), 111.88 (CH), 54.58 (2 CH$_2$), 47.93 (2 CH$_2$), 45.78 (CH$_3$). HRMS (ESI): calcd. for $C_{34}H_{30}FN_4$: 513.2449. found: 513.2435

Example 16

4-(4-Benzylphenyl)-6-[4-(4-methylpiperazin-1-yl)-phenyl]-9H-pyrido[2,3-b]indole (R533)

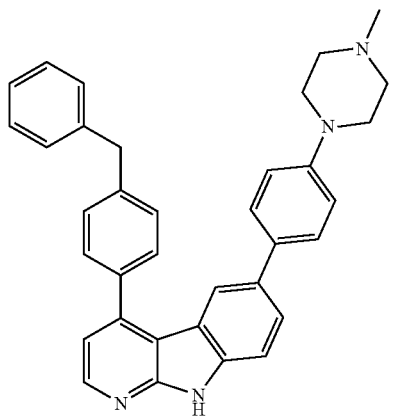 [SMILES: CN1CCN(c2ccc(-c3ccc4[nH]c5nccc(-c6ccc(Cc7ccccc7)cc6)c5c4c3)cc2)CC1]

The trituration procedure in MeOH afforded the desired compound in 78% yield as a yellow solid. $^1$H-NMR (400 MHz, DMSO) δ=11.95 (s, 1H), 8.43 (d, J=5.0 Hz, 1H), 7.71 (s, 1H), 7.68-7.62 (m, 3H), 7.53 (d, J=8.5 Hz, 1H), 7.50 (d, J=8.0 Hz, 2H), 7.35-7.25 (m, 6H), 7.24-7.18 (m, 1H), 7.09 (d, J=5.0 Hz, 1H), 6.91 (d, J=8.7 Hz, 2H), 4.09 (s, 2H), 3.20-3.12 (m, 4H), 2.49-2.43 (m, 4H), 2.23 (s, 3H). $^{13}$C-NMR (101 MHz, DMSO) δ=152.75 (Cq), 149.67 (Cq), 146.13 (CH), 144.30 (Cq), 142.04 (Cq), 141.28 (Cq), 137.96 (Cq), 136.06 (Cq), 131.37 (Cq), 131.23 (Cq), 129.13 (2 CH), 128.73 (3 CH), 128.51 (3 CH), 126.68 (2 CH), 125.97 (CH), 124.93 (CH), 120.44 (Cq), 119.03 (CH), 115.72 (CH), 115.66 (2 CH), 112.40 (Cq), 111.65 (CH), 54.59 (2 CH$_2$), 48.01 (2 CH$_2$), 45.79 (CH$_3$), 40.92 (CH$_2$). HRMS (ESI): calcd. for $C_{35}H_{33}N_4$: 509.2700. found: 509.2688.

Example 17

4-Biphenyl-3-yl-6-[4-(4-methylpiperazin-1-yl)-phenyl]-9H-pyrido[2,3-b]indole (R534)

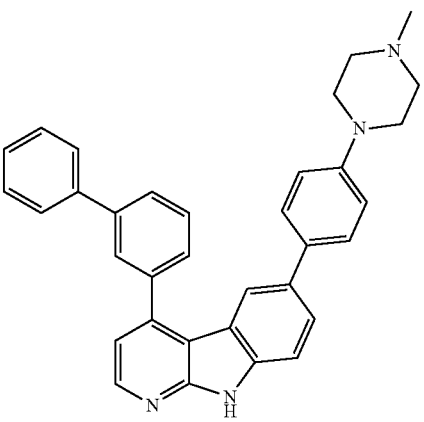 [SMILES: CN1CCN(c2ccc(-c3ccc4[nH]c5nccc(-c6cccc(-c7ccccc7)c6)c5c4c3)cc2)CC1]

The trituration procedure in MeOH afforded the desired compound in 60% yield as a beige solid. $^1$H-NMR (400 MHz, DMSO) δ=12.01 (s, 1H), 8.49 (d, J=5.0 Hz, 1H), 8.09

(d, J=1.6 Hz, 1H), 7.91-7.85 (m, 1H), 7.81-7.75 (m, 3H), 7.73 (m, 2H), 7.62 (dd, J=8.5, 1.6 Hz, 1H), 7.55 (d, J=8.4 Hz, 1H), 7.52-7.46 (m, 2H), 7.41 (m, 1H), 7.24 (d, J=5.0 Hz, 1H), 7.12 (d, J=8.7 Hz, 2H), 6.78 (d, J=8.8 Hz, 2H), 3.15-3.02 (m, 4H), 2.47-2.39 (m, 4H), 2.21 (s, 3H). $^{13}$C-NMR (101 MHz, DMSO) δ=152.86 (Cq), 149.67 (Cq), 146.32 (CH), 144.13 (Cq), 140.63 (Cq), 139.79 (Cq), 138.87 (Cq), 138.06 (Cq), 131.59 (Cq), 131.16 (Cq), 129.71 (CH), 129.07 (2 CH), 127.83 (CH), 127.67 (CH), 127.36 (CH), 127.19 (CH), 126.96 (2 CH), 126.76 (2 CH), 125.12 (CH), 120.36 (Cq), 119.17 (CH), 115.80 (CH), 115.59 (2 CH), 112.31 (Cq), 111.77 (CH), 54.55 (2 CH$_2$), 47.96 (2 CH$_2$), 45.78 (CH$_3$). HRMS (ESI): calcd. for $C_{34}H_{31}N_4$: 495.2543. found: 495.2540.

Example 18

(E)-4-(2-(2-Fluorophenyl)vinyl)-6-(4-(4-methylpiperazin-1-yl)phenyl)-9H-pyrido[2,3-b]indole (R542)

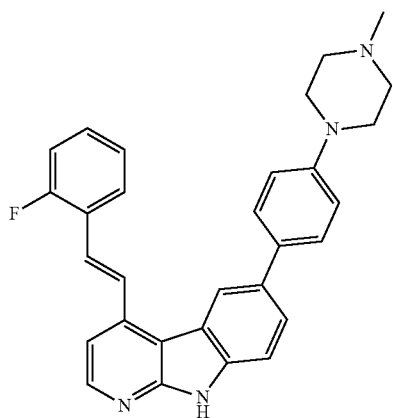 [SMILES: CN1CCN(c2ccc(-c3ccc4[nH]c5nccc(/C=C/c6ccccc6F)c5c4c3)cc2)CC1]

A yellow solid was obtained in 74% yield after trituration of the crude product in MeOH and filtration. $^1$H NMR (300 MHz, DMSO) δ 11.93 (s, NH), 8.41 (d, J=5.2 Hz, 1H), 8.34 (s, 1H), 8.28 (d, J=16.4 Hz, 1H), 7.97 (t, J=7.7 Hz, 1H), 7.71 (dd, J=8.5, 1.1 Hz, 1H), 7.65 (d, J=16.6 Hz, 1H), 7.62-7.51 (m, 4H), 7.47-7.40 (m, 1H), 7.40-7.30 (m, 2H), 7.05 (d, J=8.7 Hz, 2H), 3.22-3.14 (m, 4H), 2.48-2.43 (m, 4H), 2.23 (s, 3H); $^{13}$C NMR (101 MHz, DMSO) δ 160.4 (d, J=249.5 Hz, C), 153.0 (C), 149.9 (C), 146.1 (CH), 139.8 (C), 138.1 (C), 132.3 (C), 131.6 (C), 130.4 (d, J=8.6 Hz, CH), 129.4 (d, J=3.5 Hz, CH), 127.3 (d, J=7.5 Hz, CH), 127.2 (CH), 125.2 (CH), 125.1 (d, J=2.9 Hz, CH), 124.0 (d, J=11.2 Hz, C), 120.9 (C), 120.0 (CH), 116.2 (d, J=21.4 Hz), 115.8 (CH), 112.5 (C), 111.7 (CH), 111.1 (CH), 54.6 (CH$_2$), 48.0 (CH$_2$), 45.8 (CH$_3$); HRMS calcd for $C_{30}H_{28}FN_4$ [M+H]$^+$ 463.2293 found 463.2275.

Example 19

(E)-4-(2-(2-Chlorophenyl)vinyl)-6-(4-(4-methylpiperazin-1-yl)phenyl)-9H-pyrido[2,3-b]indole (R543)

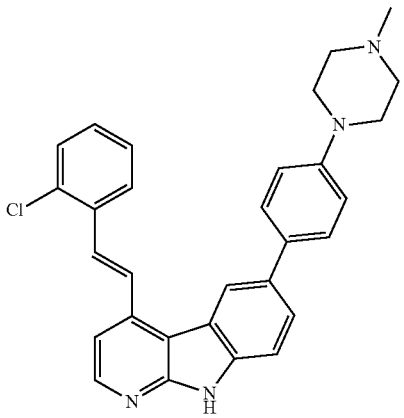 [SMILES: CN1CCN(c2ccc(-c3ccc4[nH]c5nccc(/C=C/c6ccccc6Cl)c5c4c3)cc2)CC1]

A yellow solid was obtained in 77% yield after trituration of the crude product in MeOH and filtration. $^1$H NMR (400 MHz, DMSO) δ 11.95 (s, NH), 8.42 (d, J=5.2 Hz, 1H), 8.34 (s, 1H), 8.24 (d, J=16.2 Hz, 1H), 8.15 (dd, J=7.8, 1.3 Hz, 1H), 7.78 (d, J=16.1 Hz, 1H), 7.70 (dd, J=8.4, 1.4 Hz, 1H), 7.62-7.54 (m, 4H), 7.53-7.46 (m, 2H), 7.42 (td, J=7.8, 1.4 Hz, 1H), 7.03 (d, J=8.8 Hz, 2H), 3.20-3.14 (m, 4H), 2.48-2.44 (m, 4H), 2.23 (s, 3H); $^{13}$C NMR (101 MHz, DMSO) δ 153.0 (C), 149.9 (C), 146.2 (CH), 139.7 (C), 138.1 (C), 134.1 (C), 132.7 (C), 132.3 (C), 131.6 (C), 130.2 (CH), 130.0 (CH), 129.9 (CH), 128.1 (CH), 127.9 (CH), 127.8 (CH), 127.3 (CH), 125.3 (CH), 120.8 (C), 120.3 (CH), 115.7 (CH), 112.6 (C), 111.7 (CH), 111.6 (CH), 54.6 (CH$_2$), 48.0 (CH$_2$), 45.8 (CH$_3$); HRMS calcd for $C_{30}H_{28}ClN_4$ [M+H]$^+$ 479.1997 found 479.1983.

Example 20

4,6-Bis-[4-(4-methylpiperazin-1-yl)-phenyl]-9H-pyrido[2,3-b]indole (R556)

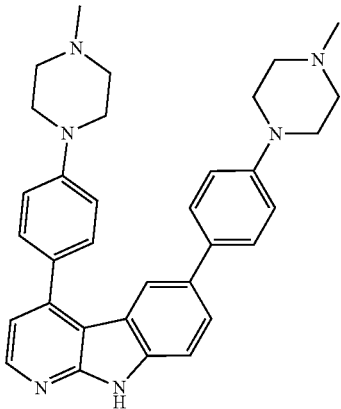 [SMILES: CN1CCN(c2ccc(-c3ccc4[nH]c5nccc(-c6ccc(N7CCN(C)CC7)cc6)c5c4c3)cc2)CC1]

The trituration procedure afforded the desired compound in 76% yield as a yellow solid. $^1$H-NMR (300 MHz, DMSO) δ=11.90 (s, 1H), 8.39 (d, J=5.0 Hz, 1H), 7.89 (d, J=1.2 Hz, 1H), 7.64 (dd, J=8.2, 1.7 Hz, 1H), 7.62 (d, J=8.5 Hz, 2H), 7.53 (d, J=8.4 Hz, 1H), 7.36 (d, J=8.7 Hz, 2H), 7.17 (d, J=8.8 Hz, 2H), 7.06 (d, J=5.0 Hz, 1H), 6.97 (d, J=8.8 Hz, 2H), 3.33-3.26 (m, 8H), 3.20-3.09 (m, 4H), 2.47-2.41 (m, 4H), 2.24 (s, 3H), 2.22 (s, 3H). $^{13}$C-NMR (101 MHz, DMSO) δ=152.79 (Cq), 151.09 (Cq), 149.56 (Cq), 145.80 (CH), 144.45 (Cq), 137.76 (Cq), 131.38 (Cq), 131.29 (Cq), 129.20 (2 CH), 127.87 (Cq), 126.70 (2 CH), 124.61 (CH), 120.59 (Cq), 119.06 (CH), 115.50 (2 CH), 115.45 (CH), 114.71 (2 CH), 112.21 (Cq), 111.30 (CH), 54.39 (2 CH$_2$), 54.26 (2 CH$_2$), 47.88 (2 CH$_2$), 47.58 (2 CH$_2$), 45.55 (CH$_3$), 45.53 (CH$_3$). HRMS (ESI): calcd. for C$_{33}$H$_{37}$N$_6$: 517.3074. found: 517.3058.

Example 21

4-(4-Benzylphenyl)-6-(4-(4-(1-methylpiperidin-4-yl)piperazin-1-yl)phenyl)-9H-pyrido[2,3-b]indole (R559)

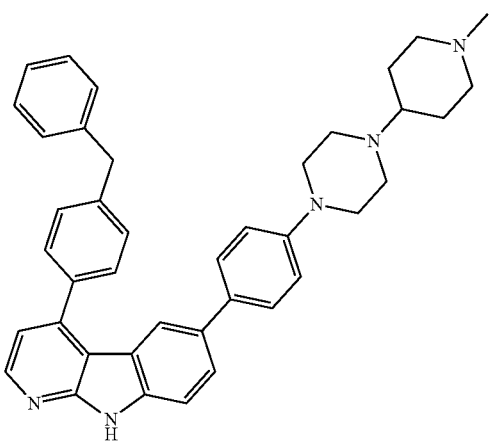 [SMILES: CN1CCC(N2CCN(c3ccc(-c4ccc5[nH]c6nccc(-c7ccc(Cc8ccccc8)cc7)c6c5c4)cc3)CC2)CC1]

A white solid was obtained in 77% yield after trituration of the crude product in MeOH and filtration. $^1$H NMR (500 MHz, DMSO) δ 11.79 (s, 1H), 8.43 (d, J=5.0 Hz, 1H), 7.70 (s, 1H), 7.65 (d, J=7.9 Hz, 3H), 7.54 (d, J=8.5 Hz, 1H), 7.50 (d, J=7.8 Hz, 2H), 7.36-7.26 (m, J=17.6, 7.7 Hz, 6H), 7.22 (t, J=6.5 Hz, 1H), 7.08 (d, J=4.9 Hz, 1H), 6.90 (d, J=8.6 Hz, 2H), 4.11 (s, 2H), 3.21-3.17 (m, 4H), 2.81 (d, J=11.4 Hz, 2H), 2.71-2.61 (m, 4H), 2.17 (s, 4H), 1.91 (t, J=11.2 Hz, 2H), 1.77 (d, J=11.6 Hz, 2H), 1.48 (ddd, J=14.6, 11.9, 3.1 Hz, 2H); $^{13}$C NMR (126 MHz, DMSO) δ 152.6 (C), 149.5 (C), 145.8 (CH), 144.1 (C), 141.7 (C), 140.9 (C), 137.8 (C), 135.9 (C), 131.2 (C), 131.0 (C), 128.8 (CH), 128.4 (CH), 128.4 (CH), 128.2 (CH), 126.4 (CH), 125.7 (CH), 124.6 (CH), 120.3 (C), 118.8 (CH), 115.4 (CH), 115.3 (CH), 112.3 (C), 111.3 (CH), 60.4 (CH), 54.5 (2CH$_2$), 48.5 (2CH$_2$), 48.4 (2CH$_2$), 45.5 (NCH$_3$), 40.7 (CH$_2$), 27.7 (2CH$_2$); HRMS calcd for C$_{40}$H$_{42}$N$_5$ [M+H]$^+$ 592.3435 found 592.3418.

Example 22

(E)-6-(4-(4-(1-Methylpiperidin-4-yl)piperazin-1-yl)phenyl)-4-(2-(2-(trifluoromethyl)phenyl)vinyl)-9H-pyrido[2,3-b]indole (R566)

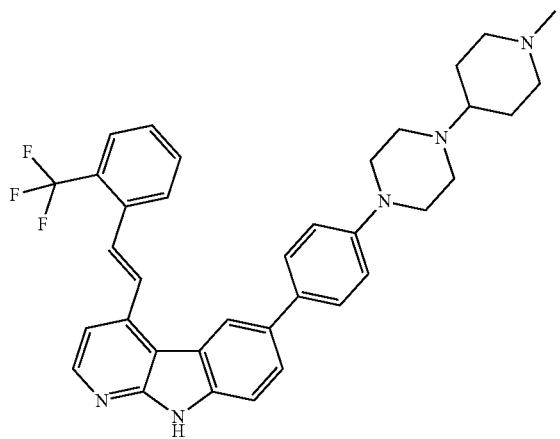 [SMILES: CN1CCC(N2CCN(c3ccc(-c4ccc5[nH]c6nccc(/C=C/c7ccccc7C(F)(F)F)c6c5c4)cc3)CC2)CC1]

A yellow solid was obtained in 73% yield after trituration of the crude product in MeOH and filtration. $^1$H NMR (500 MHz, DMSO) δ 11.62 (s, 1H), 8.43 (d, J=5.1 Hz, 1H), 8.31 (d, J=1.2 Hz, 1H), 8.18 (d, J=8.0 Hz, 1H), 8.12 (d, J=16.0 Hz, 1H), 7.84-7.79 (m, 2H), 7.73 (dd, J=16.2, 1.9 Hz, 1H), 7.70 (dd, J=8.5, 1.6 Hz, 1H), 7.63-7.58 (m, 2H), 7.56 (d, J=8.7 Hz, 2H), 7.37 (d, J=5.2 Hz, 1H), 7.00 (d, J=8.7 Hz, 2H), 3.23-3.16 (m, 4H), 2.80 (d, J=11.7 Hz, 2H), 2.69-2.63 (m, 4H), 2.22 (dt, 1H), 2.17 (s, 3H), 1.92 (td, J=11.6, 2.0 Hz, 2H), 1.76 (d, J=12.0 Hz, 2H), 1.49 (ddd, J=15.1, 11.9, 3.6 Hz, 2H); $^{13}$C NMR (126 MHz, DMSO) δ 152.7 (C), 149.5 (C), 145.7 (CH), 139.0 (C), 137.8 (C), 134.7 (d, J=1.6 Hz, C), 132.4 (CH), 132.1 (C), 131.2 (C), 128.9 (d, J=2.1 Hz, CH), 128.9 (CH), 128.2 (CH), 127.7 (CH), 126.7 (CH), 126.2 (q, J=29.1 Hz, C), 125.6 (q, J=5.3 Hz, CH), 124.8 (CH), 124.0 (q, J=274.0 Hz, C), 120.5 (C), 119.6 (CH), 115.2 (CH), 112.3 (C), 111.2 (CH), 111.1 (CH), 60.3 (CH), 54.3 (2CH$_2$), 48.3 (2CH$_2$), 48.3 (2CH$_2$), 45.2 (NCH$_3$), 27.6 (2CH$_2$); HRMS calcd for C$_{36}$H$_{37}$F$_3$N$_5$ [M+H]$^+$ 596.2996 found 596.2977.

Example 23

(4-{6-[4-(4-Methylpiperazin-1-yl)-phenyl]-9H-pyrido[2,3-b]indol-4-yl}-phenyl)-phenyl-methanone (R571)

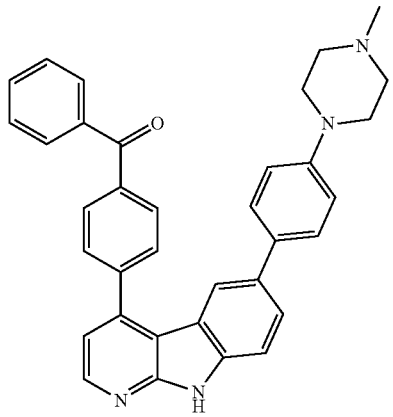 [SMILES: CN1CCN(c2ccc(-c3ccc4[nH]c5nccc(-c6ccc(C(=O)c7ccccc7)cc6)c5c4c3)cc2)CC1]

The trituration procedure afforded the desired compound in 54% yield as a yellow solid. $^1$H-NMR (300 MHz, CDCl$_3$) δ=8.34 (d, J=5.1 Hz, 1H), 7.94 (d, J=8.1 Hz, 2H), 7.84-7.71 (m, 5H), 7.63-7.53 (m, 2H), 7.52-7.40 (m, 3H), 7.31 (d, J=8.6 Hz, 2H), 7.06 (d, J=5.1 Hz, 1H), 6.89 (d, J=8.7 Hz, 2H), 3.26-3.10 (m, 4H), 2.87-2.49 (m, 4H), 2.35 (s, 3H). $^{13}$C-NMR (75 MHz, CDCl$_3$) δ=197.58 (CO), 152.79 (Cq), 150.16 (Cq), 145.49 (CH), 144.97 (Cq), 143.65 (Cq), 138.90 (Cq), 138.03 (Cq), 137.80 (Cq), 134.02 (Cq), 133.38 (CH), 133.33 (Cq), 130.96 (2 CH), 130.60 (2 CH), 129.30 (2 CH), 128.96 (2 CH), 128.01 (2 CH), 126.66 (CH), 121.09 (Cq), 120.62 (CH), 117.13 (2 CH), 116.37 (CH), 114.52 (Cq), 112.11 (CH), 55.22 (2 CH$_2$), 49.57 (2 CH$_2$), 45.95 (CH$_3$). HRMS (ESI): calcd. for C$_{35}$H$_{31}$N$_4$O: 523.2492. found: 523.2490.

Example 24

6-[4-(4-Methylpiperazin-1-yl)-phenyl]-4-(4-naphthalen-1-yl-phenyl)-9H-pyrido[2,3-b]indole (R590)

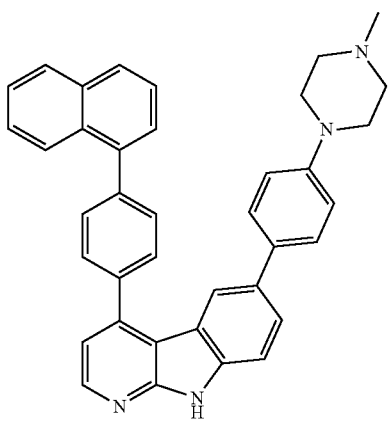 [SMILES: CN1CCN(c2ccc(-c3ccc4[nH]c5nccc(-c6ccc(-c7cccc8ccccc78)cc6)c5c4c3)cc2)CC1]

The compound was purified by silica gel flash chromatography (CH$_2$Cl$_2$/MeOH 99:1 gradient to 95:5) in 40% yield as a yellow solid. $^1$H-NMR (400 MHz, CDCl$_3$) δ=8.14 (d, J=5.1 Hz, 1H), 7.75-7.62 (m, 4H), 7.56 (d, J=8.0 Hz, 2H), 7.46-7.39 (m, 3H), 7.34-7.22 (m, 3H), 7.19-7.11 (m, 3H), 6.94 (d, J=5.1 Hz, 1H), 6.67 (d, J=8.7 Hz, 2H), 3.00-2.90 (m, 4H), 2.42-2.34 (m, 4H), 2.11 (s, 3H). $^{13}$C-NMR (101 MHz, CDCl$_3$) δ=152.00 (Cq), 149.22 (Cq), 145.45 (Cq), 144.55 (CH), 141.05 (Cq), 139.29 (Cq), 138.05 (Cq), 137.38 (Cq), 133.63 (Cq), 133.32 (Cq), 132.27 (Cq), 131.27 (Cq), 130.00 (2 CH), 128.30 (2 CH), 128.04 (CH), 127.62 (CH), 127.09 (2 CH), 126.68 (CH), 125.97 (CH), 125.44 (2 CH), 125.38 (CH), 125.04 (CH), 120.69 (Cq), 119.99 (CH), 116.39 (2 CH), 115.73 (CH), 114.17 (Cq), 111.16 (CH), 54.40 (2 CH$_2$), 48.42 (2 CH$_2$), 45.06 (CH$_3$). HRMS (ESI): calcd. for C$_{38}$H$_{33}$N$_4$: 545.2700. found: 545.2690.

Example 25

(E)-4-(1,2-Diphenylvinyl)-6-[4-(4-methylpiperazin-1-yl)-phenyl]-9H-pyrido[2,3-b]indole (R593)

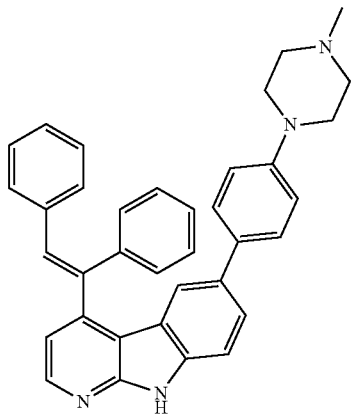 [SMILES: CN1CCN(c2ccc(-c3ccc4[nH]c5nccc(/C(=C/c6ccccc6)c6ccccc6)c5c4c3)cc2)CC1]

The crude product was purified by silica gel flash column chromatography (DCM/MeOH 97:3 to 90:10) to afford the desired product in 74% yield as a yellow solid. $^1$H NMR (400 MHz, CDCl$_3$) δ 11.33 (s, NH), 8.48 (d, J=5.1 Hz, 1H), 8.35 (d, J=1.4 Hz, 1H), 7.67 (dd, J=8.4, 1.7 Hz, 1H), 7.58 (d, J=8.4 Hz, 1H), 7.39-7.33 (m, 2H), 7.33-7.26 (m, 10H), 7.20 (s, 1H), 7.01 (d, J=5.1 Hz, 1H), 6.83 (d, J=8.8 Hz, 2H), 3.25-3.18 (m, 4H), 2.64-2.57 (m, 4H), 2.38 (s, 3H); $^{13}$C NMR (101 MHz, CDCl$_3$) δ 153.5 (C), 145.0 (C), 148.2 (C), 145.1 (CH), 139.2 (C), 139.0 (C), 138.2 (C), 136.8 (C), 133.1 (C), 132.8 (C), 132.6 (CH), 130.2 (CH), 129.8 (CH), 128.7 (CH), 128.5 (CH), 128.1 (CH), 127.7 (CH), 127.7 (CH), 125.6 (CH), 121.6 (C), 121.1 (CH), 116.9 (CH), 116.3 (CH), 114.8 (C), 111.4 (CH), 55.2 (CH$_2$), 49.1 (CH$_2$), 46.2 (CH$_3$); HRMS calcd for C$_{36}$H$_{33}$N$_4$ [M+H]$^+$ 521.2700 found 521.2690.

Example 26

4-[4-(2,4-Dimethoxybenzyl)phenyl]-6-[4-(4-methylpiperazin-1-yl)-phenyl]-9H-pyrido[2,3-b]indole (R596)

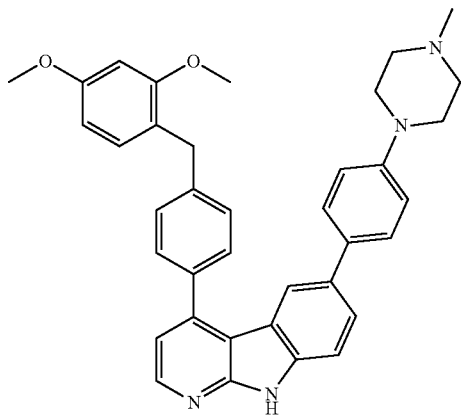 [SMILES: COc1ccc(Cc2ccc(-c3ccnc4[nH]c5ccc(-c6ccc(N7CCN(C)CC7)cc6)cc5c34)cc2)c(OC)c1]

The trituration procedure afforded the desired compound in 70% yield as a yellow solid. $^1$H-NMR (300 MHz, CDCl$_3$) δ=9.58 (s, 1H), 8.48 (d, J=5.1 Hz, 1H), 7.99-7.90 (m, 1H), 7.71-7.60 (m, 3H), 7.53 (d, J=8.4 Hz, 1H), 7.40 (d, J=8.4 Hz, 4H), 7.11 (d, J=5.1 Hz, 1H), 7.05 (d, J=8.2 Hz, 1H), 6.95 (d, J=8.7 Hz, 2H), 6.51 (d, J=2.3 Hz, 1H), 6.44 (dd, J=8.3, 2.4 Hz, 1H), 4.03 (s, 2H), 3.81 (s, 6H), 3.40-3.24 (m, 4H), 2.81-2.62 (m, 4H), 2.44 (s, 3H). $^{13}$C-NMR (75 MHz, CDCl$_3$) δ=159.62 (Cq), 158.37 (Cq), 153.07 (Cq), 149.71 (Cq), 146.01 (Cq), 145.44 (CH), 142.39 (Cq), 137.93 (Cq), 136.28 (Cq), 133.45 (Cq), 132.67 (Cq), 130.63 (CH), 129.28 (2 CH), 128.82 (2 CH), 127.69 (2 CH), 125.78 (CH), 122.08 (Cq), 121.53 (Cq), 120.67 (CH), 116.75 (CH), 116.61 (2 CH), 114.17 (Cq), 111.37 (CH), 104.31 (CH), 98.69 (CH), 55.56 (CH$_3$), 55.54 (CH$_3$), 54.99 (2 CH$_2$), 48.80 (2 CH$_2$), 45.88 (CH$_3$), 35.31 (CH$_2$). HRMS (ESI): calcd. for C$_{37}$H$_{37}$N$_4$O$_2$: 569.2911. found: 569.2912.

Example 27

(E)-4-[1-(2-Methoxyphenyl)-prop-1-en-2-yl]-6-[4-(4-methylpiperazin-1-yl)-phenyl]-9H-pyrido[2,3-b]indole (R604)

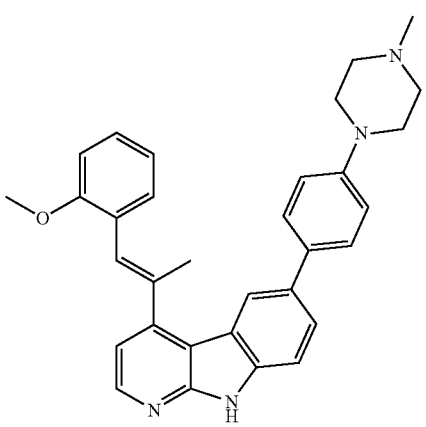 [SMILES: COc1ccccc1/C=C(\C)c1ccnc2[nH]c3ccc(-c4ccc(N5CCN(C)CC5)cc4)cc3c12]

A pale yellow solid was obtained in 46% yield after trituration of the crude product in MeOH and filtration. $^1$H NMR (400 MHz, CDCl$_3$) δ 11.01 (s, 1H), 8.58 (d, J=1.1 Hz, 1H), 8.51 (d, J=5.0 Hz, 1H), 7.70 (dd, J=8.4, 1.6 Hz, 1H), 7.59 (d, J=8.4 Hz, 1H), 7.55 (d, J=7.8 Hz, 1H), 7.52 (d, J=8.7 Hz, 2H), 7.36-7.30 (m, 1H), 7.15 (d, J=5.1 Hz, 1H), 7.09-7.02 (m, 2H), 6.96 (d, J=8.7 Hz, 2H), 6.92 (d, J=8.2 Hz, 1H), 3.61 (s, 3H), 3.34-3.20 (m, 4H), 2.65 (d, J=4.5 Hz, 4H), 2.41 (d, J=1.1 Hz, 3H), 2.40 (s, 3H); $^{13}$C NMR (101 MHz, CDCl$_3$) δ 157.7 (C), 153.4 (C), 150.1 (C), 149.7 (C), 145.3 (CH), 138.0 (C), 135.2 (C), 133.7 (C), 133.0 (C), 130.3 (CH), 128.7 (CH), 128.0 (CH), 126.8 (CH), 126.2 (C), 125.7 (CH), 121.7 (C), 121.4 (CH), 120.2 (CH), 116.5 (CH), 115.0 (CH), 113.6 (C), 111.3 (CH), 110.6 (CH), 55.2 (OCH$_3$), 55.2 (2CH$_2$), 49.3 (2CH$_2$), 46.2 (NCH$_3$), 19.1 (CH$_3$); HRMS calcd for C$_{32}$H$_{33}$N$_4$O [M+H]$^+$ 489.2649 found 489.2635.

Example 28

(E)-6-(4-(4-methylpiperazin-1-yl)phenyl)-4-(1-phenylprop-1-en-2-yl)-9H-pyrido[2,3-b]indole (R569)

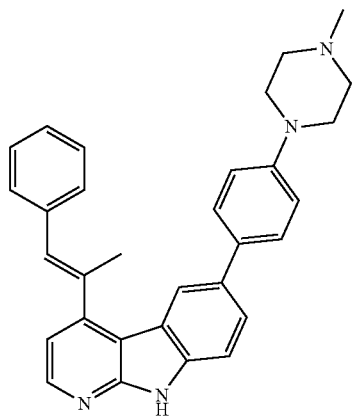 [SMILES: C/C(=C\c1ccccc1)c1ccnc2[nH]c3ccc(-c4ccc(N5CCN(C)CC5)cc4)cc3c12]

The crude residue was purified over silica gel flash chromatography (DCM/MeOH 98:2 to 95:5) and then triturated in MeOH to give only the desired regioisomer as a colourless amorphous solid in 64% yield. $^1$H NMR (400 MHz, CDCl$_3$) δ 10.48 (s, 1H), 8.50 (d, J=5.1 Hz, 1H), 8.36 (s, 1H), 7.70 (dd, J=8.4, 1.5 Hz, 1H), 7.58 (d, J=8.4 Hz, 1H), 7.55-7.41 (m, 6H), 7.33 (t, J=7.2 Hz, 1H), 7.12 (d, J=5.1 Hz, 1H), 6.95 (d, J=8.9 Hz, 2H), 6.94 (s, 1H), 3.29-3.21 (m, 4H), 2.65-2.56 (m, 4H), 2.48 (s, 3H), 2.38 (s, 3H); $^{13}$C NMR (101 MHz, CDCl$_3$) δ 153.24 (C), 150.20 (C), 149.55 (C), 145.62 (CH), 137.88 (C), 137.40 (C), 135.60 (C), 133.19 (C), 133.17 (C), 130.81 (CH), 129.26 (CH), 128.60 (CH), 127.84 (CH), 127.26 (CH), 125.74 (CH), 121.52 (C), 120.98 (CH), 116.41 (CH), 115.07 (CH), 113.47 (C), 111.42 (CH), 55.27 (CH$_2$), 49.22 (CH$_2$), 46.33 (NCH$_3$), 19.03 (CH$_3$); HRMS calcd for C$_{31}$H$_{31}$N$_4$ [M+H]$^+$ 459.2543 found 459.2522.

Example 29

N-[(E)-2-(2-{6-[4-(4-Methylpiperazin-1-yl)-phenyl]-9H-pyrido[2,3-b]indol-4-yl}-vinyl)-phenyl]-methanesulfonamide (R589)

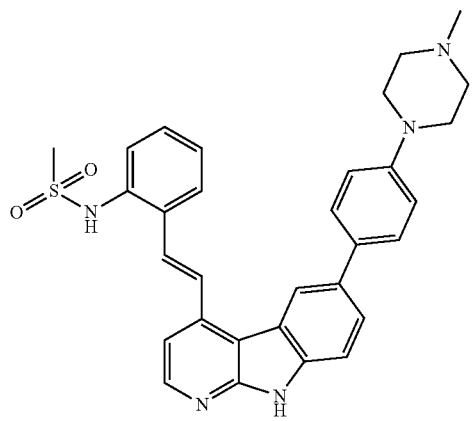 [SMILES: CN1CCN(c2ccc(-c3ccc4[nH]c5nccc(/C=C/c6ccccc6NS(C)(=O)=O)c5c4c3)cc2)CC1]

The trituration procedure afforded the desired compound in 43% yield as a yellow solid. $^1$H-NMR (300 MHz, CDCl$_3$/MeOD 7:2) δ=8.16 (d, J=5.2 Hz, 2H), 7.93-7.71 (m, 4H), 7.56-7.50 (m, 1H), 7.48-7.39 (m, 4H), 7.34 (m, 2H), 6.91 (d, J=8.6 Hz, 2H), 3.16-3.07 (m, 4H), 2.84 (s, 3H), 2.64-2.46 (m, 4H), 2.26 (s, 3H). HRMS (ESI): calcd. for C$_{31}$H$_{32}$N$_5$O$_2$S: 538.2271. found: 538.2270.

Example 30

(E)-6-[4-(4-Methylpiperazin-1-yl)-phenyl]-4-(1-phenyl-but-1-enyl)-9H-pyrido[2,3-b]indole (R594)

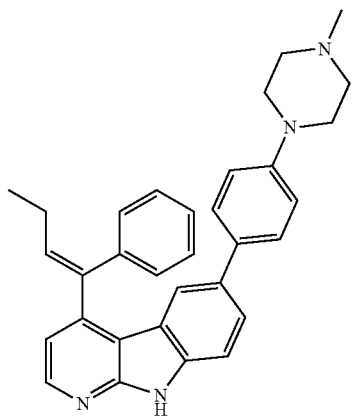 [SMILES: CC/C=C(\c1ccccc1)c1ccnc2[nH]c3ccc(-c4ccc(N5CCN(C)CC5)cc4)cc3c12]

Mixture A: 4,4,5,5-Tetramethyl-2-(1-phenyl-but-1-enyl)-[1,3,2]dioxaborolane and 2-(1-Benzylidene-propyl)-4,4,5,5-tetramethyl-[1,3,2]dioxaborolane

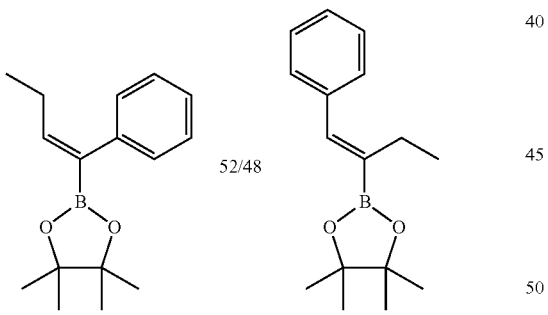

52/48

In a sealed tube, the aromatic alkyne (150 mg, 1 eq) and pinacol borane (2.5 eq) were introduced. The tube was stirred at 100° C. for 65 hrs. After cooling to room temperature, the reaction mixture was diluted with 20 mL of EtOAc. Then, the organic phase was washed with a 1/1 mixture of brine/water (2×20 mL), dried over MgSO$_4$, filtered, evaporated under vacuum. The oily crude residue was purified by silica gel column chromatography (PE/DCM 75:25) and afforded the 52:48 mixture of regioisomers as an uncolored oil in 80% yield. Major compound (extrapolated from the 52:48 mixture); $^1$H NMR (500 MHz, CDCl$_3$) δ 7.34-7.28 (m, 3H), 7.22-7.19 (m, 1H), 7.16-7.13 (m, 1H), 6.57 (t, J=7.3 Hz, 1H), 2.16 (p, J=7.5 Hz, 2H), 1.27 (s, 12H), 1.00 (t, J=7.5 Hz, 3H); $^{13}$C NMR (126 MHz, CDCl$_3$) δ 150.0 (CH), 140.3 (C), 129.1 (CH), 128.2 (CH), 126.0 (CH), 83.6 (C), 24.9 (CH$_3$), 22.8 (CH$_2$), 14.0 (CH$_3$); Minor compound (extrapolated from the 52:48 mixture); $^1$H NMR (500 MHz, CDCl$_3$) δ 7.34-7.28 (m, 3H), 7.26 (s, 1H), 7.22-7.19 (m, 1H), 7.16-7.13 (m, 1H), 2.39 (q, J=7.1 Hz, 2H), 1.32 (s, 12H), 1.10 (t, J=7.5 Hz, 3H); $^{13}$C NMR (126 MHz, CDCl$_3$) δ 141.5 (CH), 138.0 (C), 129.1 (CH), 127.9 (CH), 127.2 (CH), 83.5 (C), 24.9 (CH$_3$), 23.4 (CH$_2$), 14.8 (CH$_3$); MS (ESI) m/z: 259.0 [M+H]$^+$, 281.0 [M+Na]$^+$.

(E)-6-[4-(4-Methylpiperazin-1-yl)-phenyl]-4-(1-phenyl-but-1-enyl)-9H-pyrido[2,3-b]indole Mixture A above underwent typical procedure B. The crude product was purified by silica gel flash column chromatography (DCM/MeOH 97:3 to 90:10) to afford a mixture of regioisomers in 59% chemical yield as a white solid. Following deprotection as per typical procedure A, the pure regioisomer of interest was obtained after trituration of the white solid in MeOH and filtration.

$^1$H NMR (400 MHz, CDCl$_3$) δ 10.39 (s, 1H), 8.41 (d, J=5.1 Hz, 1H), 8.20 (d, J=1.4 Hz, 1H), 7.64 (dd, J=8.4, 1.7 Hz, 1H), 7.54 (d, J=8.4 Hz, 1H), 7.45 (d, J=8.7 Hz, 2H), 7.36 (d, J=4.3 Hz, 4H), 7.32-7.27 (m, 1H), 7.00 (d, J=8.8 Hz, 2H), 6.94 (d, J=5.1 Hz, 1H), 6.20 (t, J=7.5 Hz, 1H), 3.35-3.24 (m, 4H), 2.70-2.60 (m, 4H), 2.53 (p, J=7.5 Hz, 2H), 2.40 (s, 3H), 1.19 (t, J=7.5 Hz, 3H); $^{13}$C NMR (101 MHz, CDCl$_3$) δ 153.3 (s), 150.0 (s), 148.1 (s), 145.3 (CH), 139.1 (s), 138.1 (s), 137.8 (s), 136.1 (CH), 133.6 (s), 133.1 (s), 129.7 (CH), 128.4 (CH), 128.0 (CH), 127.5 (CH), 125.8 (CH), 121.7 (s), 121.3 (CH), 117.5 (CH), 116.4 (CH), 114.4 (s), 111.2 (CH), 55.2 (CH$_2$), 49.1 (CH$_2$), 46.2 (CH$_3$), 23.3 (CH$_2$), 14.5 (CH$_3$); HRMS calcd for C$_{32}$H$_{33}$N$_4$ [M+H]$^+$ 473.2700 found 473.2709.

Example 31

62:38 mixture of (E)-6-(4-(4-methylpiperazin-1-yl)phenyl)-4-(1-phenylbut-1-en-2-yl)-9H-pyrido[2,3-b]indole and (E)-6-(4-(4-methylpiperazin-1-yl)phenyl)-4-(1-phenylbut-1-en-1-yl)-9H-pyrido[2,3-b]indole (R595)

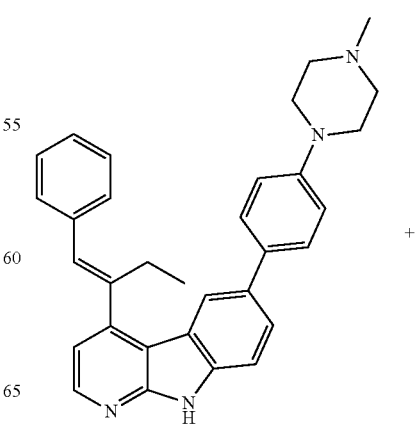

+

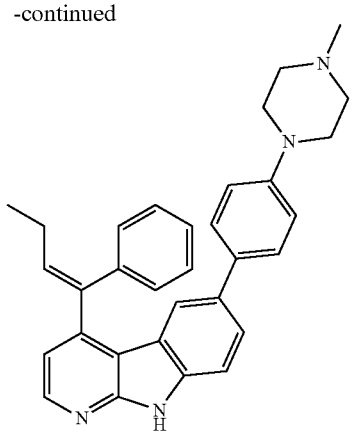

After trituration of mixture A in example 30 the MeOH phase was brought to dryness. $^1$H NMR (400 MHz, CDCl$_3$) δ 10.59 (s, 1.02H), 8.50 (d, J=5.1 Hz, 0.51H), 8.43-8.39 (m, 0.91H), 8.21 (d, J=1.4 Hz, 0.37H), 7.70 (dd, J=8.4, 1.8 Hz, 0.62H), 7.65 (dd, J=8.4, 1.8 Hz, 0.43H), 7.59 (d, J=8.4 Hz, 0.64H), 7.55 (d, J=8.3 Hz, 0.50H), 7.51-7.42 (m, 4.32H), 7.36 (d, J=4.4 Hz, 1.96H), 7.11 (d, J=5.1 Hz, 0.61H), 7.01 (d, J=8.9 Hz, 0.83H), 6.98-6.92 (m, 1.93H), 6.87 (s, 0.61H), 6.20 (t, J=7.5 Hz, 0.35H), 3.37-3.22 (m, 4.06H), 2.94 (q, J=7.5 Hz, 1.19H), 2.72-2.60 (m, 4.21H), 2.53 (qu, J=7.5 Hz, 0.82H), 2.41 (s, 3.15H), 1.19 (t, J=7.5 Hz, 1.19H), 1.08 (t, J=327.5 Hz, 1.80H).

The proportion 62/38 has been determined after averaging the integration ratio of signals at 1.11 ppm and 1.00 ppm (CH$_3$ protons); and also at 6.20 ppm and 6.87 ppm (vinylic protons). The regioisomeric composition was determined by $^1$H NMR.

Example 32

(E) and (Z)-6-(4-(4-methylpiperazin-1-yl)phenyl)-4-(2-(triisopropylsilyl)vinyl)-9H-pyrido[2,3-b]indole R(607)

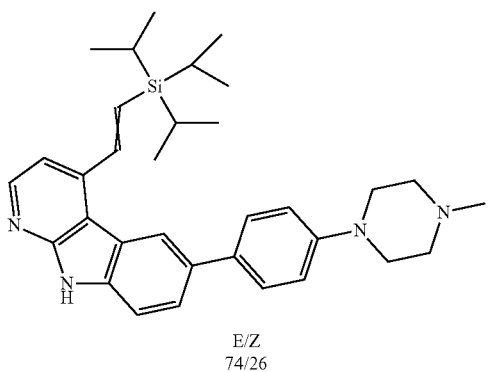 [SMILES: CC(C)[Si](C=Cc1ccnc2[nH]c3ccc(-c4ccc(N5CCN(C)CC5)cc4)cc3c12)(C(C)C)C(C)C]

E/Z
74/26

The crude product was purified by silica gel flash chromatography (DCM/MeOH 98:2 to 94:6) to afford in 45% yield the mixture of E/Z isomers in 74:26 ratio as a yellowish amorphous solid. Major compound (extrapolated from a 74:26 mixture)$^1$H NMR (300 MHz, CDCl$_3$) δ 10.92 (s, 1H), 8.49 (d, J=5.5 Hz, 1H), 8.35 (d, J=1.2 Hz, 1H), 7.99 (d, J=19.4 Hz, 1H), 7.72 (dd, J=8.5, 1.5 Hz, 1H), 7.64-7.55 (m, 3H), 7.36 (d, J=5.3 Hz, 1H), 7.04 (d, J=8.8 Hz, 2H), 6.85 (d, J=19.3 Hz, 1H), 3.38-3.23 (m, 4H), 2.75-2.59 (m, 4H), 2.42 (s, 3H), 1.38-1.26 (m, 3H), 1.20 (d, J=6.6 Hz, 18H); $^{13}$C NMR (101 MHz, CDCl$_3$) δ 153.5 (C), 150.1 (C), 145.4 (CH), 142.7 (C), 141.9 (CH), 138.1 (C), 133.4 (C), 133.4 (C), 132.6 (CH), 127.9 (CH), 125.7 (CH), 121.9 (C), 121.4 (CH), 116.5 (CH), 113.7 (C), 111.9 (CH), 111.6 (CH), 55.2 (2CH$_2$), 49.1 (2CH$_2$), 46.2 (NCH$_3$), 19.0 (6CH$_3$), 11.2 (3CH).

Minor compound (extrapolated from a 74:26 mixture)$^1$H NMR (300 MHz, CDCl$_3$) δ 10.92 (s, 1H), 8.47 (d, J=6.0 Hz, 1H), 8.27 (d, J=1.2 Hz, 1H), 8.07 (d, J=16.0 Hz, 1H), 7.69 (dd, J=7.2, 1.6 Hz, 1H), 7.64-7.55 (m, 3H), 7.13 (s, 1H), 7.05 (d, J=8.9 Hz, 2H), 6.24 (d, J=16.0 Hz, 1H), 3.41-3.21 (m, 4H), 2.77-2.58 (m, 4H), 2.42 (s, 3H), 1.11-1.00 (m, 3H), 0.96 (d, J=6.3 Hz, 18H); $^{13}$C NMR (101 MHz, CDCl$_3$) δ 152.6 (C), 150.1 (C), 145.0 (CH), 144.5 (C), 144.2 (CH), 137.9 (C), 133.6 (C), 133.6 (C), 132.2 (CH), 128.1 (CH), 125.9 (CH), 122.1 (C), 121.5 (CH), 116.5 (CH), 114.9 (CH), 114.3 (C), 111.3 (CH), 55.2 (2CH$_2$), 49.1 (2CH$_2$), 46.2 (NCH$_3$), 19.0 (6CH$_3$), 12.4 (3CH); HRMS calcd for C$_{33}$H$_{45}$N$_4$Si [M+H]$^+$ 525.3408 found 525.3390.

Example 33

(4-{6-[4-(4-Methylpiperazin-1-yl)-phenyl]-9H-pyrido[2,3-b]indol-4-yl}-phenyl)-phenyl-methanol (R570)

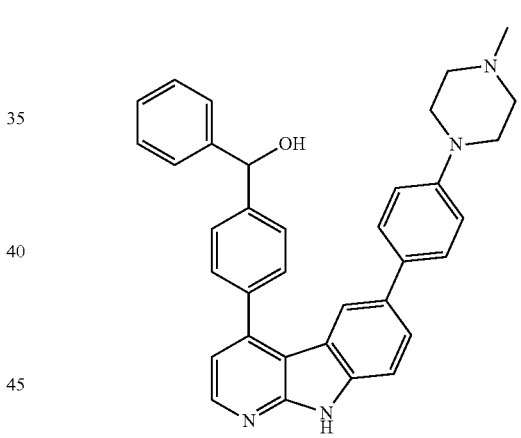

To a solution of R571 (example 23) (12 mg, 0.023 mmol) in CH$_2$Cl$_2$/MeOH 5:2 (0.7 mL), NaBH$_4$ (2 mg, 0.046 mmol) was added. After stirring for 1 h at r.t., the reaction mixture was quenched with sat. aq. NH$_4$Cl (0.3 mL), diluted with CH$_2$Cl$_2$ (20 mL) and washed with water (20 mL) The organic layer was collected and the aqueous layer washed twice with CH$_2$Cl$_2$ (20 mL) The combined organic layers were dried over MgSO$_4$, filtered and evaporated to dryness, to give the desired compound (12 mg, quantitative) as a yellow solid. $^1$H-NMR (300 MHz, CDCl$_3$) δ=8.20 (d, J=5.2 Hz, 1H), 7.71 (d, J=1.4 Hz, 1H), 7.55 (d, J=8.3 Hz, 2H), 7.51 (dd, J=8.5, 1.7 Hz, 1H), 7.47 (d, J=8.2 Hz, 2H), 7.39 (d, J=8.4 Hz, 1H), 7.34-7.28 (m, 2H), 7.24-7.17 (m, 4H), 7.17-7.09 (m, 1H), 6.93 (d, J=5.2 Hz, 1H), 6.79 (d, J=8.8 Hz, 2H), 5.80 (s, 1H), 3.18-3.03 (m, 4H), 2.58-2.45 (m, 4H), 2.25 (s, 3H). $^{13}$C-NMR (101 MHz, CDCl$_3$) δ=152.76 (Cq), 149.98 (Cq), 146.34 (Cq), 145.65 (Cq), 145.25 (CH), 144.77 (Cq), 138.74 (Cq), 138.04 (Cq), 134.06 (Cq), 132.94 (Cq), 129.15 (2 CH), 128.87 (2 CH), 127.83 (2 CH), 127.75 (CH), 127.31 (4 CH), 126.20 (CH), 121.41 (Cq), 120.65 (CH), 117.18 (2 CH), 116.67 (CH), 114.73 (Cq), 111.89 (CH), 75.97 (CH), 55.21 (2 $CH_2$), 49.29 (2 $CH_2$), 45.89 ($CH_3$). HRMS (ESI): calcd. for $C_{35}H_{33}N_4O$: 525.2649. found: 525.2653.

Example 34

{6-[4-(4-Methylpiperazin-1-yl)-phenyl]-9H-pyrido[2,3-b]indol-4-yl}-(2-nitro-phenyl)-amine (R548)

9-Benzenesulfonyl-6-(4-(4-methylpiperazin-1-yl)phenyl)-N-(2-nitrophenyl)-9H-pyrido[2,3-b]indol-4-amine

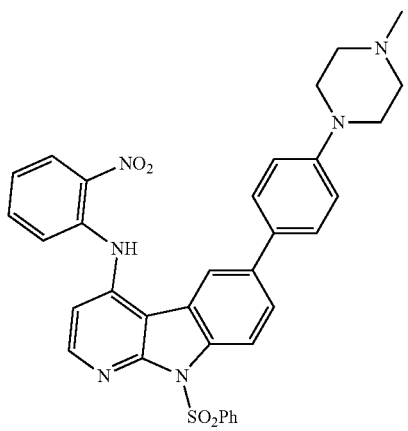

In a Schlenk tube with a stirring bar, the 6-substituted-carboline (1 eq), $K_2CO_3$ (3 eq), 2-nitro-aniline (1.3 eq), X-phos (0.16 eq), and $Pd_2(dba)_3$ (0.08 eq) were placed. The tube was evacuated and back-filled with argon (this was repeated three additional times). Then, t-BuOH was introduced to obtain a 0.05 M suspension (degassed solvents were used). The reaction mixture was allowed to stir at 100° C. for 15 h. After cooling to room temperature and dilution with EtOAc, the mixture was filtered through a Celite® pad. The solvents of the filtrate were removed under reduced pressure. A yellow solid was obtained in 69% yield after trituration of the crude product in MeOH and filtration. $^1$H NMR (300 MHz, $CDCl_3$) δ 10.10 (s, 1H), 8.56 (d, J=8.8 Hz, 1H), 8.46 (d, J=5.6 Hz, 1H), 8.26 (dd, J=8.5, 1.3 Hz, 1H), 8.22 (d, J=1.5 Hz, 1H), 8.18 (d, J=7.3 Hz, 2H), 7.78 (dd, J=8.8, 1.6 Hz, 1H), 7.63-7.49 (m, 5H), 7.43 (t, J=7.6 Hz, 2H), 7.32 (d, J=5.6 Hz, 1H), 7.06 (dd, J=8.4, 1.2 Hz, 1H), 7.01 (d, J=8.6 Hz, 2H), 3.35-3.19 (m, 4H), 2.68-2.53 (m, 4H), 2.37 (s, 3H); $^{13}$C NMR (75 MHz, $CDCl_3$) δ 153.1 (C), 150.7 (C), 147.7 (CH), 142.5 (C), 138.8 (C), 138.5 (C), 137.5 (C), 136.3 (C), 135.9 (C), 135.8 (CH), 134.1 (CH), 131.4 (C), 129.1 (CH), 127.9 (CH), 127.8 (CH), 127.0 (CH), 126.7 (CH), 122.5 (C), 121.1 (CH), 119.4 (CH), 118.5 (CH), 116.4 (CH), 115.2 (CH), 110.0 (C), 109.0 (CH), 55.1 ($CH_2$), 48.9 ($CH_2$), 46.2 ($CH_3$); MS (ESI) m/z: 310.1 $[M+2H]^{2+}$, 619.2 $[M+H]^+$.

{6-[4-(4-Methylpiperazin-1-yl)-phenyl]-9H-pyrido[2,3-b]indol-4-yl}-(2-nitro-phenyl)-amine (R548)

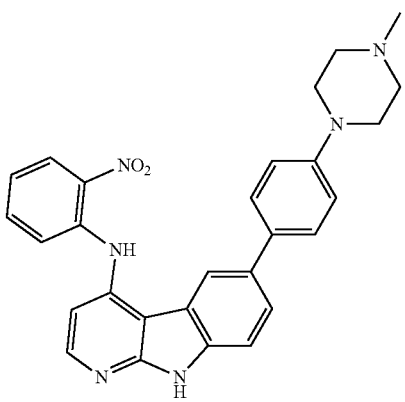 [SMILES: CN1CCN(c2ccc(-c3ccc4[nH]c5nccc(Nc6ccccc6[N+](=O)[O-])c5c4c3)cc2)CC1]

9-Benzenesulfonyl-6-(4-(4-methylpiperazin-1-yl)phenyl)-N-(2-nitrophenyl)-9H-pyrido[2,3-b]indol-4-amine underwent typical procedure A above.

The trituration procedure afforded the desired compound in 69% yield as a brown solid. $^1$H-NMR (300 MHz, DMSO) δ=11.92 (s, 1H), 9.75 (s, 1H), 8.31 (d, J=5.5 Hz, 1H), 8.26 (dd, J=8.4, 1.4 Hz, 1H), 7.96 (d, J=0.8 Hz, 1H), 7.67 (dd, J=8.5, 1.5 Hz, 1H), 7.67-7.60 (m, 1H), 7.54 (d, J=8.5 Hz, 1H), 7.50-7.45 (m, 1H), 7.42 (d, J=8.7 Hz, 2H), 7.24-7.16 (m, 1H), 7.10 (d, J=5.5 Hz, 1H), 6.98 (d, J=8.8 Hz, 2H), 3.22-3.12 (m, 4H), 2.48-2.41 (m, 4H), 2.22 (s, 3H). $^{13}$C NMR (101 MHz, DMSO) δ 154.0 (C), 149.8 (C), 147.1 (CH), 142.5 (C), 138.1 (C), 137.2 (C), 137.1 (C), 135.8 (CH), 131.9 (C), 131.2 (C), 127.0 (CH), 126.3 (CH), 124.4 (CH), 121.3 (CH), 120.4 (CH), 119.8 (C), 119.0 (CH), 115.6 (CH), 111.3 (CH), 106.1 (C), 105.8 (CH), 54.6 ($CH_2$), 48.0 ($CH_2$), 45.8 ($CH_3$). HRMS (ESI): calcd. for $C_{28}H_{27}N_6O_2$: 479.2195. found: 479.2137.

Examples 35 and 36 were synthesised in a similar fashion to example 34, starting from building blocks A or C, accordingly.

Example 35

6-(4-(4-Methylpiperazin-1-yl)phenyl)-N-(3-nitrophenyl)-9H-pyrido[2,3-b]indol-4-amine(R547)

A bright yellow solid was obtained in 57% yield after trituration of the crude product in MeOH and filtration $^1$H NMR (300 MHz, DMSO) δ 11.80 (s, NH), 9.20 (s, NH), 8.22 (d, J=5.5 Hz, 1H), 8.13 (s, 1H), 8.07 (ft, J=1.9 Hz, 1H), 7.86 (d, J=7.9 Hz, 1H), 7.70 (d, J=8.4 Hz, 1H), 7.66-7.58 (m, J=8.1 Hz, 2H), 7.50 (d, J=8.2 Hz, 1H), 7.48 (d, J=8.5 Hz, 2H), 6.98 (d, J=8.2 Hz, 2H), 6.96 (d, J=5.2 Hz, 1H), 3.21-3.06 (m, 4H), 2.48-2.41 (m, 4H), 2.22 (s, 3H); $^{13}$C NMR (75 MHz, DMSO) δ 154.2 (C), 149.7 (C), 148.6 (C), 147.0 (CH), 144.5 (C), 143.5 (C), 136.9 (C), 131.6 (C), 131.5 (C), 130.5 (CH), 127.1 (CH), 125.5 (CH), 123.9 (CH), 120.3 (CH), 120.2 (C), 116.0 (CH), 115.6 (CH), 113.5 (CH), 110.9 (CH), 104.9 (C), 103.5 (CH), 54.6 (CH$_2$), 48.1 (CH$_2$), 45.8 (CH$_3$); HRMS calcd for C$_{28}$H$_{27}$N$_6$O$_2$ [M+H]$^+$ 479.2190 found 479.2182.

Example 36

6-(4-(4-(1-Methylpiperidin-4-yl)piperazin-1-yl)phenyl)-N-(2-nitrophenyl)-9H-pyrido[2,3-b]indol-4-amine (R567)

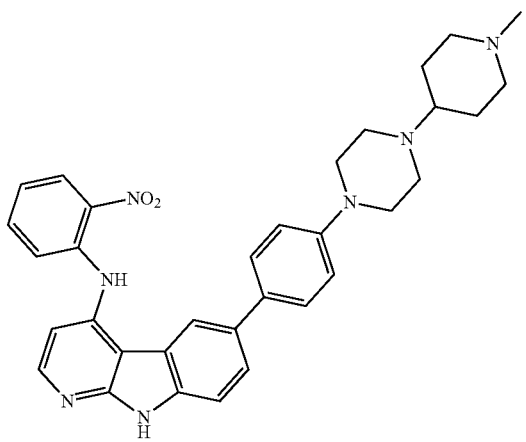 [SMILES: CN1CCC(N2CCN(c3ccc(-c4ccc5[nH]c6nccc(Nc7ccccc7[N+](=O)[O-])c6c5c4)cc3)CC2)CC1]

A dark red solid was obtained in 91% yield after trituration of the crude product in MeOH and filtration. $^1$H NMR (400 MHz, DMSO) δ 11.92 (s, 1H), 9.75 (s, 1H), 8.31 (d, J=5.5 Hz, 1H), 8.26 (dd, J=8.5, 1.5 Hz, 1H), 7.97 (d, J=1.2 Hz, 1H), 7.69-7.60 (m, 2H), 7.54 (d, J=8.5 Hz, 1H), 7.49 (dd, J=8.4, 1.0 Hz, 1H), 7.42 (d, J=8.8 Hz, 2H), 7.19 (ddd, J=8.3, 7.2, 1.2 Hz, 1H), 7.10 (d, J=5.6 Hz, 1H), 6.96 (d, J=8.9 Hz, 2H), 3.18-3.10 (m, 4H), 2.81 (d, J=11.7 Hz, 2H), 2.65-2.57 (m, 4H), 2.15 (s, 4H), 1.86 (t, J=10.9 Hz, 2H), 1.75 (d, J=12.4 Hz, 2H), 1.43 (ddd, J=15.3, 11.8, 3.1 Hz, 2H); $^{13}$C NMR (101 MHz, DMSO) δ 154.03 (s), 149.84 (s), 147.14 (CH), 142.49 (s), 138.11 (s), 137.20 (s), 137.09 (s), 135.77 (CH), 131.93 (s), 131.23 (s), 126.98 (CH), 126.33 (CH), 124.37 (CH), 121.33 (CH), 120.48 (CH), 119.82 (s), 119.04 (CH), 115.54 (CH), 111.34 (CH), 106.03 (s), 105.70 (CH), 60.62 (CH), 54.74 (2CH$_2$), 48.76 (2CH$_2$), 48.49 (2CH$_2$), 45.76 (NCH$_3$), 27.87 (2CH$_2$); HRMS calcd for C$_{33}$H$_{37}$N$_7$O$_2$ [M+2H]$^{2+}$ 281.6499 found 281.6496.

Example 37

6-[4-(4-Methylpiperazin-1-yl)-phenyl]-4-phenyl-ethynyl-9H-pyrido[2,3-b]indole (R523)

9-Benzenesulfonyl-6-[4-(4-methylpiperazin-1-yl)-phenyl]-4-phenylethynyl-9H-pyrido[2,3-b]indole Building block A was placed in a Schlenk tube, followed by the addition of PdCl$_2$(CH$_3$CN)$_2$ (0.08 equiv.), 2-dicyclohexylphosphino-2',4',6'-triisopropylbiphenyl (0.16 equiv.) and Cs$_2$CO$_3$ (2.6 equiv.). The tube was evacuated and back-filled with argon (this was repeated three additional times). Anhydrous acetonitrile (for a 0.08 M concentration of 1) was added and then the alkyne (1.3 equiv.) was injected. The reaction mixture was allowed to stir at 90° C. overnight. Then the reaction mixture was cooled to room temperature and quenched with H$_2$O mQ (1 mL). It was diluted with EtOAc (3 volumes) and filtered through Celite, the pad of Celite was washed 5 times with EtOAc (10 mL) The filtrate was washed twice with H$_2$O/brine 1:1 (50 mL), dried over Mg$_2$SO$_4$ and evaporated to dryness. The residue was suspended in a minimum volume of methanol, triturated and filtered, and the solid washed with methanol, to afford the desired compound in 82% yield as a brown solid. $^1$H-NMR (300 MHz, CDCl$_3$) δ=8.82 (d, J=1.6 Hz, 1H), 8.61-8.48 (m, 2H), 8.16 (d, J=7.7 Hz, 2H), 7.82 (dd, J=8.8, 1.8 Hz, 1H), 7.71-7.57 (m, 4H), 7.53 (t, J=7.4 Hz, 1H), 7.48-7.35 (m, 6H), 7.01 (d, J=8.7 Hz, 2H), 3.44-3.26 (m, 4H), 2.83-2.65 (m, 4H), 2.46 (s, 3H). $^{13}$C-NMR (75 MHz, CDCl$_3$) δ=150.76 (Cq), 146.33 (CH), 138.75 (Cq), 137.04 (Cq), 136.67 (Cq), 134.09 (CH), 132.07 (Cq, 2 CH), 131.81 (Cq), 129.72 (CH), 129.06 (2 CH), 128.78 (2 CH), 127.92 (2 CH), 127.64 (2 CH), 127.42 (CH), 124.96 (Cq), 123.55 (Cq), 122.06 (Cq), 121.64 (CH), 120.20 (CH), 118.41 (Cq), 116.27 (2 CH), 115.03 (CH), 98.92 (Cq), 85.93 (Cq), 55.12 (2 CH$_2$), 48.94 (2 CH$_2$), 46.22 (CH$_3$). ESI-MS: 583.2 m/z

6-[4-(4-Methylpiperazin-1-yl)-phenyl]-4-phenyl-ethynyl-9H-pyrido[2,3-b]indole

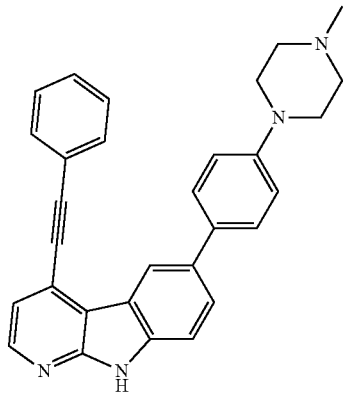 [SMILES: CN1CCN(c2ccc(-c3ccc4[nH]c5nccc(C#Cc6ccccc6)c5c4c3)cc2)CC1]

9-Benzenesulfonyl-6-[4-(4-methylpiperazin-1-yl)-phenyl]-4-phenylethynyl-9H-pyrido[2,3-b]indole underwent typical procedure A. The trituration procedure in MeOH afforded the desired compound in 81% yield as a brown solid. $^1$H-NMR (300 MHz, DMSO) δ=12.07 (s, 1H), 8.69 (d, J=2.2 Hz, 1H), 8.46 (d, J=5.1 Hz, 1H), 7.82-7.74 (m, 3H), 7.63-7.54 (m, 6H), 7.34 (d, J=5.1 Hz, 1H), 7.04 (d, J=8.7 Hz, 2H), 3.23-3.14 (m, 4H), 2.49-2.44 (m, 4H), 2.24 (s, 3H). $^{13}$C-NMR (101 MHz, DMSO) δ=152.27 (Cq), 149.85 (Cq), 145.83 (CH), 137.99 (Cq), 132.28 (Cq), 131.46 (2 CH), 131.23 (Cq), 129.68 (CH), 128.97 (2 CH), 126.94 (2 CH), 125.66 (CH), 122.62 (Cq), 121.43 (Cq), 120.52 (Cq), 118.69 (CH), 116.77 (CH), 115.58 (2 CH), 114.46 (Cq), 111.68 (CH), 96.75 (Cq), 86.54 (Cq), 54.42 (2 CH$_2$), 47.87 (2 CH$_2$), 45.54 (CH$_3$). HRMS (ESI): calcd. for C$_{30}$H$_{27}$N$_4$: 443.2230. found: 443.2247.

Examples 38 to 43 below were synthesized in a similar fashion to example 37.

Example 38

4-(2-Methoxyphenylethynyl)-6-[4-(4-methylpiperazin-1-yl)-phenyl]-9H-pyrido[2,3-b]indole (R538)

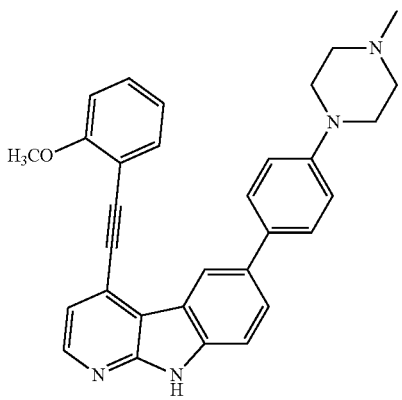 [SMILES: COc1ccccc1C#Cc1ccnc2[nH]c3ccc(-c4ccc(N5CCN(C)CC5)cc4)cc3c12]

The trituration procedure afforded the desired compound in 79% yield as a brown powder. $^1$H-NMR (400 MHz, DMSO) δ=12.04 (s, 1H), 8.83 (d, J=1.1 Hz, 1H), 8.43 (d, J=5.1 Hz, 1H), 7.73 (dd, J=8.5, 1.6 Hz, 1H), 7.68 (dd, J=7.5, 1.4 Hz, 1H), 7.58 (d, J=8.4 Hz, 1H), 7.56-7.47 (m, 3H), 7.31 (d, J=5.1 Hz, 1H), 7.18 (d, J=8.4 Hz, 1H), 7.08 (t, J=7.5 Hz, 1H), 7.01 (d, J=8.7 Hz, 2H), 3.69 (s, 3H), 3.20-3.13 (m, 4H), 2.48-2.42 (m, 4H), 2.22 (s, 3H). $^{13}$C-NMR (101 MHz, DMSO) δ=160.11 (Cq), 152.41 (Cq), 149.97 (Cq), 145.92 (CH), 137.99 (Cq), 133.52 (CH), 132.58 (Cq), 131.66 (Cq), 131.61 (CH), 127.30 (2 CH), 126.06 (CH), 123.21 (Cq), 120.80 (CH), 120.66 (Cq), 119.08 (CH), 117.11 (CH), 115.74 (2 CH), 114.35 (Cq), 111.64 (2 CH), 110.46 (Cq), 94.13 (Cq), 90.28 (Cq), 55.86 (CH$_3$), 54.61 (2 CH$_2$), 48.10 (2 CH$_2$), 45.84 (CH$_3$). HRMS (ESI): calcd. for C$_{31}$H$_{29}$N$_4$O: 473.2336. found: 473.2332.

Example 39

6-[4-(4-Methylpiperazin-1-yl)-phenyl]-4-(2-trifluoromethyl-phenylethynyl)-9H-pyrido[2,3-b]indole (R539)

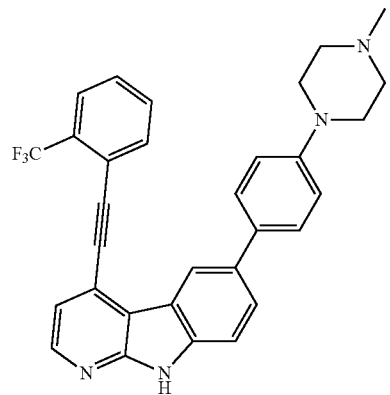 [SMILES: CN1CCN(c2ccc(-c3ccc4[nH]c5nccc(C#Cc6ccccc6C(F)(F)F)c5c4c3)cc2)CC1]

The trituration procedure afforded the desired compound in 71% yield as an orange solid. $^1$H-NMR (400 MHz, DMSO) δ=11.98 (s, 1H), 8.61 (d, J=1.4 Hz, 1H), 8.48 (d, J=5.0 Hz, 1H), 8.03 (d, J=7.6 Hz, 1H), 7.92 (d, J=7.9 Hz, 1H), 7.85 (t, J=7.6 Hz, 1H), 7.76 (dd, J=8.4, 1.7 Hz, 2H), 7.76-7.70 (m, J=7.8 Hz, 2H), 7.61 (d, J=8.5 Hz, 1H), 7.53 (d, J=8.7 Hz, 2H), 7.34 (d, J=5.0 Hz, 1H), 6.98 (d, J=8.7 Hz, 2H), 3.20-3.15 (m, 5H), 2.49-2.44 (m, 4H), 2.24 (s, 3H). $^{13}$C-NMR (101 MHz, DMSO) δ=152.29 (Cq), 149.80 (Cq), 145.76 (CH), 138.04 (Cq), 134.38 (CH), 132.69 (CH), 132.47 (Cq), 131.14 (Cq), 129.95 (CH), 129.66 (Cq), 126.97 (2 CH), 126.25 (d, J=5.0 Hz, CH), 126.00 (CH), 123.43 (d, J=273.4 Hz, Cq), 121.70 (Cq), 120.22 (Cq), 119.22 (Cq), 118.57 (CH), 117.34 (CH), 115.43 (2 CH), 114.18 (Cq), 111.69 (CH), 91.96 (Cq), 91.45 (Cq), 54.43 (2 CH$_2$), 47.87 (2 CH$_2$), 45.56 (CH$_3$). HRMS (ESI): calcd. for C$_{31}$H$_{26}$F$_3$N$_4$: 511.2104. found: 511.2091

Example 40

4-((4-Fluorophenyl)ethynyl)-6-[4-(4-methylpiperazin-1-yl)-phenyl]-9H-pyrido[2,3-b]indole (R540)

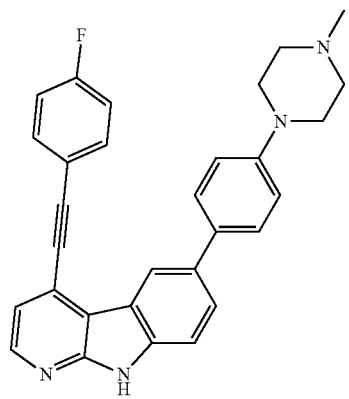 [SMILES: CN1CCN(c2ccc(-c3ccc4[nH]c5nccc(C#Cc6ccc(F)cc6)c5c4c3)cc2)CC1]

The trituration procedure afforded the desired compound in 86% yield as a yellow solid. $^1$H-NMR (500 MHz, DMSO)

δ=11.91 (s, 1H), 8.66 (d, J=1.3 Hz, 1H), 8.45 (d, J=5.0 Hz, 1H), 7.85-7.80 (m, 2H), 7.77 (dd, J=8.4, 1.3 Hz, 1H), 7.61 (d, J=8.4 Hz, 1H), 7.56 (d, J=8.6 Hz, 2H), 7.41 (t, J=8.8 Hz, 2H), 7.32 (d, J=5.0 Hz, 1H), 7.03 (d, J=8.6 Hz, 2H), 3.25-3.20 (m, 4H), 2.49-2.44 (m, 4H), 2.25 (s, 3H). $^{13}$C-NMR (126 MHz, DMSO) δ=162.48 (d, J=249.4 Hz, Cq), 152.21 (Cq), 149.79 (Cq), 145.69 (CH), 137.91 (Cq), 133.80 (CH), 133.73 (CH), 132.19 (Cq), 131.09 (Cq), 126.78 (2 CH), 125.54 (CH), 122.40 (Cq), 120.41 (Cq), 118.56 (CH), 117.86 (d, J=3.4 Hz, Cq), 116.67 (CH), 116.29 (CH), 116.11 (CH), 115.49 (2 CH), 114.36 (Cq), 111.56 (CH), 95.56 (Cq), 86.25 (Cq), 54.38 (2 $CH_2$), 47.83 (2 $CH_2$), 45.49 ($CH_3$). HRMS (ESI): calcd. for $C_{30}H_{26}FN_4$: 461.2136. found: 461.2138.

Example 41

4-((2-Fluorophenyl)ethynyl)-6-[4-(4-methylpiperazin-1-yl)-phenyl]-9H-pyrido[2,3-b]indole (R541)

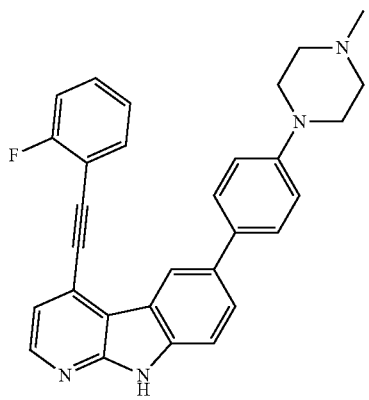 [SMILES: CN1CCN(c2ccc(-c3ccc4[nH]c5nccc(C#Cc6ccccc6F)c5c4c3)cc2)CC1]

The trituration procedure afforded the desired compound in 71% yield as a brown solid. $^1$H-NMR (400 MHz, DMSO) δ=12.13 (s, 1H), 8.72 (s, 1H), 8.47 (d, J=5.0 Hz, 1H), 7.84 (t, J=7.0 Hz, 1H), 7.78 (d, J=8.1 Hz, 1H), 7.66-7.46 (m, 5H), 7.41 (d, J=7.3 Hz, 1H), 7.37 (d, J=4.9 Hz, 1H), 7.03 (d, J=8.6 Hz, 2H), 3.24-3.10 (m, 4H), 2.48-2.41 (m, 4H), 2.23 (s, 3H). $^{13}$C-NMR (101 MHz, DMSO) δ=162.16 (d, J=250.7 Hz, Cq), 152.38 (Cq), 149.99 (Cq), 146.03 (CH), 138.11 (Cq), 133.76 (CH), 132.48 (Cq), 132.32 (d, J=7.0 Hz, CH), 131.21 (Cq), 127.12 (2 CH), 126.11 (CH), 125.26 (d, J=3.3 Hz, CH), 122.12 (Cq), 120.45 (Cq), 118.64 (CH), 117.22 (CH), 116.18 (d, J=20.4 Hz, CH), 115.66 (2 CH), 114.37 (Cq), 111.88 (CH), 109.95 (d, J=15.4 Hz, Cq), 91.47 (Cq), 90.08 (Cq), 54.65 (2 $CH_2$), 48.00 (2 $CH_2$), 45.84 ($CH_3$). HRMS (ESI): calcd. for $C_{30}H_{26}FN_4$: 461.2136. found: 461.2129.

Example 42

4-((2-Chlorophenyl)ethynyl)-6-[4-(4-methylpiperazin-1-yl)-phenyl]-9H-pyrido[2,3-b]indole (R549)

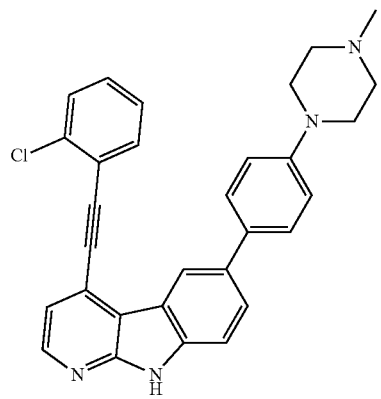 [SMILES: CN1CCN(c2ccc(-c3ccc4[nH]c5nccc(C#Cc6ccccc6Cl)c5c4c3)cc2)CC1]

The trituration procedure was not able to purify the desired compound, which was purified by silica gel flash chromatography ($CH_2Cl_2$/EtOH 85:15) in 26% yield as a yellow solid. $^1$H-NMR (300 MHz, $CDCl_3$) δ=9.82 (s, 1H), 8.90 (s, 1H), 8.46 (d, J=4.9 Hz, 1H), 7.74 (d, J=8.5 Hz, 2H), 7.63 (d, J=8.4 Hz, 2H), 7.56 (d, J=8.2 Hz, 1H), 7.51 (d, J=7.8 Hz, 1H), 7.40-7.30 (m, 3H), 7.03 (d, J=8.5 Hz, 2H), 3.33-3.25 (m, 4H), 2.69-2.58 (m, 4H), 2.39 (s, 3H). $^{13}$C-NMR (101 MHz, $CDCl_3$) δ=152.68 (Cq), 150.33 (Cq), 145.21 (CH), 137.78 (Cq), 136.31 (Cq), 134.14 (CH), 133.98 (Cq), 133.28 (Cq), 130.38 (CH), 129.72 (CH), 128.17 (2 CH), 126.84 (2 CH), 124.11 (Cq), 122.79 (Cq), 121.65 (Cq), 120.79 (CH), 118.69 (CH), 116.43 (2 CH), 116.26 (Cq), 111.25 (CH), 94.14 (Cq), 91.68 (Cq), 55.30 (2 $CH_2$), 49.29 (2 $CH_2$), 46.33 ($CH_3$). HRMS (ESI): calcd. for $C_{30}H_{26}ClN_4$: 477.1825. found: 477.1817.

Example 43

6-(4-(4-Methylpiperazin-1-yl)phenyl)-4-((triisopropylsilyl)ethynyl)-9H-pyrido[2,3-b]indole (R606)

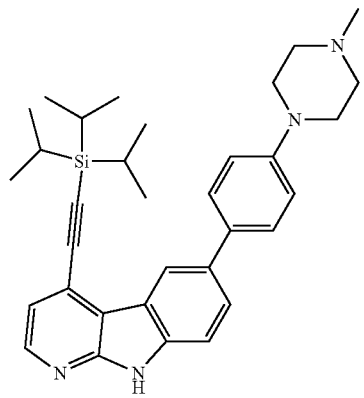 [SMILES: CC(C)[Si](C#Cc1ccnc2[nH]c3ccc(-c4ccc(N5CCN(C)CC5)cc4)cc3c12)(C(C)C)C(C)C]

The crude product was purified by silica gel flash column chromatography (DCM/MeOH 100:0 to 95:5) to afford a the desired product in 37% chemical yield as a dark yellow amorphous solid. ¹H NMR (400 MHz, CDCl₃) δ 9.70 (s, 1H), 8.75 (d, J=1.6 Hz, 1H), 8.41 (d, J=5.1 Hz, 1H), 7.71 (dd, J=8.4, 1.8 Hz, 1H), 7.59 (d, J=8.7 Hz, 2H), 7.55 (d, J=8.4 Hz, 1H), 7.27 (d, J=6.5 Hz, 1H), 7.00 (d, J=8.7 Hz, 2H), 3.45-3.27 (m, 4H), 2.87-2.70 (m, 4H), 2.50 (s, 3H), 1.30-1.21 (m, 3H), 1.19 (d, J=6.0 Hz, 18H); ¹³C NMR (101 MHz, CDCl₃) δ 152.6 (C), 149.9 (C), 145.2 (CH), 137.7 (C), 133.9 (C), 133.8 (C), 128.3 (CH), 126.8 (CH), 124.7 (C), 121.7 (C), 120.8 (CH), 119.4 (CH), 116.6 (CH), 116.2 (C), 111.2 (CH), 103.9 (C), 100.9 (C), 54.9 (2CH₂), 48.9 (2CH₂), 45.7 (NCH₃), 18.9 (6CH₃), 11.5 (3CH); HRMS calcd for C₃₃H₄₃N₄Si [M+H]⁺ 523.3252 found 523.3232.

Example 44

4-Ethynyl-6-(4-(4-methylpiperazin-1-yl)phenyl)-9H-pyrido[2,3-b]indole R(608)

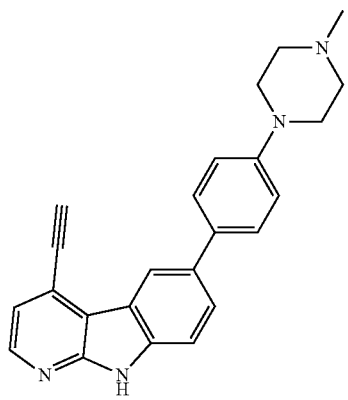 [SMILES: C#Cc1ccnc2[nH]c3ccc(-c4ccc(N5CCN(C)CC5)cc4)cc3c12]

The precursor used in Example 43, 9-benzenesulfonyl-6-(4-(4-methylpiperazin-1-yl)phenyl)-4-((triisopropylsilyl) ethynyl)-9H-pyrido[2,3-b]indole, which was obtained in a similar fashion as the procedure of Example 37, was deprotected from both the benzenesufonyl and triisopropylsilyl group using the following procedure. Under an inert atmosphere, to a solution of 9-benzenesulfonyl-6-(4-(4-methyl-piperazin-1-yl)phenyl)-4-((triisopropylsilyl)ethynyl)-9H-pyrido[2,3-b]indole (73.8 mg, 0.111 mmol) in anhydrous THF (2.8 mL, 0.05M), a solution of TBAF (1M in THF, 3 eq, 330 μL) was added dropwise. The reaction was stirred at 70° C. for 2.5 h. After cooling to R.T, the mixture was then quenched cautiously with water and brine. The aqueous layer was extracted with DCM (3×40 mL) The combined organic layers were washed with brine, dried over MgSO₄, filtered and concentrated under reduced pressure. The crude product was first purified by silica gel flash chromatography (DCM/MeOH 95:5 to 94:6) to afford the desired product contaminated by TBAF. A pale yellow solid was obtained in 41% yield after a double trituration of the previous mixture in MeOH and then in DCM followed by filtration. ¹H NMR (300 MHz, DMSO) δ 12.07 (s, 1H), 8.59 (d, J=1.1 Hz, 1H), 8.42 (d, J=5.0 Hz, 1H), 7.76 (dd, J=8.5, 1.7 Hz, 1H), 7.59 (d, J=8.7 Hz, 1H), 7.55 (d, J=8.8 Hz, 2H), 7.28 (d, J=5.0 Hz, 1H), 7.06 (d, J=8.8 Hz, 2H), 5.09 (s, 1H), 3.25-3.09 (m, 8H), 2.24 (s, 3H); ¹³C NMR (101 MHz, DMSO) δ 152.29 (C), 149.93 (C), 145.94 (CH), 138.04 (C), 132.39 (C), 131.36 (C), 127.13 (CH), 126.07 (CH), 122.20 (C), 120.33 (C), 118.66 (CH), 117.79 (CH), 115.81 (CH), 114.71 (C), 111.80 (CH), 89.04 (C), 80.61 (CH), 54.55 (2CH₂), 47.96 (2CH₂), 45.75 (NCH₃); HRMS calcd for C₂₄H₂₃N₄ [M+H]⁺ 367.1917 found 367.1914.

Example 45

4-(2-Methoxyphenylethynyl)-9-methyl-6-[4-(4-methylpiperazin-1-yl)-phenyl]-9H-pyrido[2,3-b]indole (R555)

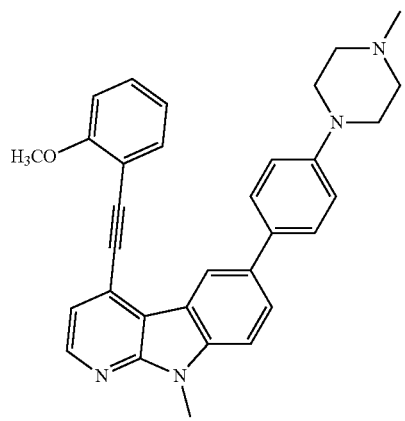 [SMILES: COc1ccccc1C#Cc1ccnc2c1c1cc(-c3ccc(N4CCN(C)CC4)cc3)ccc1n2C]

To a 0.04 M solution of R538 (example 38) in DMF, at 0° C. and under an inert atmosphere, NaH (60% dispersion in mineral oil, 2 equiv.) was added. After stirring at 0° C. for 0.33 h, CH₃I (1 equiv.) was slowly added. The ice-bath was removed and the reaction was allowed to stir for 1 h at room temperature. Then it was quenched with H₂O (0.1 mL), diluted with CH₂Cl₂ (20 mL) and washed twice with H₂O/brine 1:1 (20 mL). The organic layer was dried over MgSO₄, filtered and evaporated to dryness. Purification by silica gel flash chromatography (CH₂Cl₂/EtOH 95:5) afforded the desired compound in 76% yield as a yellow solid. ¹H-NMR (300 MHz, CDCl₃) δ=9.06 (d, J=1.6 Hz, 1H), 8.45 (d, J=5.1 Hz, 1H), 7.75 (dd, J=8.5, 1.8 Hz, 1H), 7.66 (dd, J=7.6, 1.7 Hz, 1H), 7.62 (d, J=8.7 Hz, 2H), 7.48 (d, J=8.5 Hz, 1H), 7.39 (ddd, J=8.5, 7.6, 1.7 Hz, 1H), 7.28 (d, J=5.1 Hz, 1H), 7.04-6.96 (m, 3H), 6.92 (d, J=8.3 Hz, 1H), 3.98 (s, 3H), 3.64 (s, 3H), 3.32-3.23 (m, 4H), 2.70-2.60 (m, 4H), 2.40 (s, 3H). ¹³C-NMR (75 MHz, CDCl₃) δ=160.63 (Cq), 152.33 (Cq), 150.15 (Cq), 145.31 (CH), 139.48 (Cq), 134.01 (CH), 133.91 (Cq), 133.55 (Cq), 130.90 (CH), 128.27 (2 CH), 126.40 (CH), 124.64 (Cq), 121.05 (Cq), 120.97 (CH), 120.67 (CH), 117.65 (CH), 116.52 (2 CH), 115.80 (Cq), 111.98 (Cq), 110.81 (CH), 108.95 (CH), 94.31 (Cq), 90.92 (Cq), 55.79 (CH₃), 55.16 (2 CH₂), 49.31 (2 CH₂), 46.20 (CH₃), 27.92 (CH₃). HRMS (ESI): calcd. for C₃₂H₃₁N₄O: 487.2492. found: 487.2475.

Example 46

4-(4-Methoxy-phenylsulfanyl)-6-[4-(4-methyl-piperazin-1-yl)-phenyl]-9H-pyrido[2,3-b]indole (R619)

9-Benzenesulfonyl-4-(4-methoxy-phenylsulfanyl)-6-[4-(4-methyl-piperazin-1-yl)-phenyl]-9H-pyrido[2,3-b]indole To a suspension of 9-Benzenesulfonyl-4-chloro-6-[4-(4-methyl-piperazin-1-yl)-phenyl]-9H-pyrido[2,3-b]indole (Building block A) (60 mg) in DMF (1.2 mL), under Argon, $K_2CO_3$ (56 mg, 3.5 equiv.) and 4-methoxythiophenol (0.029 mL, 2 equiv.) were added. After stirring for 0.5 h at r.t., the reaction mixture was diluted with AcOEt (20 mL), washed with sat. aqueous $NH_4Cl$ (20 mL) and brine (20 mL) The organic layer was dried over $MgSO_4$, filtered and evaporated to dryness. The trituration procedure afforded the desired compound in 72% yield as a beige solid. $^1$H-NMR (300 MHz, CDCl$_3$) δ=8.55 (d, J=8.8 Hz, 1H), 8.48 (d, J=1.6 Hz, 1H), 8.21 (d, J=5.4 Hz, 1H), 8.18-8.09 (m, 2H), 7.77 (dd, J=8.8, 1.9 Hz, 1H), 7.65 (d, J=8.7 Hz, 2H), 7.57-7.48 (m, 3H), 7.45-7.35 (m, 2H), 7.04 (d, J=7.8 Hz, 2H), 7.01 (d, J=8.7 Hz, 2H), 6.53 (d, J=5.5 Hz, 1H), 3.88 (s, 3H), 3.47-3.33 (m, 4H), 2.90-2.74 (m, 4H), 2.51 (s, 3H). $^{13}$C-NMR (75 MHz, CDCl$_3$) δ=161.4 (C), 150.7 (C), 150.6 (C), 147.7 (C), 146.0 (CH), 138.8 (C), 137.7 (2 CH), 137.1 (C), 136.0 (C), 134.0 (CH), 131.9 (C), 129.0 (2 CH), 128.0 (2 CH), 127.6 (2 CH), 126.5 (CH), 123.8 (C), 121.5 (CH), 118.2 (C), 116.3 (2 CH), 115.8 (2 CH), 115.1 (CH), 114.8 (CH), 114.6 (C), 55.5 (CH$_3$), 55.1 (2 CH$_2$), 48.8 (2 CH$_2$), 46.2 (CH$_3$). ESI-MS: m/z 621.2 [M+H]$^+$.

4-(4-Methoxy-phenylsulfanyl)-6-[4-(4-methyl-piperazin-1-yl)-phenyl]-9H-pyrido[2,3-b]indole

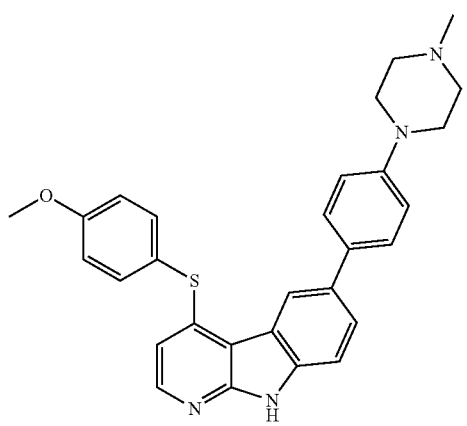 [SMILES: COc1ccc(Sc2ccnc3[nH]c4ccc(-c5ccc(N6CCN(C)CC6)cc5)cc4c23)cc1]

Following deprotection of 9-Benzenesulfonyl-4-(4-methoxy-phenylsulfanyl)-6-[4-(4-methyl-piperazin-1-yl)-phenyl]-9H-pyrido[2,3-b]indole under typical procedure A, the trituration procedure afforded the desired compound in 95% yield as an orange solid. $^1$H-NMR (300 MHz, CDCl$_3$) δ=10.04 (s, 1H), 8.55 (s, 1H), 8.16 (d, J=5.4 Hz, 1H), 7.75-7.51 (m, 6H), 7.10-7.00 (m, 4H), 6.47 (d, J=5.4 Hz, 1H), 3.89 (s, 3H), 3.38-3.26 (m, 4H), 2.76-2.64 (m, 4H), 2.43 (s, 3H). $^{13}$C-NMR (101 MHz, CDCl$_3$) δ=159.7 (C), 150.7 (C), 148.5 (C), 144.4 (CH), 144.3 (C), 136.4 (C), 136.0 (2 CH), 131.5 (C), 131.2 (C), 126.3 (2 CH), 123.6 (CH), 120.1 (C), 119.6 (CH), 117.5 (C), 114.9 (2 CH), 114.4 (2 CH), 110.4 (C), 110.1 (CH), 109.7 (CH), 54.2 (CH$_3$), 53.4 (2 CH$_2$), 47.1 (2 CH$_2$), 44.4 (CH$_3$). HRMS (ESI): calcd. for $C_{29}H_{29}N_4OS$: 481.2057. found: 481.2045.

Example 47

4-(1-(4-methylbenzyl)-1H-1,2,3-triazol-4-yl)-6-(4-(4-methylpiperazin-1-yl)phenyl)-9H-pyrido[2,3-b]indole (R620)

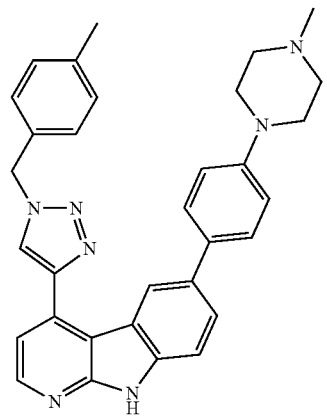 [SMILES: Cc1ccc(Cn2cc(-c3ccnc4[nH]c5ccc(-c6ccc(N7CCN(C)CC7)cc6)cc5c34)nn2)cc1]

To a solution of 4-ethynyl-6-(4-(4-methylpiperazin-1-yl)phenyl)-9H-pyrido[2,3-b]indole (example 44, 26.1 mg, 0.071 mmol) in 1.4 mL of anhydrous DMF (C=0.05M), was added CuI (2 mg, 0.15 eq) and 185 μL of a 0.5M solution of 1-(azidomethyl)-4-methylbenzene (1.3 eq). Then, diisopropylethylamine (82 μL, 7 eq) was introduced. The reaction mixture was stirred at room temperature for 15 h. The mixture was then hydrolysed with water (30 mL) The aqueous layer was extracted with AcOEt (4×15 mL). The combined organic layers were washed twice with brine, dried over MgSO$_4$, filtered and concentrated under reduced pressure. A light brown solid was obtained in 66% yield (24.2 mg) after trituration of the crude product in MeOH and filtration. $^1$H NMR (500 MHz, DMSO) δ 11.99 (s, 1H), 9.01-8.92 (m, 2H), 8.47 (s, 1H), 7.70 (dd, J=8.4, 1.6 Hz, 1H), 7.55 (d, J=8.4 Hz, 1H), 7.49 (d, J=8.7 Hz, 2H), 7.41 (d, J=3.6 Hz, 1H), 7.34 (d, J=7.9 Hz, 2H), 7.19 (d, J=7.8 Hz, 2H), 7.02 (d, J=8.7 Hz, 2H), 5.73 (s, 2H), 3.19 (s, 4H), 2.29 (s, 4H), 2.25 (s, 3H); $^{13}$C NMR (126 MHz, DMSO) δ 153.1 (s), 149.5 (s), 145.5 (CH), 144.9 (s), 137.9 (s), 137.3 (s), 132.8 (s), 132.6 (s), 131.6 (s), 131.5 (s), 129.1 (CH), 127.7 (CH), 126.7 (CH), 125.0 (CH), 124.4 (CH), 121.5 (CH), 120.5 (s), 115.5 (CH), 110.9 (CH), 54.4 (2CH$_2$), 52.8 (CH$_2$), 47.9 (2CH$_2$), 45.4 (NCH$_3$), 20.4 (CH$_3$); HRMS calcd for $C_{32}H_{32}N_7$ [M+H]$^+$ 514.2714 found 514.2699.

Examples 48-56 below were synthesised in a similar fashion to example 2, starting from building block A

Example 48

6-(4-(4-methylpiperazin-1-yl)phenyl)-4-(4-phenoxyphenyl)-9H-pyrido[2,3-b]indole (R621)

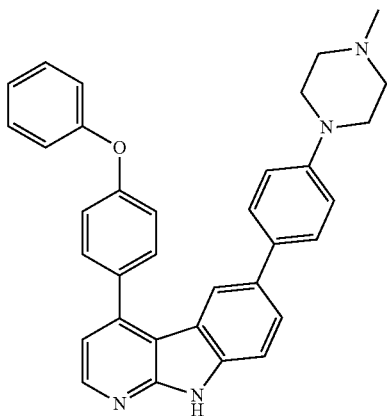 [SMILES: CN1CCN(c2ccc(-c3ccc4[nH]c5nccc(-c6ccc(Oc7ccccc7)cc6)c5c4c3)cc2)CC1]

A white solid was obtained in 62% yield after trituration of the crude product in MeOH and filtration. $^1$H NMR (400 MHz, DMSO) δ 11.99 (s, 1H), 8.45 (d, J=5.0 Hz, 1H), 7.77 (d, J=6.3 Hz, 2H), 7.76 (d, J=2.3 Hz, 1H), 7.66 (dd, J=8.5, 1.7 Hz, 1H), 7.55 (d, J=8.4 Hz, 1H), 7.44 (ft, J=8.4, 7.6 Hz, 2H), 7.36 (d, J=8.7 Hz, 2H), 7.26 (d, J=8.6 Hz, 2H), 7.20 (t, J=7.4 Hz, 1H), 7.14 (d, J=7.6 Hz, 2H), 7.13 (d, J=4.9 Hz, 1H), 6.97 (d, J=8.8 Hz, 2H), 3.24-3.15 (m, 4H), 2.64-2.53 (m, 4H), 2.31 (s, 3H); $^{13}$C NMR (101 MHz, DMSO) δ 157.2 (C), 156.6 (C), 152.8 (C), 149.5 (C), 146.2 (CH), 143.7 (C), 138.0 (C), 133.4 (C), 131.6 (C), 131.6 (C), 130.5 (CH), 130.2 (CH), 126.9 (CH), 125.1 (CH), 123.8 (CH), 120.4 (C), 119.1 (CH), 118.9 (CH), 115.8 (CH), 112.4 (C), 111.7 (CH), 54.3 (CH$_2$), 47.6 (CH$_2$), 45.3 (CH$_3$); HRMS calcd for C$_{34}$H$_{31}$N$_4$O [M+H]$^+$ 511.2492 found 511.2473.

Example 49

4-(6-(4-fluorophenyl)pyridin-3-yl)-6-(4-(4-methylpiperazin-1-yl)phenyl)-9H-pyrido[2,3-b]indole (R650)

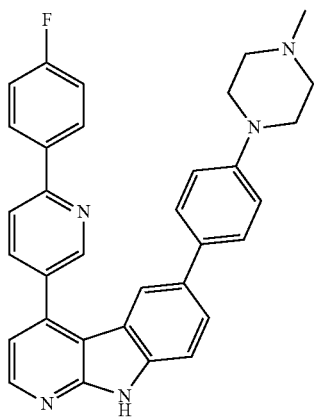 [SMILES: CN1CCN(c2ccc(-c3ccc4[nH]c5nccc(-c6ccc(-c7ccc(F)cc7)nc6)c5c4c3)cc2)CC1]

The crude product was purified by silica gel flash chromatography (DCM/MeOH 100:0 to 95:5) to afford the desired product in 80% yield as a white solid. $^1$H NMR (300 MHz, DMSO) δ 12.09 (s, 1H), 9.02 (d, J=2.1 Hz, 1H), 8.52 (d, J=5.0 Hz, 1H), 8.35-8.23 (m, 4H), 7.70 (s, 1H), 7.68 (dd, J=8.6 Hz, 1.7 Hz, 1H), 7.58 (d, J=8.3 Hz, 1H), 7.40 (t, J=8.8 Hz, 2H), 7.33 (d, J=8.7 Hz, 2H), 7.24 (d, J=5.0 Hz, 1H), 6.92 (d, J=8.8 Hz, 2H), 3.13 (t, J=4.9 Hz, 4H), 2.48 (t, J=4.9 Hz, 4H), 2.25 (s, 3H); $^{13}$C NMR (75 MHz, DMSO) δ 163.1 (d, J=246.8 Hz, C), 155.2 (C), 152.7 (C), 149.7 (C), 149.0 (CH), 146.3 (CH), 140.5 (C), 138.1 (C), 137.4 (CH), 134.7 (C), 134.6 (C), 132.7 (C), 131.9 (C), 131.4 (C), 128.9 (d, J=8.6 Hz, CH), 126.9 (CH), 125.5 (CH), 120.2 (C), 119.3 (d, J=76.5 Hz, CH), 116.0 (CH), 115.7 (CH), 112.4 (CH), 111.9 (CH), 107.0 (CH), 54.4 (CH$_2$), 47.7 (CH$_2$), 45.5 (NCH$_3$); MS (ESI) m/z: 514.3 [M+H]$^+$; 1027.7 [2M+H]$^+$; HRMS calcd for C$_{34}$H$_{29}$N$_5$F [M+H]$^+$ 514.2401 found 514.2390.

Example 50

(2,5-dimethoxy-4-(6-(4-(4-methylpiperazin-1-yl)phenyl)-9H-pyrido[2,3-b]indol-4-yl)phenyl)(phenyl)methanone (R654)

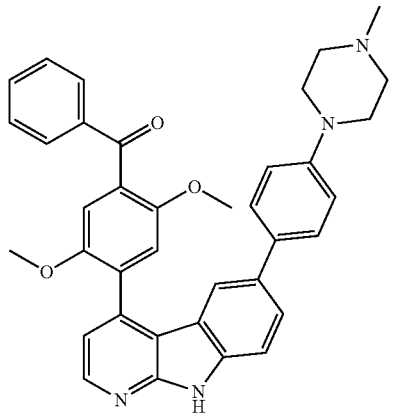 [SMILES: COc1cc(-c2ccnc3[nH]c4ccc(-c5ccc(N6CCN(C)CC6)cc5)cc4c23)c(OC)cc1C(=O)c1ccccc1]

The crude product was purified by silica gel flash chromatography (DCM/MeOH 98:2 to 94:6) to afford the desired product in 70% yield as a yellowish solid. $^1$H NMR (300 MHz, CDCl$_3$) δ 11.97 (s, 1H), 8.65 (d, J=5.1 Hz, 1H), 7.94 (d, J=8.5 Hz, 2H), 7.72-7.67 (m, 2H), 7.62 (d, J=8.8 Hz, 1H), 7.59 (t, J=7.3 Hz, 1H), 7.45 (t, J=7.7 Hz, 2H), 7.43 (d, J=8.7 Hz, 2H), 7.24 (d, J=5.1 Hz, 1H), 7.21 (s, 1H), 7.18 (s, 1H), 6.94 (d, J=8.8 Hz, 2H), 3.70 (s, 3H), 3.65 (s, 3H), 3.26 (t, J=5.0 Hz, 4H), 2.64 (t, J=5.0 Hz, 4H), 2.40 (s, 3H); $^{13}$C NMR (75 MHz, CDCl$_3$) δ 196.0 (C=O), 153.1 (C), 151.4 (C), 150.8 (C), 149.9 (C), 144.9 (CH), 141.2 (C), 138.3 (C), 137.8 (C), 133.1 (CH), 132.9 (C), 132.8 (C), 130.8 (C), 129.9 (CH), 129.5 (C), 128.5 (CH), 127.4 (CH), 125.8 (CH), 121.5 (C), 120.1 (CH), 116.7 (CH), 116.4 (CH), 115.1 (C), 114.7 (CH), 112.7 (CH), 111.5 (CH), 56.5 (OCH$_3$), 56.4 (OCH$_3$), 55.1 (2CH$_2$), 48.9 (2CH$_2$), 46.1 (NCH$_3$); MS (ESI) m/z: 583.2 [M+H]$^+$; 1165.8 [2M+H]$^+$; HRMS calcd for C$_{37}$H$_{35}$N$_4$O$_3$ [M+H]$^+$ 583.2703 found 583.2689.

The boronic pinacolic ester (2,5-dimethoxy-4-(4,4,5,5-tetramethyl-1,3,2-dioxaborolan-2-yl)phenyl)(phenyl)methanone used in this synthesis was obtained as follows:

(4-bromo-2,5-dimethoxyphenyl)(phenyl)methanone

To a solution of 2-bromo-1,4-bis(methyloxy)benzene (2.0 g, 9.21 mmol) and benzoyl chloride (1.229 mL, 10.596 mmol, 1.15 eq) in DCM (9.5 mL, C=1.0M) at 0° C. was added triflic acid (0.815 mL, 9.21 mmol) over 5 min. The reaction mixture was allowed to warm to ambient temperature (40 min) and then slowly heated to gentle reflux (oil bath at 42° C.) and stirred for 48 h. The reaction mixture was cooled to r.t., and MeOH (0.3 mL) was added and stirring was continued for 30 min. The reaction mixture was poured into 80 mL of ice cooled water. The aqueous layer was neutralized with a 1 M NaOH solution. The layers were separated. The aqueous layer was extracted twice with DCM (2×20 mL). The combined organic phase was washed twice with a 1/1 water/brine mixture (2×30 mL), dried over MgSO$_4$, filtered and concentrated in vacuo to a brown-orange oil. Then, MTBE (7 mL) was added and the mixture was stirred into an ultra-sound bath. The resulting solid was filtered, rinsed with 1:1 MTBE/hexanes mixture and air dried to afford [4-bromo-2,5-bis(methyloxy)phenyl](phenyl)methanone in 76% yield (2.258 g) as a white solid. $^1$H NMR (300 MHz, DMSO) δ 7.72 (d, J=8.5 Hz, 1H), 7.65 (t, J=7.4 Hz, 1H), 7.51 (t, J=7.6 Hz, 1H), 7.45 (s, 1H), 7.10 (s, 1H), 3.81 (s, 2H), 3.63 (s, 2H), $^{13}$C NMR (75 MHz, DMSO) δ 194.5 (C=O), 150.7 (C), 149.7 (C), 136.7 (C), 133.5 (CH), 129.3 (2CH), 128.6 (2CH), 128.2 (C), 117.3 (CH), 113.3 (C), 112.5 (CH), 56.7 (OCH$_3$), 56.5 (OCH$_3$); MS (ESI) m/z: 321.1, 323.0 [M+H, $^{79}$Br, $^{81}$Br]$^+$; 243.1, 245.0 [M-Ph, $^{79}$Br, $^{81}$Br]$^+$.

(2,5-dimethoxy-4-(4,4,5,5-tetramethyl-1,3,2-dioxaborolan-2-yl)phenyl)(phenyl)methanone

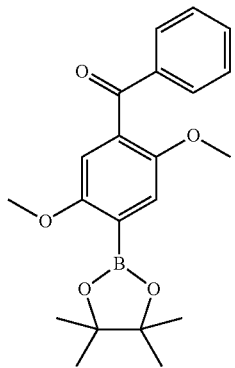 [SMILES: COc1cc(C(=O)c2ccccc2)c(OC)cc1B1OC(C)(C)C(C)(C)O1]

In a Schlenk tube with a stirring bar, (4-bromo-2-hydroxy-5-methoxyphenyl)-(phenyl)methanone (200 mg, 0.623 mmol), potassium acetate AcOK (183 mg, 3 eq), bis(pinacolato)diboron (237 mg, 1.5 eq), and PdCl$_2$(dppf) (45 mg, 0.1 eq) were placed. The tube was evacuated and back-filled with nitrogen (this was repeated three additional times). Then, 9 mL of degassed 1,4-dioxane (C=0.07M) was introduced. The reaction mixture was allowed to stir at 100° C. for 14 h30. After cooling to r.t. and diluting with AcOEt, the mixture was filtered through a Celite® pad. The solvents were removed in vacuo. The crude product was purified by silica gel flash chromatography (DCM/MeOH 100:0 to 98.5:1.5) to afford the desired compound in 95% yield (281 mg, mainly contaminated with bis(pinacolato)diboron) as an uncolored amorphous solid. $^1$H NMR (300 MHz, CDCl$_3$) δ 7.78 (d, J=8.5 Hz, 2H), 7.53 (t, J=7.4 Hz, 1H), 7.40 (t, J=7.5 Hz, 2H), 7.27 (s, 1H), 6.86 (s, 1H), 3.78 (s, 3H), 3.68 (s, 3H), 1.37 (s, 12H); $^{13}$C NMR (75 MHz, CDCl$_3$) δ 196.4 (C=O), 158.3 (C), 150.9 (C), 137.6 (C), 133.1 (CH), 132.1 (C), 129.9 (CH), 128.3 (CH), 119.7 (CH), 111.9 (CH), 84.0 (C), 56.8 (OCH$_3$), 56.5 (OCH$_3$), 24.9 (4CH$_3$); MS (ESI) m/z: 369.1 [M+H]$^+$; 291.1 [M-Ph]$^+$.

Example 51

(2-hydroxy-5-methoxy-4-(6-(4-(4-methylpiperazin-1-yl)phenyl)-9H-pyrido[2,3-b]indol-4-yl)phenyl)(phenyl)methanone (R656)

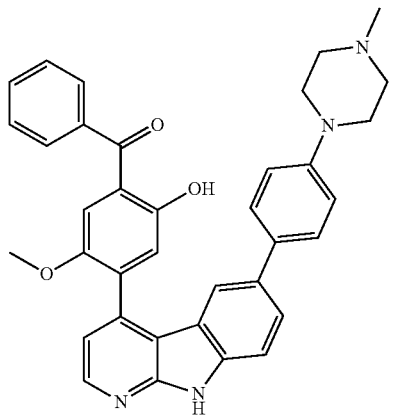 [SMILES: COc1cc(C(=O)c2ccccc2)c(O)cc1-c1ccnc2[nH]c3ccc(-c4ccc(N5CCN(C)CC5)cc4)cc3c12]

The crude product was purified by silica gel flash chromatography (DCM/MeOH 100:0 to 95:5) to afford the desired product in 68% yield as a yellow solid. $^1$H NMR (300 MHz, CDCl$_3$) δ 11.76 (s, 1H), 11.00 (s, 1H), 8.58 (d, J=5.1 Hz, 1H), 7.83 (d, J=8.5 Hz, 2H), 7.70-7.61 (m, 3H), 7.62-7.50 (m, 3H), 7.44 (d, J=8.7 Hz, 2H), 7.28 (s, 1H), 7.24 (s, 1H), 7.16 (d, J=5.0 Hz, 1H), 6.98 (d, J=8.7 Hz, 2H), 3.52 (s, 3H), 3.35-3.17 (m, 4H), 2.67-2.55 (m, 4H), 2.38 (s, 3H); $^{13}$C NMR (75 MHz, CDCl$_3$) δ 200.9 (C=O), 157.7 (C), 152.8 (C), 150.1 (C), 149.1 (C), 145.2 (CH), 140.2 (C), 138.1 (C), 138.0 (C), 137.2 (C), 133.2 (C), 133.1 (C), 132.4 (CH), 129.4 (CH), 128.7 (CH), 127.7 (CH), 126.1 (CH), 121.4 (C), 120.8 (CH), 120.5 (CH), 118.8 (C), 116.4 (CH), 116.3 (CH), 114.8 (C), 114.4 (CH), 111.4 (CH), 56.4 (OCH$_3$), 55.2 (2CH$_2$), 49.1 (2CH$_2$), 46.2 (NCH$_3$); MS (ESI) m/z: 569.3 [M+H]$^+$; 1137.7 [2M+H]$^+$; HRMS calcd for C$_{36}$H$_{33}$N$_4$O$_3$ [M+H]$^+$ 569.2547 found 569.2549.

The boronic pinacolic ester (2-hydroxy-5-methoxy-4-(4,4,5,5-tetramethyl-1,3,2-dioxaborolan-2-yl)phenyl)(phenyl)methanone used in this synthesis was obtained as follows:

(4-bromo-2-hydroxy-5-methoxyphenyl)(phenyl)methanone

A solution of [4-bromo-2,5-bis(methyloxy)phenyl](phenyl)methanone (400 mg, 1.245 mmol) in DCM (2.1 mL, C=0.6M) was added dropwise to a stirred solution of 1 M BCl$_3$ in DCM (1.55 mL, 1.25 eq) while maintaining the reaction temperature at 0° C. The reaction mixture was stirred at 0° C. for 35 min and then quenched by slow addition of MeOH (0.7 mL) over 15 min at 10° C. Then, 2N HCl solution (1.4 mL) was added at r.t. over 15 min. The layers were separated, and the organic phase was concentrated to dryness by rotavap. The yellow oily product was purified by silica gel column flash chromatography (elution in pure DCM) to afford [4-bromo-2-hydroxy-5-(methyloxy)phenyl](phenyl)methanone in 90% yield (344 mg) as a yellow solid. $^1$H NMR (300 MHz, CDCl$_3$) δ 11.67 (s, 1H), 7.67 (d, J=8.5 Hz, 2H), 7.60 (t, J=7.3 Hz, 1H), 7.51 (t, J=7.2 Hz, 2H), 7.29 (s, 1H), 7.02 (s, 1H), 3.70 (s, 3H); $^{13}$C NMR (75 MHz, CDCl$_3$) δ 200.4 (C=O), 157.5 (C), 148.3 (C), 137.6 (C), 132.3 (CH), 129.0 (CH), 128.5 (CH), 123.2 (CH), 121.9 (C), 117.8 (C), 114.7 (CH), 56.8 (OCH$_3$); MS (ESI) m/z: 307.4, 309.1 [M+H, $^{79}$Br, $^{81}$Br]$^+$; 229.1, 231.0 [M-Ph, $^{79}$Br, $^{81}$Br]$^1$.

(2-hydroxy-5-methoxy-4-(4,4,5,5-tetramethyl-1,3,2-dioxaborolan-2-yl)phenyl)(phenyl)methanone

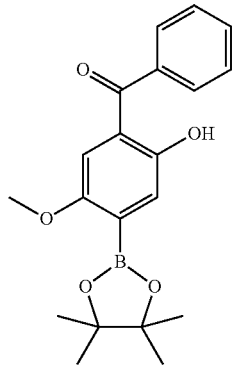 [SMILES: COc1cc(C(=O)c2ccccc2)c(O)cc1B1OC(C)(C)C(C)(C)O1]

In a Schlenk tube with a stirring bar, (4-bromo-2-hydroxy-5-methoxyphenyl)-(phenyl)methanone (200 mg, 0.651 mmol), potassium acetate AcOK (192 mg, 3 eq), bis(pinacolato)diboron (215 mg, 1.3 eq), and PdCl$_2$(dppf) (47 mg, 0.1 eq) were placed. The tube was evacuated and back-filled with nitrogen (this was repeated three additional times). Then, 9.3 mL of degassed 1,4-dioxane (C=0.07M) was introduced. The reaction mixture was allowed to stir at 100° C. for 15 h. After cooling to r.t. and diluting with AcOEt, the mixture was filtered through a Celite® pad. The solvents were removed in vacuo. The crude product was purified by silica gel flash chromatography (DCM/MeOH 100:0 to 98.5:1.5) to afford the desired compound in quantitative yield (267 mg, mainly contaminated with bis(pinacolato)diboron) as a red oil. $^1$H NMR (300 MHz, CDCl$_3$) δ 11.35 (s, 1H), 7.70 (dd, J=8.3, 1.4 Hz, 2H), 7.66-7.53 (m, 1H), 7.50 (t, J=7.3 Hz, 2H), 7.36 (s, 1H), 6.97 (s, 1H), 3.67 (s, 3H), 1.36 (s, 12H); $^{13}$C NMR (75 MHz, CDCl$_3$) δ 201.1 (C=O), 156.8 (C), 155.5 (C), 138.1 (C), 132.2 (CH), 129.3 (CH), 128.5 (CH), 126.1 (CH), 120.2 (C), 113.8 (CH), 84.3 (C), 56.8 (OCH$_3$), 24.9 (4CH$_3$); MS (ESI) m/z: 355.1 [M+H]$^+$; 709.3 [2M+H]$^+$.

Example 52

4-(4-benzyl-2,5-dimethoxyphenyl)-6-(4-(4-methylpiperazin-1-yl)phenyl)-9H-pyrido[2,3-b]indole (R666)

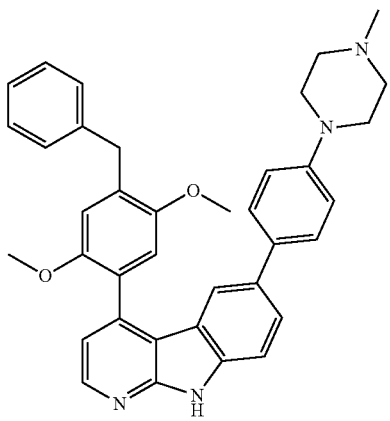 [SMILES: COc1cc(-c2ccnc3[nH]c4ccc(-c5ccc(N6CCN(C)CC6)cc5)cc4c23)c(OC)cc1Cc1ccccc1]

An orange solid was obtained in 57% yield after trituration of the crude product in MeOH and filtration. $^1$H NMR (300 MHz, CDCl$_3$) δ 9.94 (s, 1H), 8.52 (d, J=5.1 Hz, 1H), 7.68 (dd, J=7.1, 1.8 Hz, 1H), 7.65 (d, J=1.8 Hz, 1H), 7.53 (d, J=9.1 Hz, 1H), 7.38 (d, J=8.7 Hz, 2H), 7.33-7.28 (m, 4H), 7.25-7.20 (m, 1H), 7.17 (d, J=5.1 Hz, 1H), 7.02 (s, 1H), 6.93 (d, J=8.8 Hz, 2H), 6.89 (s, 1H), 4.18 (d, J=15.2 Hz, 1H), 4.08 (d, J=15.2 Hz, 1H), 3.77 (s, 3H), 3.60 (s, 3H), 3.32-3.22 (m, 4H), 2.68-2.57 (m, 4H), 2.39 (s, 3H); $^{13}$C NMR (75 MHz, CDCl$_3$) δ 152.8 (C), 151.7 (C), 150.7 (C), 145.0 (C), 145.5 (CH), 142.2 (C), 141.0 (C), 137.7 (C), 132.9 (C), 132.8 (C), 131.1 (C), 128.9 (CH), 128.6 (CH), 127.4 (CH), 126.0 (CH), 126.0 (C), 125.6 (CH), 122.0 (C), 120.5 (CH), 117.4 (CH), 116.4 (CH), 115.2 (C), 114.5 (CH), 113.5 (CH), 111.1 (CH), 56.4 (OCH$_3$), 56.3 (OCH$_3$), 55.3 (2CH$_2$), 49.1 (2CH$_2$), 46.3 (NCH$_3$), 36.3 (CH$_2$Bn); MS (ESI) m/z: 569.0 [M+H]$^+$; 1137.8 [2M+H]$^+$; 539.3[M-OCH$_3$+2H]'; HRMS calcd for C$_{37}$H$_{37}$N$_4$O$_2$ [M+H]$^+$ 569.2911 found 569.2924.

The boronic pinacolic ester 2-(4-benzyl-2,5-dimethoxyphenyl)-4,4,5,5-tetramethyl-1,3,2-dioxaborolane used in this synthesis was obtained as follows:

1-benzyl-4-bromo-2,5-dimethoxybenzene

To a solution of (4-bromo-2,5-dimethoxyphenyl)(phenyl)methanone (100 mg, 0.311 mmol) in 0.2 mL of anhydrous DCM (C=1.5M), were successively added dropwise trifluoroacetic acid (0.24 mL, 10 eq) and triethylsilane (0.2 mL, 4 eq). After 16 h of stirring at r.t., the reaction mixture was hydrolyzed with a saturated NH$_4$Cl solution (5 mL). The layers were diluted with 20 mL of DCM and 20 mL of water and then separated. The aqueous layer was extracted twice with DCM (2×10 mL) The combined organic phase was washed twice with a saturated NaHCO$_3$ solution (2×20 mL), brine (2×20 mL), dried over MgSO$_4$, filtered and concentrated in vacuo. The product was obtained pure enough for further reaction in 98% yield (93.4 mg). $^1$H NMR (300 MHz, CDCl$_3$) δ 7.34-7.25 (m, 2H), 7.24-7.17 (m, 3H), 7.08 (s, 1H), 6.69 (s, 1H), 3.95 (s, 2H), 3.78 (s, 3H), 3.78 (s, 3H); $^{13}$C NMR (75 MHz, CDCl$_3$) δ 151.9 (C), 150.1 (C), 140.4 (C), 129.9 (C), 128.9 (CH), 128.5 (CH), 126.1 (CH), 116.1 (CH), 115.0 (CH), 109.1 (C), 57.0 (OCH$_3$), 56.3 (OCH$_3$), 35.9 (CH$_2$Bn); MS (ESI) m/z: 324.5, 326.1 [M+NH$_4$, $^{79}$Br, $^{81}$Br]$^+$; 630.3, 632.0, 634.2 [2M+NH$_4$, $^{79}$Br, $^{81}$Br]$^+$.

2-(4-benzyl-2,5-dimethoxyphenyl)-4,4,5,5-tetramethyl-1,3,2-dioxaborolane

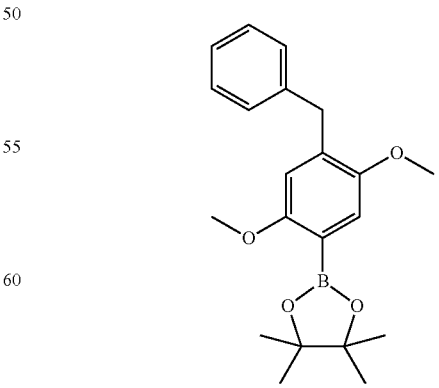

In a Schlenk tube with a stirring bar, 1-benzyl-4-bromo-2,5-dimethoxybenzene (93 mg, 0.303 mmol), potassium acetate AcOK (89 mg, 3 eq), bis(pinacolato)diboron (100 mg, 1.3 eq), and PdCl$_2$(dppf) (22 mg, 0.1 eq) were placed. The tube was evacuated and back-filled with nitrogen (this was repeated three additional times). Then, 4.3 mL of degassed 1,4-dioxane (C=0.07M) was introduced. The reaction mixture was allowed to stir at 100° C. for 14 h. After cooling to r.t. and diluting with AcOEt, the mixture was filtered through a Celite® pad. The solvents were removed in vacuo. The crude product was purified by silica gel flash chromatography (PE/AcOEt 100:0 to 80:20) to afford the desired compound in 62% yield (68.2 mg) as a white solid. $^1$H NMR (300 MHz, CDCl$_3$) δ 7.31-7.23 (m, 2H), 7.21 (s, 1H), 7.23-7.13 (m, 3H), 6.66 (s, 1H), 4.00 (s, 2H), 3.82 (s, 3H), 3.74 (s, 3H), 1.37 (s, 12H); $^{13}$C NMR (75 MHz, CDCl$_3$) δ 158.8 (C), 151.4 (C), 140.8 (C), 134.1 (C), 128.9 (CH), 128.3 (CH), 125.9 (CH), 118.5 (CH), 114.4 (CH), 83.5 (C), 57.0 (OCH$_3$), 56.2 (OCH$_3$), 36.4 (CH$_2$), 24.9 (4CH$_3$); MS (ESI) m/z: 355.4 [M+H]$^+$; 340.4 [M-CH$_3$+H]'; 325.3 [M-OCH$_3$+2H].

Example 53

2-benzyl-4-methoxy-5-(6-(4-(4-methylpiperazin-1-yl)phenyl)-9H-pyrido[2,3-b]indol-4-yl)phenol (R667)

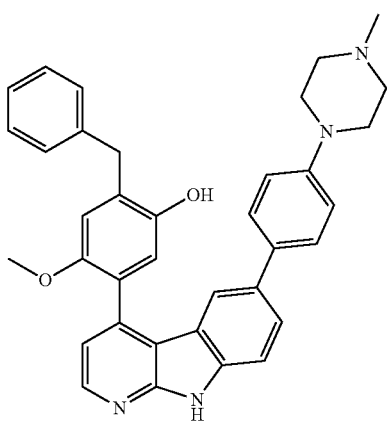 [SMILES: COc1cc(Cc2ccccc2)c(O)cc1-c1ccnc2[nH]c3ccc(-c4ccc(N5CCN(C)CC5)cc4)cc3c12]

The crude product was purified by silica gel flash chromatography (DCM/MeOH 94:6 to 90:10) to afford the desired product in 77% yield as a white solid. $^1$H NMR (300 MHz, 70 CDCl$_3$/30 CD$_3$OD) δ 8.17 (d, J=5.1 Hz, 1H), 7.52 (d, J=1.3 Hz, 1H), 7.47 (dd, J=8.5, 1.8 Hz, 1H), 7.34 (d, J=8.5 Hz, 1H), 7.24 (d, J=8.8 Hz, 2H), 7.20-7.08 (m, 4H), 7.04 (t, J=7.0 Hz, 1H), 6.95 (d, J=5.2 Hz, 1H), 6.80 (s, 1H), 6.76 (d, J=8.8 Hz, 2H), 6.68 (s, 1H), 4.04 (d, J=15.3 Hz, 1H), 3.93 (d, J=15.3 Hz, 1H), 3.39 (s, 3H), 3.17-3.06 (m, 4H), 2.66-2.55 (m, 4H), 2.28 (s, 3H). $^{13}$C NMR (75 MHz, CDCl$_3$) δ 151.7 (C), 149.7 (C), 149.0 (C), 148.7 (C), 144.2 (CH), 142.5 (C), 140.8 (C), 137.8 (C), 133.5 (C), 132.1 (C), 129.0 (C), 128.6 (CH), 128.2 (CH), 127.1 (CH), 125.7 (CH), 125.6 (CH), 125.3 (CH), 121.3 (C), 120.1 (CH), 117.0 (CH), 116.7 (CH), 116.6 (CH), 115.4 (C), 114.0 (CH), 111.0 (CH), 56.0 (OCH$_3$), 54.3 (2CH$_2$), 48.3 (2CH$_2$), 44.9 (NCH$_3$), 35.8 (CH$_2$Bn); MS (ESI) m/z: 552.2 [M+H]$^+$; 1109.6 [2M+H]$^+$; HRMS calcd for C$_{36}$H$_{35}$N$_4$O$_2$ [M+H]$^+$ 555.2754 found 555.2750.

The boronic pinacolic ester 2-benzyl-4-methoxy-5-(4,4,5,5-tetramethyl-1,3,2-dioxaborolan-2-yl)phenol used in this synthesis was obtained as follows:

2-benzyl-5-bromo-4-methoxyphenol

To a solution of (4-bromo-2-hydroxy-5-methoxyphenyl)(phenyl)methanone (100 mg, 0.325 mmol) in 0.22 mL of anhydrous DCM (C=1.5M), were successively added dropwise trifluoroacetic acid (0.25 mL, 10 eq) and triethylsilane (0.21 mL, 4 eq). After 17 h of stirring at r.t., the reaction mixture was hydrolyzed with a saturated NH$_4$Cl solution (5 mL) The layers were diluted with 20 mL of DCM and 20 mL of water and then separated. The aqueous layer was extracted twice with DCM (2×5 mL). The combined organic phase was washed twice with a saturated NaHCO$_3$ solution (2×20 mL), brine (20 mL), dried over MgSO$_4$, filtered and concentrated in vacuo. The crude product was purified by silica gel flash chromatography (Cyclohexane/AcOEt 97:3) to afford the desired product in 72% yield (68.5 mg) as an uncoloured oil. $^1$H NMR (300 MHz, CDCl$_3$) δ 7.36-7.28 (m, 2H), 7.28-7.20 (m, 3H), 7.01 (s, 1H), 6.70 (s, 1H), 4.89 (s, 1H), 3.96 (s, 2H), 3.80 (s, 3H); $^{13}$C NMR (75 MHz, CDCl$_3$) δ 150.3 (C), 148.1 (C), 139.4 (C), 128.8 (CH), 128.7 (CH), 127.5 (C), 126.6 (CH), 120.7 (CH), 115.0 (CH), 109.4 (C), 57.0 (OCH$_3$), 36.4 (CH$_2$Bn); MS (ESI) m/z: 310.1, 312.1 [M+NH$_4$, $^{79}$Br, $^{81}$Br]$^+$; 602.0, 604.3, 606.1 [2M+NH$_4$, $^{79}$Br, $^{81}$Br]$^+$.

2-benzyl-4-methoxy-5-(4,4,5,5-tetramethyl-1,3,2-dioxaborolan-2-yl)phenol

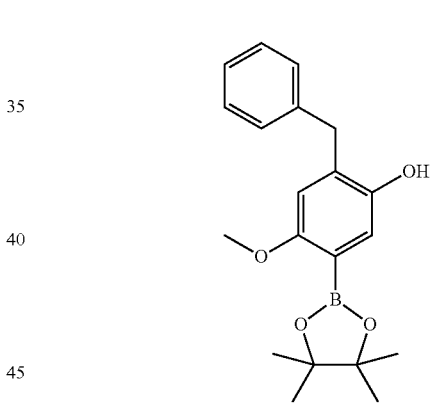

In a Schlenk tube with a stirring bar, 1-benzyl-4-bromo-2,5-dimethoxybenzene (68.5 mg, 0.233 mmol), potassium acetate AcOK (69 mg, 3 eq), bis(pinacolato)diboron (83 mg, 1.4 eq), and PdCl$_2$(dppf) (17 mg, 0.1 eq) were placed. The tube was evacuated and back-filled with nitrogen (this was repeated three additional times). Then, 3.3 mL of degassed 1,4-dioxane (C=0.07M) was introduced. The reaction mixture was allowed to stir at 100° C. for 15 h. After cooling to r.t. and diluting with AcOEt, the mixture was filtered through a Celite® pad. The solvents were removed in vacuo. The crude product was purified by silica gel flash chromatography (PE/AcOEt 100:0 to 70:30) to afford the desired compound in 87% yield (69 mg) as a yellowish oil. $^1$H NMR (300 MHz, CDCl$_3$) δ 7.33-7.12 (m, 6H), 6.63 (s, 1H), 5.96 (s, 1H), 4.00 (s, 2H), 3.71 (s, 3H), 1.33 (s, 12H); $^{13}$C NMR (75 MHz, CDCl$_3$) δ 158.4 (C), 147.7 (C), 140.3 (C), 131.7 (C), 128.8 (CH), 128.4 (CH), 126.1 (CH), 123.4 (CH), 114.0 (CH), 83.5 (C), 56.7 (OCH$_3$), 36.6 (CH$_2$), 24.9 (4CH$_3$); MS (ESI) m/z: 341.1 [M+H]$^+$; 698.8 [$^2$M+NH$_4$]$^+$.

Example 54

4-(4-benzyl-3-(trifluoromethyl)phenyl)-6-(4-(4-methylpiperazin-1-yl)phenyl)-9H-pyrido[2,3-b]indole (R686)

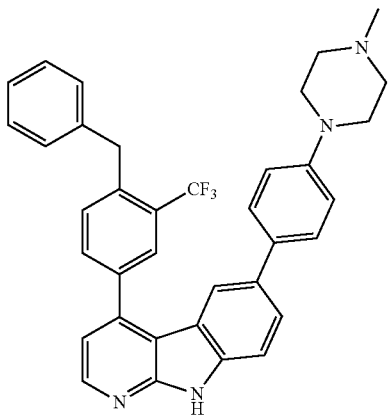 [SMILES: CN1CCN(c2ccc(-c3ccc4[nH]c5nccc(-c6ccc(Cc7ccccc7)c(C(F)(F)F)c6)c5c4c3)cc2)CC1]

A yellow solid was obtained in 48% yield after trituration of the crude product in MeOH and filtration. $^1$H NMR (300 MHz, CDCl$_3$) δ 9.82 (s, 1H), 8.53 (d, J=5.1 Hz, 1H), 8.15 (s, 1H), 7.81 (s, 1H), 7.77 (d, J=8.6 Hz, 1H), 7.68 (dd, J=8.4, 1.5 Hz, 1H), 7.57 (d, J=8.5 Hz, 1H), 7.41 (d, J=8.6 Hz, 2H), 7.39-7.21 (m, 6H), 7.12 (d, J=5.1 Hz, 1H), 6.95 (d, J=8.7 Hz, 2H), 4.33 (s, 2H), 3.49-3.28 (m, 4H), 2.92-2.73 (m, 4H), 2.53 (s, 3H); $^{13}$C NMR (75 MHz, CDCl$_3$) δ 152.9 (C), 149.7 (C), 149.6 (C), 146.2 (C), 146.0 (C), 143.9 (C), 140.3 (d, J=1.7 Hz, C), 139.7 (C), 137.8 (C), 137.0 (C), 133.5 (C), 133.3 (C), 132.6 (CH), 132.2 (CH), 129.3 (CH), 128.8 (CH), 127.8 (CH), 126.6 (CH), 126.5 (q, J=9.8 Hz, CH), 126.3 (CH), 124.7 (q, J=296.5 Hz, C), 121.1, 120.5 (CH), 116.8 (CH), 116.6 (CH), 111.6 (CH), 54.8 (2CH$_2$), 48.5 (2CH$_2$), 45.6 (NCH$_3$), 37.9 (q, J=1.4 Hz, CH$_2$Bn); MS (ESI) m/z: 577.3 [M+H]$^+$.

The boronic pinacolic ester 2-(4-benzyl-3-(trifluoromethyl)phenyl)-4,4,5,5-tetramethyl-1,3,2-dioxaborolane used in this synthesis was obtained as follows:

(4-bromo-2-(trifluoromethyl)phenyl)(phenyl)methanol

To a solution of 1,4-dibromo-2-(trifluoromethyl)benzene (300 mg, 0.987 mmol) in 2 mL of Et$_2$O (C=0.5M) was added dropwise a 1.6M solution of BuLi in hexane (650 μL, 1.05 eq) at −78° C. After 25 min of stirring, benzaldehyde (120 μL, 1.2 eq) was slowly added. The mixture was stirred for 2 h at −78° C. and was allowed to warm to r.t. overnight. Then, the reaction mixture was hydrolyzed with water and with a 1M HCl solution to acidify. The layers were separated. The aqueous layer was extracted with DCM (3×10 mL). The combined organics were washed with brine, dried over MgSO$_4$, filtered and solvents were removed in vacuo. The crude residue was purified by silica gel flash chromatography (cyclohexane/AcOEt 95:5) to afford the desired product in 90% yield (295 mg) as uncoloured oil. $^1$H NMR (300 MHz, CDCl$_3$) δ 7.80 (d, J=2.1 Hz, 1H), 7.67 (dd, J=8.4, 2.1 Hz, 1H), 7.54 (d, J=8.5 Hz, 1H), 7.39-7.27 (m, 5H), 6.24 (s, 1H), 2.44 (s, OH); $^{13}$C NMR (75 MHz, CDCl$_3$) δ 142.3 (C), 141.4 (q, J=1.4 Hz, C), 135.5 (CH), 131.5 (CH), 129.3 (q, J=30.9 Hz, C), 128.8 (q, J=6.1 Hz, CH), 128.7 (CH), 128.0 (CH), 126.5 (CH), 123.5 (q, J=274.6 Hz, C), 121.7 (C), 70.6 (q, J=2.1 Hz, CH); MS (ESI) m/z: 375.0, 377.0 [M−H+HCO$_2$H, $^{79}$Br, $^{81}$Br]−; 705.2, 707.2 [2M−2H+HCO$_2$H, $^{79}$Br, $^{81}$Br]−.

1-benzyl-4-bromo-2-(trifluoromethyl)benzene

Method A: To a solution of 1,4-dibromo-2-(trifluoromethyl)benzene (300 mg, 0.987 mmol) in 2 mL of Et$_2$O (C=0.5M) was added dropwise a 1.6M solution of BuLi in hexane (650 μL, 1.05 eq) at −65° C. After 15 min of stirring, benzyl bromide (141 μL, 1.2 eq) was slowly added. The mixture was slowly allowed to reach r.t. for 20 h. Then, the reaction mixture was hydrolyzed with water and with a 1M HCl solution. The organic layer was diluted (DCM) and separated. The aqueous layer was extracted with DCM (3×10 mL). The combined organics were washed with brine, dried over MgSO$_4$, filtered and solvents were removed in vacuo. The crude residue was purified by silica gel flash chromatography (cyclohexane) to afford the desired product in 74% yield (229 mg) as uncoloured oil.

Method B: To a solution of (4-bromo-2-(trifluoromethyl)phenyl)(phenyl)methanol (101.4 mg, 0.306 mmol) in 0.2 mL of anhydrous DCM (C=1.5M), were successively added dropwise trifluoroacetic acid (120 μL, 5 eq) and triethylsilane (146 μL, 3 eq). After 1 h45 of stirring at r.t., the reaction mixture was hydrolyzed with a saturated NH$_4$Cl solution (5 mL). The layers were diluted with 20 mL of DCM and 20 mL of water and then separated. The aqueous layer was extracted with DCM (3×10 mL). The combined organic phase was washed with a saturated NaHCO$_3$ solution (20 mL), brine (20 mL), dried over MgSO$_4$, filtered and concentrated in vacuo. The crude residue was purified by silica gel flash chromatography (Petroleum Ether) to afford the desired product in 65% yield (63.2 mg) as uncoloured oil.

$^1$H NMR (300 MHz, CDCl$_3$) δ 7.81 (d, J=2.1 Hz, 1H), 7.54 (dd, J=8.4, 2.2 Hz, 1H), 7.37-7.26 (m, 2H), 7.28-7.23 (m, 1H), 7.13 (d, J=8.7 Hz, 2H), 7.04 (d, J=8.3 Hz, 1H), 4.13 (s, 2H); $^{13}$C NMR (75 MHz, CDCl$_3$) δ 139.3 (C), 138.8 (q, J=1.5 Hz, C), 134.9 (CH), 133.5 (CH), 130.5 (q, J=30.4 Hz, C), 129.2 (CH), 129.1 (q, J=6.1 Hz, CH), 128.8 (CH), 126.7 (CH), 123.7 (q, J=274.4 Hz, C), 120.0 (C), 37.4 (q, J=2.1 Hz, CH$_2$).

2-(4-benzyl-3-(trifluoromethyl)phenyl)-4,4,5,5-tetramethyl-1,3,2-dioxaborolane

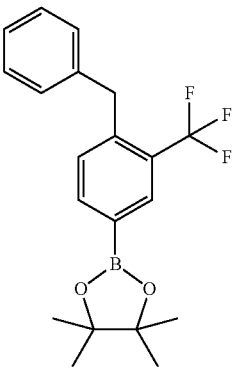 [SMILES: CC1(C)OB(c2ccc(Cc3ccccc3)c(C(F)(F)F)c2)OC1(C)C]

In a Schlenk tube with a stirring bar, 1-benzyl-4-bromo-2-(trifluoromethyl)benzene (89 mg, 0.282 mmol), potassium acetate AcOK (83 mg, 3 eq), bis(pinacolato)diboron (93 mg, 1.3 eq), and PdCl$_2$(dppf) (21 mg, 0.1 eq) were placed. The tube was evacuated and back-filled with nitrogen (this was repeated three additional times). Then, 4 mL of degassed 1,4-dioxane (C=0.07M) was introduced. The reaction mixture was allowed to stir at 100° C. for 15 h. After cooling to r.t. and diluting with AcOEt, the mixture was filtered through a Celite® pad. The solvents were removed in vacuo. The crude product was purified by silica gel flash chromatography (PE/DCM 100:0 to 70:30) to afford the desired compound in 82% yield (84 mg) as uncolored oil. $^1$H NMR (300 MHz, CDCl$_3$) δ 8.13 (s, 1H), 7.87 (d, J=7.7 Hz, 1H), 7.30 (tt, J=7.9, 1.8 Hz, 2H), 7.26-7.22 (m, 1H), 7.21 (d, J=7.6 Hz, 1H), 7.15 (d, J=8.4 Hz, 1H), 4.22 (s, 2H), 1.36 (s, 12H); $^{13}$C NMR (75 MHz, CDCl$_3$) δ 142.6 (q, J=1.6 Hz, C), 139.9 (C), 138.1 (CH), 132.3 (q, J=5.5 Hz, CH), 131.3 (CH), 129.2 (CH), 128.6 (CH), 128.4 (q, J=29.7 Hz, C), 126.4 (CH), 124.8 (q, J=274.2 Hz, C), 84.3 (2C), 38.1 (d, J=1.9 Hz, CH$_2$), 25.0 (4CH$_3$); MS (ESI) m/z: 380.1 [M+NH$_4$]$^+$; 742.2 [$^2$M+NH$_4$]$^+$.

Example 55

4-(4-benzyl-2-(trifluoromethyl)phenyl)-6-(4-(4-methylpiperazin-1-yl)phenyl)-9H-pyrido[2,3-b]indole (R687)

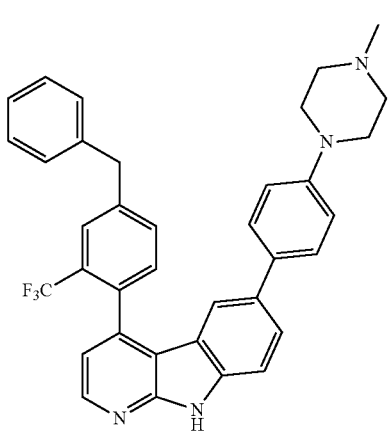 [SMILES: CN1CCN(c2ccc(-c3ccc4[nH]c5nccc(-c6ccc(Cc7ccccc7)cc6C(F)(F)F)c5c4c3)cc2)CC1]

The crude product was purified by silica gel flash chromatography (DCM/MeOH 100:0 to 95:5) to afford the desired product in 51% yield as a pale yellow solid. $^1$H NMR (300 MHz, DMSO) δ 12.01 (s, 1H), 8.46 (d, J=5.0 Hz, 1H), 7.92 (s, 1H), 7.73 (d, J=8.2 Hz, 1H), 7.62 (d, J=8.3 Hz, 1H), 7.52 (d, J=8.1 Hz, 2H), 7.41-7.17 (m, 5H), 7.14 (d, J=8.6 Hz, 2H), 7.08 (d, J=5.0 Hz, 1H), 6.91 (d, J=8.7 Hz, 2H), 6.78 (s, 1H), 4.22 (s, 2H), 3.25-3.10 (m, 4H), 2.65-2.52 (m, 4H), 2.30 (s, 3H); $^{13}$C NMR (75 MHz, DMSO) δ 152.1 (C), 149.5 (C), 145.5 (CH), 142.8 (C), 141.1 (C), 140.6 (C), 137.9 (C), 134.6 (d, J=1.4 Hz, C), 133.1 (CH), 131.6 (C), 131.5 (d, J=10.1 Hz, CH), 131.4 (CH), 131.2 (C), 128.8 (CH), 128.7 (CH), 126.9 (d, J=29.7 Hz, C), 126.6 (CH), 126.2 (CH), 125.2 (CH), 123.9 (d, J=274.5 Hz, C), 120.4 (C), 118.4 (CH), 115.9 (CH), 115.8 (CH), 113.7 (C), 111.8 (CH), 54.3 (2CH$_2$), 47.7 (2CH$_2$), 45.4 (NCH$_3$), 40.3 (CH$_2$Bn); MS (ESI) m/z: 577.0 [M+H]$^+$.

The boronic pinacolic ester 2-(4-benzyl-2-(trifluoromethyl)phenyl)-4,4,5,5-tetramethyl-1,3,2-dioxaborolane used in this synthesis was obtained as follows:

1-bromo-4-iodo-2-(trifluoromethyl)benzene

A solution prepared by the addition of 4-bromo-3-(trifluoromethyl)aniline (500 mg, 2.08 mmol) to a warmed mixture of concentrated H$_2$SO$_4$ 37% w/w (0.51 mL, 4.6 eq) and water (2.3 mL, C=3.4M) was cooled with vigourous stirring to −10° C. (ice-salt bath). A slurry of the aniline hydrogen sulfate precipitated. Then, a solution of NaNO$_2$ (158 mg, 1.1 eq) in 1.06 mL (C=2.15M) of water was added dropwise. The mixture was stirred for 40 min at −8° C. before a solution of KI (495 mg, 1.43 eq) in water (0.4 mL, C=8M) and copper powder (4 mg) were added. The brown reaction mixture was allowed to warm to r.t. by removal of the ice bath, stirred for 30 min, and then, the reactants were heated at reflux (102° C.) for an additional 1 h. After cooling to r.t. and diluting with water, the aqueous layer was extracted with DCM (3×20 mL). Extracts were washed with a saturated Na$_2$S$_2$O$_3$ solution (20 mL), with brine (20 mL), dried over MgSO$_4$, filtered and evaporated in vacuo. The crude residue was chromatographed (hexane) to afford the iodinated compound in 93% yield (679 mg) as an orange solid. $^1$H NMR (300 MHz, CDCl$_3$) δ 7.98 (d, J=2.3 Hz, 1H), 7.69 (dd, J=8.4, 2.1 Hz, 1H), 7.42 (d, J=8.4 Hz, 1H); $^{13}$C NMR (75 MHz, CDCl$_3$) δ 142.1 (CH), 136.7 (q, J=5.6 Hz, CH), 136.6 (CH), 132.0 (q, J=31.7 Hz, C), 121.9 (q, J=274.2 Hz, C), 120.0 (q, J=1.7 Hz, C), 91.8 (C).

(4-bromo-3-(trifluoromethyl)phenyl)(phenyl)methanol

To a solution of 1-bromo-4-iodo-2-(trifluoromethyl)benzene (246 mg, 0.701 mmol) in 1.4 mL of Et$_2$O (C=0.5M) was added dropwise a 1.6M solution of BuLi in hexane (460 µL, 1.05 eq) at −78° C. After 15 min of stirring, benzaldehyde (86 µL, 1.2 eq) was slowly added. The mixture was stirred for 4 h at −75° C. and then, hydrolyzed with water and with a 1M HCl solution to acidify. The layers were separated. The aqueous layer was extracted with DCM (3×10 mL). The combined organics were washed with brine, dried over MgSO$_4$, filtered and solvents were removed in vacuo. The crude residue was purified by silica gel flash chromatography (cyclohexane/AcOEt 93:7 to 90:10) to afford the desired product in 76% yield (176 mg) as an uncoloured oil. $^1$H NMR (300 MHz, CDCl$_3$) δ 7.76 (d, J=2.2 Hz, 1H), 7.65 (d, J=8.3 Hz, 1H), 7.41-7.27 (m, 6H), 5.81 (s, 1H), 2.36 (s, OH); $^{13}$C NMR (75 MHz, CDCl$_3$) δ 143.5 (C), 142.8 (C), 135.1 (d, J=2.0 Hz, CH), 131.0 (CH), 130.2 (q, J=31.3 Hz, C), 129.0 (CH), 128.5 (CH), 126.7 (CH), 125.9 (q, J=5.4 Hz, CH), 123.0 (q, J=273.6 Hz, C), 118.9 (q, J=2.0 Hz, C), 75.4 (CH); MS (ESI) m/z: 313.0, 315.0 [M-OH, $^{79}$Br, $^{81}$Br]$^+$; 348.0, 350.0 [M+NH$_4$, $^{79}$Br, $^{81}$Br]$^+$; 680.0 [2M+NH$_4$, $^{79}$Br, $^{81}$Br]$^+$.

4-benzyl-1-bromo-2-(trifluoromethyl)benzene

To a solution of (4-bromo-3-(trifluoromethyl)phenyl)(phenyl)methanol (168 mg, 0.507 mmol) in 0.34 mL of anhydrous DCM (C=1.5M), were successively added dropwise trifluoroacetic acid (195 μL, 5 eq) and triethylsilane (243 μL, 3 eq). After 1 h45 of stirring at r.t., the reaction mixture was hydrolyzed with a saturated NH₄Cl solution (5 mL). The layers were diluted with 20 mL of DCM and 20 mL of water and then separated. The aqueous layer was extracted with DCM (3×10 mL) The combined organic phase was washed with a saturated NaHCO₃ solution (20 mL), brine (20 mL), dried over MgSO₄, filtered and concentrated in vacuo. The crude residue was purified by silica gel flash chromatography (cyclohexane) to afford the desired product in 84% yield (135 mg) as uncoloured oil. $^1$H NMR (300 MHz, CDCl₃) δ 7.62 (d, J=8.2 Hz, 1H), 7.54 (d, J=2.0 Hz, 1H), 7.34 (tt, J=7.9, 1.8 Hz, 2H), 7.26 (t, J=7.3 Hz, 1H), 7.22-7.15 (m, 3H), 4.00 (s, 2H); $^{13}$C NMR (75 MHz, CDCl₃) δ 141.0 (C), 139.5 (C), 135.1 (CH), 133.6 (CH), 130.2 (q, J=31.3 Hz, C), 129.0 (CH), 128.9 (CH), 128.4 (q, J=5.4 Hz, CH), 126.8 (CH), 123.1 (q, J=273.4 Hz, C), 117.5 (q, J=1.9 Hz, C), 41.3 (CH₂).

2-(4-benzyl-2-(trifluoromethyl)phenyl)-4,4,5,5-tetramethyl-1,3,2-dioxaborolane

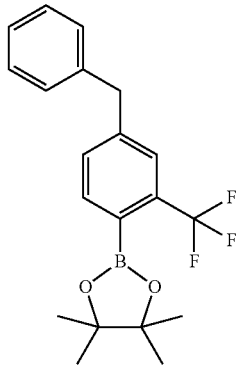 [SMILES: CC1(C)OB(c2ccc(Cc3ccccc3)cc2C(F)(F)F)OC1(C)C]

In a Schlenk tube with a stirring bar, 4-benzyl-1-bromo-2-(trifluoromethyl)benzene (135 mg, 0.428 mmol), potassium acetate AcOK (126 mg, 3 eq), bis(pinacolato)diboron (141 mg, 1.3 eq), and PdCl₂(dppf) (31 mg, 0.1 eq) were placed. The tube was evacuated and back-filled with nitrogen (this was repeated three additional times). Then, 6.1 mL of degassed 1,4-dioxane (C=0.07M) was introduced. The reaction mixture was allowed to stir at 100° C. for 14 h30. After cooling to r.t. and diluting with AcOEt, the mixture was filtered through a Celite® pad. The solvents were removed in vacuo. The crude product was purified by silica gel flash chromatography (PE/DCM 100:0 to 80:20) to afford the desired compound in 68% yield (105.5 mg) as uncolored oil. $^1$H NMR (300 MHz, CDCl₃) δ 7.68 (d, J=7.6 Hz, 1H), 7.52 (s, 1H), 7.35 (d, J=7.6 Hz, 1H), 7.33-7.27 (m, 2H), 7.23 (t, J=7.2 Hz, 1H), 7.15 (d, J=8.2 Hz, 2H), 4.04 (s, 2H), 1.38 (s, 12H); $^{13}$C NMR (75 MHz, CDCl₃) δ 143.5 (C), 140.1 (C), 135.3 (CH), 134.2 (d, J=31.2 Hz, C), 131.4 (CH), 129.0 (CH), 128.7 (CH), 126.5 (CH), 126.0 (q, J=4.7 Hz, CH), 124.5 (q, J=273.5 Hz, C), 84.5 (2C), 41.8 (CH₂), 24.7 (4CH₃); MS (ESI) m/z: 393.1 [M−H+MeOH]−; 420.9 [M−H+HCOOH]−.

Example 56

4-(4-benzyl-3,5-dimethoxyphenyl)-6-(4-(4-methylpiperazin-1-yl)phenyl)-9H-pyrido[2,3-b]indole (R696)

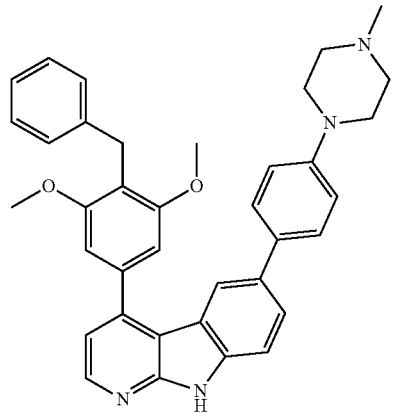 [SMILES: COc1cc(-c2ccnc3[nH]c4ccc(-c5ccc(N6CCN(C)CC6)cc5)cc4c23)cc(OC)c1Cc1ccccc1]

The crude product was purified by silica gel flash chromatography (DCM/MeOH 95:5) to afford the desired product in 82% yield as a yellowish solid. $^1$H NMR (300 MHz, CDCl₃) δ 11.59 (s, 1H), 8.53 (d, J=5.1 Hz, 1H), 8.07 (d, J=1.4 Hz, 1H), 7.71 (dd, J=8.5, 1.7 Hz, 1H), 7.60 (d, J=8.5 Hz, 1H), 7.41 (d, J=8.7 Hz, 2H), 7.36 (d, J=7.3 Hz, 2H), 7.26 (t, J=7.4 Hz, 2H), 7.18 (t, J=7.2 Hz, 1H), 7.13 (d, J=5.1 Hz, 1H), 6.97-6.89 (m, 4H), 4.17 (s, 2H), 3.80 (s, 6H), 3.36-3.22 (m, 4H), 2.74-2.61 (m, 4H), 2.43 (s, 3H); $^{13}$C NMR (75 MHz, CDCl₃) δ 158.5 (2C), 153.2 (C), 149.9 (C), 146.2 (C), 145.1 (CH), 141.7 (C), 138.2 (C), 138.1 (C), 132.8 (C), 132.5 (C), 128.7 (CH), 128.2 (CH), 127.3 (CH), 125.6 (CH), 125.5 (CH), 121.3 (C), 120.5 (CH), 118.0 (C), 116.4 (CH), 116.2 (CH), 114.1 (C), 111.5 (CH), 104.5 (CH), 56.0 (2OCH₃), 55.1 (NCH₂), 48.9 (NCH₂), 46.1 (NCH₃), 28.9 (CH₂); MS (ESI) m/z: 569.3 [M+H]⁺; 1137.7 [2M+H]⁺.

The boronic pinacolic ester 2-(4-benzyl-3,5-dimethoxyphenyl)-4,4,5,5-tetramethyl-1,3,2-dioxaborolane used in this synthesis was obtained as follows:

(4-bromo-2,6-dimethoxyphenyl)(phenyl)methanone

To a cooled suspension of AlCl₃ (150 mg, 1.2 eq) in 2 mL of anhydrous DCM at 0° C., was added dropwise benzoyl chloride (120 μL, 1.1 eq). Once the mixture was become limpid (15 min), 1-bromo-3,5-dimethoxybenzene (208 mg, 0.958 mmol) solubilized in 1 mL of DCM was slowly added at 0° C. After 1 h15 of stirring at low temperature, the yellow reaction mixture was hydrolyzed with a saturated NH₄Cl solution (6 mL) The aqueous layer, more diluted with water and with a saturated NaHCO₃ solution, was extracted with DCM (3×12 mL) The combined extracts were washed with aq. NaHCO₃ solution (20 mL), with brine (20 mL), dried over MgSO₄ and solvents were removed in vacuo. The crude was purified by silica gel flash chromatography (cyclohexane/AcOEt 100:0 to 93:7) and allowed to isolate (2-bromo-4,6-dimethoxyphenyl)(phenyl)methanone (264 mg) and (4-bromo-2,6-dimethoxyphenyl)(phenyl)methanone (29.4 mg) in 95% chemical yield (90/10 ratio) as white solids. $^1$H NMR (300 MHz, CDCl₃) δ 7.82 (d, J=8.5 Hz, 2H), 7.56 (t, J=7.4 Hz, 1H), 7.43 (t, J=7.5 Hz, 2H), 6.79 (s, 2H), 3.70 (s, 6H); $^{13}$C NMR (75 MHz, CDCl₃) δ 194.4

(C═O), 158.1 (C), 137.4 (C), 133.6 (CH), 129.5 (2CH), 128.6 (2CH), 124.2 (C), 116.9 (C), 108.0 (2CH), 56.3 (2OCH$_3$); MS (ESI) m/z: 321.0, 322.9 [M+H, $^{79}$Br, $^{81}$Br]$^+$; 243.1, 244.9 [M-Ph, $^{79}$Br, $^{81}$Br]$^+$.

2-benzyl-5-bromo-1,3-dimethoxybenzene (4-bromo-2,6-dimethoxyphenyl)(phenyl)methanone (87 mg, 0.271 mmol) was solubilized and stirred into a mixture of trifluoroacetic acid (250 µL, 12 eq) and triethylsilane (260 µL, 6 eq) heated at 80° C. for 15 h. After cooling to r.t., 20 mL of DCM were added to the reaction mixture. The organic layer was washed with a saturated NaHCO$_3$ solution (2×20 mL), with brine, dried over MgSO$_4$, filtered and concentrated in vacuo. The crude residue was purified by silica gel flash chromatography (cyclohexane/AcOEt 95:5) to afford the reduced compound in 98% yield (81.4 mg) as a white solid. $^1$H NMR (300 MHz, CDCl3) δ 7.28-7.21 (m, 4H), 7.20-7.12 (m, 1H), 6.73 (s, 2H), 3.98 (s, 2H), 3.81 (s, 6H); $^{13}$C NMR (75 MHz, CDCl$_3$) δ 158.77 (2C), 141.23 (C), 128.57 (2CH), 128.14 (2CH), 125.63 (CH), 120.45 (C), 116.86 (C), 107.71 (2CH), 56.04 (2OCH$_3$), 28.58 (CH$_2$); MS (ESI) m/z: 307.4, 309.0 [M+H, $^{79}$Br, $^{81}$Br]$^+$; 324.1, 326.1 [M+NH$_4$, $^{79}$Br, $^{81}$Br]$^+$.

2-(4-benzyl-3,5-dimethoxyphenyl)-4,4,5,5-tetramethyl-1,3,2-dioxaborolane

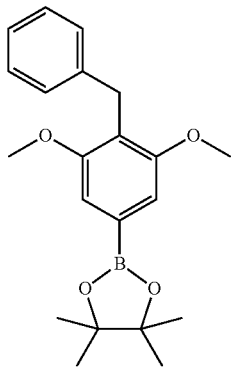 [SMILES: COc1cc(B2OC(C)(C)C(C)(C)O2)cc(OC)c1Cc1ccccc1]

In a Schlenk tube with a stirring bar, 2-benzyl-5-bromo-1,3-dimethoxybenzene (81.6 mg, 0.266 mmol), potassium acetate AcOK (78 mg, 3 eq), bis(pinacolato)diboron (88 mg, 1.3 eq), and PdCl$_2$(dppf) (19.5 mg, 0.1 eq) were placed. The tube was evacuated and back-filled with nitrogen (this was repeated three additional times). Then, 3.8 mL of degassed 1,4-dioxane (C=0.07M) was introduced. The reaction mixture was allowed to stir at 100° C. for 14 h30. After cooling to r.t. and diluting with AcOEt (10 mL), the mixture was filtered through a Celite® pad. The solvents were removed in vacuo. The crude product was purified by silica gel flash chromatography (PE/AcOEt 100:0 to 93:7) to afford the desired compound in 82% yield (76.9 mg) as white solid. $^1$H NMR (300 MHz, CDCl$_3$) δ 7.29-7.18 (m, 4H), 7.19-7.07 (m, 1H), 7.05 (s, 2H), 4.08 (s, 2H), 3.88 (s, 6H), 1.38 (s, 12H); $^{13}$C NMR (75 MHz, CDCl$_3$) δ 157.9 (2C), 141.6 (C), 128.7 (2CH), 128.0 (2CH), 125.4 (CH), 121.3 (C), 109.8 (2CH), 83.9 (2C), 56.0 (2OCH$_3$), 29.0 (CH$_2$), 25.0 (4CH$_3$); MS (ESI) m/z: 355.3 [M+H]$^+$; 372.5 [M+NH$_4$]$^+$; 726.5 [2M+NH$_4$]$^+$.

Example 57

(2,5-dimethoxy-4-(6-(4-(4-methylpiperazin-1-yl)phenyl)-9H-pyrido[2,3-b]indol-4-yl)phenyl)(phenyl)methanol (R655)

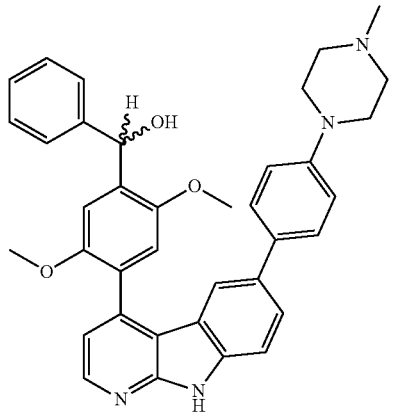

To a solution of (2,5-dimethoxy-4-(6-(4-(4-methylpiperazin-1-yl)phenyl)-9H-pyrido[2,3-b]indol-4-yl)phenyl)(phenyl)methanone (example 50, 39.8 mg, 0.0683 mmol) in CH$_2$Cl$_2$/MeOH 5:2 (2 mL), NaBH$_4$ (6 mg, 2.3 eq) was added. After stirring for 1 h20 at r.t., the reaction mixture was quenched with sat. aq. NH$_4$Cl (5 mL), diluted with CH$_2$Cl$_2$ (25 mL) and washed with water (30 mL) The organic layer was collected and the aqueous layer washed four times with CH$_2$Cl$_2$ (20 mL) The combined organic layers were washed with brine and dried over MgSO$_4$, filtered and evaporated to dryness. A white solid was obtained in 66% yield (26.3 mg) after trituration of the crude product in DCM and filtration. $^1$H NMR (300 MHz, DMSO, 80° C.) δ 11.61 (s, 1H), 8.41 (d, J=5.0 Hz, 1H), 7.63 (dd, J=8.4, 1.9 Hz, 1H), 7.51 (d, J=8.4 Hz, 1H), 7.49-7.41 (m, 4H), 7.35-7.15 (m, 5H), 7.08 (d, J=5.0 Hz, 1H), 7.02 (s, 1H), 6.98-6.79 (m, 2H), 6.11 (d, J=4.9 Hz, 1H), 5.67 (d, J=5.4 Hz, 1H), 3.69 (s, 3H), 3.62 (s, 3H), 3.24-3.14 (m, 4H), 2.54-2.47 (m, 4H), 2.27 (s, 3H); $^{13}$C NMR (75 MHz, DMSO, 80° C.) δ 152.2 (C), 150.2 (C), 149.6 (C), 149.2 (C), 145.2 (CH), 144.8 (C), 140.6 (C), 137.6 (C), 135.1 (C), 131.0 (C), 131.0 (C), 127.5 (CH), 126.3 (CH), 126.2 (CH), 126.1 (CH), 125.9 (C), 124.3 (CH), 121.8 (C), 120.7 (C), 118.6 (CH), 116.1 (C), 115.3 (CH), 113.4 (CH), 111.0 (CH), 110.6 (CH), 68.1 (CH), 55.9 (OCH$_3$), 55.8 (OCH$_3$), 54.3 (2CH$_2$), 47.8 (2CH$_2$), 45.3 (NCH$_3$); MS (ESI) m/z: 585.5 [M+H]$^+$; 1170.1 [2M+H]$^+$; 567.3 [M-OH]$^+$; HRMS calcd for C$_{37}$H$_{37}$N$_4$O$_3$ [M+H]$^+$ 585.2860 found 585.2868.

Example 58

4-(4-benzylpiperidin-1-yl)-6-(4-(4-methylpiperazin-1-yl)phenyl)-9H-pyrido[2,3-b]indole (R664)

4-(4-benzylpiperidin-1-yl)-6-(4-(4-methylpiperazin-1-yl)phenyl)-9-(phenylsulfonyl)-9H-pyrido[2,3-1)]indole 9-Benzenesulfonyl-4-chloro-6-[4-(4-methyl-piperazin-1-yl)-phenyl]-9H-pyrido[2,3-b]indole (building block A) 60 mg, 0.116 mmol) and 4-benzylpiperidine (0.25 mL, 12 eq) were heated at 150° C. for 5 h30. After cooling to r.t., the reaction mixture was diluted with DCM (20 mL), washed 3 times with water (3×10 mL) and brine (10 mL). The organic layer was dried over MgSO$_4$, filtered and evaporated to dryness. The crude product was purified by silica gel flash chromatography (DCM/MeOH 98:2 to 97:3) to afford the desired product in 67% (50.8 mg) yield as an uncoloured amorphous solid. $^1$H NMR (300 MHz, CDCl$_3$) δ 8.53 (d, J=8.8 Hz, 1H), 8.38 (d, J=5.6 Hz, 1H), 8.17 (d, J=8.9 Hz, 2H), 8.06 (d, J=1.6 Hz, 1H), 7.73 (dd, J=8.7, 1.8 Hz, 1H), 7.62 (d, J=8.7 Hz, 2H), 7.52-7.46 (m, 2H), 7.40 (d, J=7.9 Hz, 2H), 7.36-7.18 (m, 4H), 7.10 (d, J=8.8 Hz, 2H), 6.80 (d, J=5.7 Hz, 1H), 3.62 (d, J=12.1 Hz, 2H), 3.39-3.31 (m, 4H), 2.78 (t, J=12.0 Hz, 2H), 2.71-2.62 (m, 6H), 2.40 (s, 3H), 1.89 (d, J=12.2 Hz, 2H), 1.79 (dt, J=10.4, 3.4 Hz, 1H), 1.64 (t, J=11.8 Hz, 2H); $^{13}$C NMR (75 MHz, CDCl$_3$) δ 155.79 (C), 152.9 (C), 150.6 (C), 147.8 (CH), 140.2 (C), 138.9 (C), 136.8 (C), 135.5 (C), 133.8 (CH), 132.3 (C), 129.2 (CH), 128.9 (CH), 128.4 (CH), 128.0 (CH), 127.6 (CH), 126.2 (CH), 125.6 (CH), 123.4 (C), 120.7 (CH), 116.3 (CH), 114.6 (CH), 110.3 (C), 108.5 (CH), 55.2 (2CH$_2$), 51.2 (2CH$_2$), 49.0 (2CH$_2$), 46.2 (NCH$_3$), 43.2 (CH$_2$Bn), 37.7 (CH), 32.2 (CH$_2$); MS (ESI) m/z: 656.5 [M+H]$^+$; 1312.3 [2M+H]$^+$; 515.2 [M-SO$_2$Ph+H]$^+$.

4-(4-benzylpiperidin-1-yl)-6-(4-(4-methylpiperazin-1-yl)phenyl)-9H-pyrido[2,3-b]indole

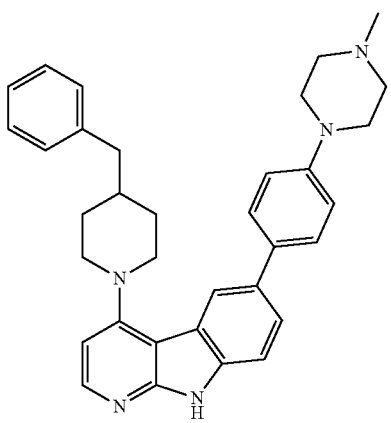 [SMILES: CN1CCN(c2ccc(-c3ccc4[nH]c5nccc(N6CCC(Cc7ccccc7)CC6)c5c4c3)cc2)CC1]

Following deprotection of 4-(4-benzylpiperidin-1-yl)-6-(4-(4-methylpiperazin-1-yl)phenyl)-9-(phenylsulfonyl)-9H-pyrido[2,3-b]indole under typical procedure A, a white solid was obtained in 60% yield after trituration of the crude product in MeOH and filtration. $^1$H NMR (300 MHz, CDCl$_3$) δ 10.21 (s, 1H), 8.33 (d, J=5.6 Hz, 1H), 8.11 (d, J=1.6 Hz, 1H), 7.67 (dd, J=8.4, 1.6 Hz, 1H), 7.63 (d, J=8.7 Hz, 2H), 7.54 (d, J=8.4 Hz, 1H), 7.37-7.29 (m, 2H), 7.28-7.19 (m, 3H), 7.09 (d, J=8.8 Hz, 2H), 6.71 (d, J=5.7 Hz, 1H), 3.85 (d, J=12.1 Hz, 2H), 3.41-3.24 (m, 4H), 2.85 (t, J=11.6 Hz, 2H), 2.71 (d, J=6.5 Hz, 2H), 2.69-2.62 (m, 4H), 2.40 (s, 3H), 1.92 (d, J=12.7 Hz, 2H), 1.87-1.78 (m, 1H), 1.77-1.64 (m, 2H); $^{13}$C NMR (75 MHz, CDCl$_3$) δ 155.9 (C), 154.2 (C), 150.1 (C), 147.0 (CH), 140.5 (C), 136.6 (C), 133.8 (C), 133.3 (C), 129.3 (CH), 128.4 (CH), 128.0 (CH), 126.2 (CH), 124.5 (CH), 121.5 (C), 121.1 (CH), 116.6 (CH), 110.9 (CH), 107.6 (C), 104.8 (CH), 55.3 (2CH$_2$), 51.0 (2CH$_2$), 49.2 (2CH$_2$), 46.3 (NCH$_3$), 43.3 (CH$_2$Bn), 38.1 (CH), 32.4 (2CH$_2$); MS (ESI) m/z: 516.3 [M+H]$^+$; 1031.8 [2M+H]$^+$; HRMS calcd for C$_{34}$H$_{38}$N$_5$ [M+H]$^+$ 516.3121 found 516.3124.

Example 59

4-(4-benzylpiperazin-1-yl)-6-(4-(4-methylpiperazin-1-yl)phenyl)-9H-pyrido[2,3-b]indole (R665)

4-(4-benzylpiperazin-1-yl)-6-(4-(4-methylpiperazin-1-yl)phenyl)-9-(phenylsulfonyl)-9H-pyrido[2,3-b]indole 9-Benzenesulfonyl-4-chloro-6-[4-(4-methyl-piperazin-1-yl)-phenyl]-9H-pyrido[2,3-b]indole (building block A, 50 mg, 0.0967 mmol) and benzylpiperazine (0.21 mL, 12.5 eq) were heated at 150° C. for 7 h. After cooling to r.t., the reaction mixture was diluted with DCM (20 mL), washed 3 times with water (3×10 mL) and brine (10 mL). The organic layer was dried over MgSO$_4$, filtered and evaporated to dryness. The crude product was purified by silica gel flash chromatography (DCM/MeOH 100:0 to 98:2) to afford the desired product in 57% yield (36.1 mg) as an uncoloured amorphous solid. $^1$H NMR (300 MHz, CDCl$_3$) δ 8.52 (d, J=8.7 Hz, 1H), 8.40 (d, J=5.6 Hz, 1H), 8.16 (d, J=8.8 Hz, 2H), 8.07 (d, J=1.9 Hz, 1H), 7.71 (dd, J=8.8, 1.9 Hz, 1H), 7.58 (d, J=8.7 Hz, 2H), 7.49 (t, J=7.4 Hz, 1H), 7.40 (d, J=8.0 Hz, 2H), 7.38-7.27 (m, 5H), 7.07 (d, J=8.8 Hz, 2H), 6.82 (d, J=5.6 Hz, 1H), 3.64 (s, 2H), 3.36-3.31 (m, 4H), 3.30-3.18 (m, 4H), 2.88-2.68 (m, 4H), 2.68-2.60 (m, 4H), 2.40 (s, 3H); $^{13}$C NMR (75 MHz, CDCl$_3$) δ 155.3 (C), 152.9 (C), 150.6 (C), 147.9 (CH), 138.9 (C), 137.8 (C), 136.8 (C), 135.6 (C), 133.8 (CH), 132.2 (C), 129.2 (CH), 128.9 (CH), 128.5 (CH), 127.9 (CH), 127.7 (CH), 127.4 (CH), 125.8 (CH), 123.1 (C), 120.7 (CH), 116.3 (CH), 114.7 (CH), 110.4 (C), 108.5 (CH), 63.1 (CH$_2$), 55.2 (2CH$_2$), 53.0 (2CH$_2$), 50.6 (2CH$_2$), 49.0 (2CH$_2$), 46.3 (NCH$_3$); MS (ESI) m/z: 657.3 [M+H]$^+$; 1314.7 [2M+H]$^+$; 516.5 [M-SO$_2$Ph+H]'.

4-(4-benzylpiperazin-1-yl)-6-(4-(4-methylpiperazin-1-yl)phenyl)-9H-pyrido[2,3-b]indole

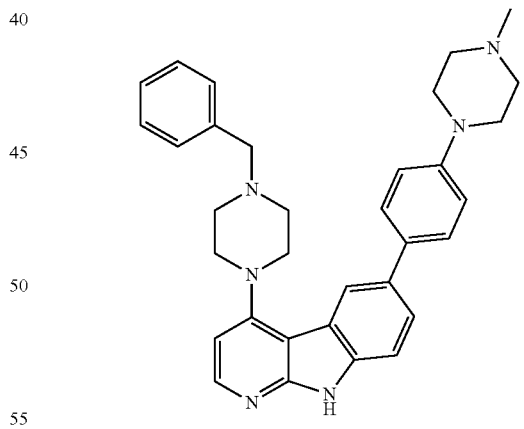

Following deprotection of 4-(4-benzylpiperazin-1-yl)-6-(4-(4-methylpiperazin-1-yl)phenyl)-9-(phenylsulfonyl)-9H-pyrido[2,3-b]indole under typical procedure A, the crude product was purified by silica gel flash chromatography (DCM/MeOH 94:6) to afford the desired product in 42% yield as a white solid. $^1$H NMR (300 MHz, CDCl$_3$) δ 10.59 (s, 1H), 8.36 (br s, 1H), 8.12 (d, J=1.7 Hz, 1H), 7.66 (dd, J=8.4, 1.7 Hz, 1H), 7.61 (d, J=8.7 Hz, 2H), 7.55 (d, J=8.4 Hz, 1H), 7.44-7.27 (m, 5H), 7.08 (d, J=8.8 Hz, 2H), 6.74 (d, J=5.4 Hz, 1H), 3.68 (s, 2H), 3.42 (br s, 4H), 3.36-3.26 (m, 4H), 2.83 (br s, 4H), 2.69-2.60 (m, 4H), 2.40 (s, 3H); $^{13}$C NMR (75 MHz, CDCl$_3$) δ 155.5 (C), 154.4 (C), 150.2 (C), 146.9 (CH), 138.1 (C), 136.9 (C), 133.8 (C), 133.3 (C), 129.4 (CH), 128.6 (CH), 128.0 (CH), 127.5 (CH), 124.7 (CH), 121.2 (C), 121.2 (CH), 116.6 (CH), 111.2 (CH), 107.8 (C), 104.7 (CH), 63.3 (CH$_2$), 55.4 (2CH$_2$), 53.3 (2CH$_2$), 50.5 (2CH$_2$), 49.3 (2CH$_2$), 46.4 (NCH$_3$); MS (ESI) m/z: 517.5 [M+H]$^+$; 1033.8 [2M+H]$^+$; HRMS calcd for C$_{33}$H$_{37}$N$_6$ [M+H]$^+$ 517.3074 found 517.3054.

Unless stated otherwise, all boronic pinacolic esters used in the above examples 1 to 59 were either commercially available or obtained via procedures known to the skilled man in the art.

Examples 1 to 59 represent individual embodiments of this invention.

Biological Activity

Biochemical and Cellular Assays

Compounds of the invention that have been tested in the above described ELISA-based in vitro kinase assay and in the Tritiated thymidine uptake cell proliferation in BAF3 cells assay and in the are tabulated in the table below.

| Example number | ELISA ALK WT IC50 (μM) | ELISA ALK L1196M IC50 (μM) | BaF3 Parental IC50 (μM) | BaF3 NPM/ALK WT IC50 (μM) | BaF3 NPM/ALK L1196M IC50 (μM) | Selectivity Index (WT) | Selectivity Index (1196M) |
|---|---|---|---|---|---|---|---|
| 1 | 2.1 | 1 | 1.4 | 0.55 | 0.94 | 3 | 1 |
| 2 | 0.5 | N/A | 0.8 | 1.1 | 0.86 | 1 | 1 |
| 3 | 7.6 | 6.4 | 2.4 | 1 | 0.51 | 2 | 5 |
| 4 | 0.35 | 0.35 | N/A | N/A | N/A | N/A | N/A |
| 5 | 0.66 | 0.68 | >25 | 2.8 | 2.6 | >9 | >10 |
| 6 | 0.25 | 0.32 | 9.5 | 2.7 | 1.8 | 4 | 5 |
| 7 | 1.2 | 0.17 | 4.1 | 0.59 | 1.6 | 7 | 3 |
| 8 | 2.2 | 0.9 | 5 | 0.69 | 0.9 | 7 | 6 |
| 9 | 1.7 | 0.35 | 25 | 43 | 2.5 | 1 | 10 |
| 10 | 0.32 | 0.11 | 2.1 | 1.1 | 1.4 | 2 | 2 |
| 11 | 0.26 | 0.16 | 1.7 | 1.5 | 0.88 | 1 | 2 |
| 12 | 0.11 | 0.052 | >50 | 50 | 17 | 1 | >3 |
| 13 | 0.37 | 0.091 | 7.6 | 4 | 5 | 2 | 2 |
| 14 | 0.28 | 0.12 | >25 | >25 | 21 | 1 | 1 |
| 15 | 0.97 | 0.39 | 6.3 | 4.1 | 3.1 | 2 | 2 |
| 16 | 0.20 | 0.04 | 8.7 | 1.5 | 0.9 | 6 | 10 |
| 17 | 0.21 | 0.14 | 2.7 | 1.8 | 1.9 | 2 | 1 |
| 18 | 0.46 | 0.15 | 5.1 | 1.9 | 1.6 | 3 | 3 |
| 19 | 0.88 | 0.32 | 2 | 1.1 | 0.67 | 2 | 3 |
| 20 | 10 | 0.90 | 3.6 | 0.52 | 0.045 | 7 | 80 |
| 21 | 1.5 | 0.7 | 3.7 | 2.2 | 0.46 | 2 | 8 |
| 22 | 2.9 | 0.88 | 3.9 | 3 | 0.59 | 1 | 7 |
| 23 | 0.61 | 0.15 | 2.3 | 1.1 | 0.36 | 2 | 6 |
| 24 | 0.052 | 0.052 | 18 | 6.1 | 1.7 | 3 | 11 |
| 25 | 1.2 | 1.6 | 7.5 | 1.8 | 0.91 | 4 | 8 |
| 26 | 0.52 | 0.59 | 0.63 | 0.61 | 0.21 | 1 | 3 |
| 27 | 1.5 | 1.8 | 2.4 | 1.1 | 0.27 | 2 | 9 |
| 28 | 0.27 | 0.16 | 0.8 | 0.72 | 0.7 | 1 | 1 |
| 29 | 0.16 | 0.28 | 0.68 | 0.42 | 0.78 | 2 | 1 |
| 30 | 1.4 | 1.5 | 0.22 | 0.099 | 0.089 | 2 | 2 |
| 31 | 1.0 | 2.3 | 0.93 | 0.48 | 0.079 | 2 | 12 |
| 32 | 3.2 | 7.1 | 6.9 | 2.5 | 2.3 | 3 | 3 |
| 33 | 1.4 | 0.23 | 1 | 0.37 | 0.47 | 3 | 2 |
| 34 | 0.56 | 0.18 | 0.86 | 0.49 | 0.29 | 2 | 3 |
| 35 | 3.3 | 1.9 | 0.48 | 0.080 | 0.088 | 6 | 5 |
| 36 | 8.5 | 0.89 | 7.1 | 6 | 0.7 | 1 | 10 |
| 37 | 0.17 | 0.13 | 4.4 | 3.7 | 2.7 | 1 | 2 |
| 38 | 0.75 | 0.29 | 1.5 | 0.65 | 0.76 | 2 | 2 |
| 39 | 1.1 | 0.27 | 1.2 | 0.51 | 0.26 | 2 | 5 |
| 40 | 0.89 | 0.13 | 0.92 | 0.41 | 0.46 | 2 | 2 |
| 41 | 1.1 | 0.14 | 2.5 | 1.2 | 1.1 | 2 | 2 |
| 42 | 1.2 | 0.29 | 2.1 | 0.91 | 0.74 | 2 | 3 |
| 43 | 4.9 | 6.2 | 3.4 | 1.9 | 3.2 | 2 | 1 |
| 44 | 29 | 43 | 0.35 | 0.17 | 0.15 | 2 | 2 |
| 45 | 3.8 | 0.91 | 2.1 | 1.1 | 0.72 | 2 | 3 |
| 46 | 5.7 | 10 | N/A | N/A | N/A | N/A | N/A |
| 47 | 6.8 | 2.2 | N/A | N/A | N/A | N/A | N/A |
| 48 | 0.84 | 7.2 | 2.1 | 1.8 | 1.2 | 1 | 2 |
| 49 | 1.8 | 0.92 | 3.2 | 3.2 | 0.58 | 1 | 6 |
| 50 | 8.2 | 2.3 | 1.1 | 0.59 | 0.34 | 2 | 3 |
| 51 | 2.8 | 0.83 | 0.72 | 0.24 | 0.14 | 3 | 5 |
| 52 | 0.31 | 0.022 | 0.81 | 0.82 | 0.47 | 1 | 2 |
| 53 | 4.3 | 1.3 | 1.8 | 1.4 | 0.64 | 1 | 3 |
| 54 | 2.2 | 2.1 | 2.2 | 1.8 | 1.7 | 1 | 1 |
| 55 | 7.9 | 3.2 | 5.1 | 5.0 | 3.1 | 1 | 2 |
| 56 | 7.9 | 19 | 2.2 | 2.2 | 1.0 | 1 | 2 |
| 57 | 18 | 8.7 | 0.79 | 0.37 | 0.21 | 2 | 4 |
| 58 | 0.20 | 0.032 | 3.3 | 1.2 | 0.60 | 3 | 6 |
| 59 | 1 | 0.69 | 0.83 | 0.84 | 0.78 | 1 | 1 |

In vivo Activity

The in vivo studies were approved by the Italian Ministry of Research and by the University internal ethical committee, and were run according to guidelines to reduce animal pain. Ten million NPM/ALK+ Karpas299 cells were injected subcutaneously in the right flank of SCID mice. Ten days later, when the tumors reached the size of 100 mm3 on average, mice were randomized either to control arm, receiving vehicle only (0.5% carboxymethylcellulose and 0.1% Tween80), or to treatment arm, receiving compound R533 by oral gavage, 150 mg/kg twice per day. Tumor size was measured bi-weekly by a caliper. General toxicity was assessed by monitoring weight loss, and by visual inspection for any sign of stress or suffering, including eye closure or bulging, ruffled/dull fur, reduced mobility, drowsiness, diarrhea. The results of the study are set out in FIGURE, and show remarkable effect.

The invention claimed is:
1. Compounds of formula (I)

wherein:
R1 is H or C1-C3 alkyl
R2 is either halogen or

X is either CH or N
R3 is either $C_1$-$C_3$ alkyl or (1-methylpiperidin-4-yl)
Rx and Ry are either H or nitro
Rz and Rz' are H, OH, or oxo
Rt and R't can be the same or different and are H or $C_1$-$C_3$ alkoxy
Ra is H or F
Rb is H, C1-C3 alkoxy, trifluoromethyl, or halogen
Re is H or halogen
Rf is H, C1-C3 alkyl or trifluoromethyl
Rg is H or F
Rk is H, halogen, trifluoromethyl, C1-C3 alkoxy, C1-C3 alkylsulfonamino
Rl is H or F
Rm is H, C1-C3 alkoxy, F or trifluoromethyl
Rn is H, C1-C3 alkyl or a 5- to 6 -membered aromatic or heteroaromatic ring
Rp is either C1-C3 alkyl or 5- to 6 -membered aromatic or heteroaromatic ring
Rq is either H or tri($C_1$-$C_4$)alkylsilyl
Rs is tri($C_1$-$C_4$)alkylsilyl Rh is either H, C1-C3 alkoxy or C1-C3 alkylcarbonylamino
Ru is either H or F
Rv is a C1-C3 alkyl
Rw and Rw' can be the same or different and are hydroxyl or C1-C3 alkoxy
L and L' are O, S, SO or $SO_2$;
Z is either C or N
and pharmaceutically acceptable salts thereof.

2. The compounds of claim 1 wherein
R1 is H or methyl
R2 is as defined in claim 1
X is either CH or N
R3 is either methyl or 1-methylpiperidin-4-yl
Rx and Ry are either H or nitro
Rz is H, OH or oxo
Rz' is H
Rt and R't can be the same or different and can be H or methoxy
Ra is H or F
Rb is H, methoxy, trifluoromethyl, F or Cl
Re is H or Cl
Rf is H, methyl or trifluoromethyl
Rg is H or F
Rk is H, Cl, F, trifluoromethyl, methoxy, methylsulfonamino
Rl is H or F
Rm is H, methoxy, F or trifluoromethyl
Rn is H, methyl, ethyl or phenyl
Rp is ethyl or phenyl
Rq is either H or triisopropylsilyl
Rs is triisopropylsilyl
Ru is F
Rv is methyl
Rw and Rw' are either hydroxyl and methoxy, respectively or both are methoxy
Z is either C or N
L is O and Rh is H
L' is S and Rh is methoxy.

3. The compounds of claim 1 wherein:
R1 is H
R2 is

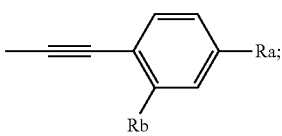

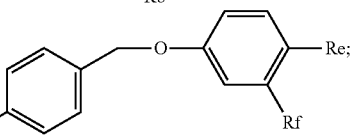

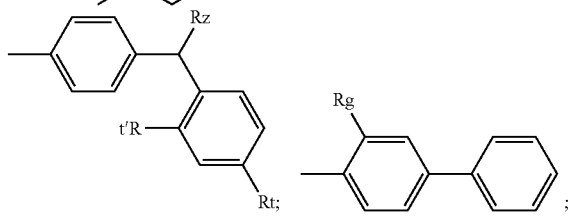

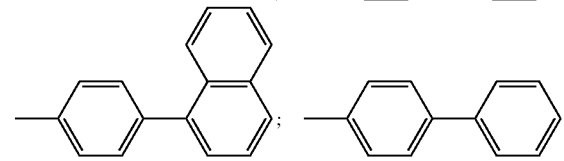

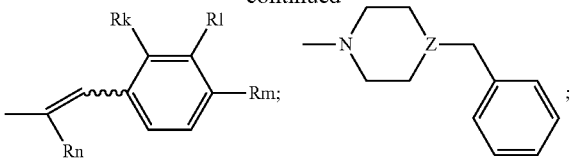

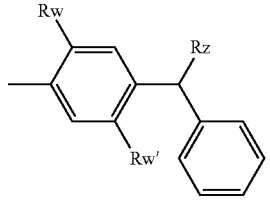

X is CH
and wherein R3, Ra, Rb, Re, Rf, Rg, Rk, Rl, Rm, Rn, Rz, Rt, R't, Rp, Z, Rw and Rw' are as defined in claim 1.

4. The compounds of claim 1 wherein R1, R2, R3, X, L, L', Z, Rx, Ry, Ra, Rb, Re, Rf, Rg, Rh, Rk, Rl, Rm, Rp, Rq, Rs, Rz, Rz', Rt, R't, Ru, Rv, Rw and Rw' are as defined in any one of claims 1-3 and wherein when R2 is

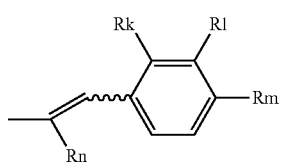

then two of Rk, Rl and Rm are H while the third is as defined in claim 1.

5. The compounds of claim 3 wherein R2 is selected from the list of

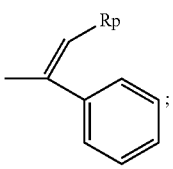 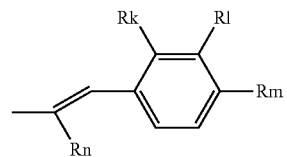

and Rk, Rl, Rm, Rn and Rp are defined in claim 3.

6. The compounds of claim 1 wherein R3 is methyl and wherein R1, R2, X, L, L', Z, Rx, Ry, Ra, Rb, Re, Rf, Rg, Rh, Rk, Rl, Rm, Rn, Rp, Rq, Rs, Rz, Rz' Rt, R't, Ru, Rv, Rw and Rw' are as defined in claim 1.

7. The compounds of claim 1 wherein R3 is (1-methylpiperidin-4-yl), R1, R2, X, L, L', Z, Rx, Ry, Ra, Rb, Re, Rf, Rg, Rh, Rk, Rl, Rm, Rn, Rp, Rq, Rs, Rz, Rz' Rt, R't, Ru, Rv, Rw and Rw' are as defined in claim 1.

8. The compounds of claim 1, selected from the list of:
(E)-6-[4-(4-Methylpiperazin-1-yl)phenyl]-4-(2-phenylvinyl)-9H-pyrido[2,3-b]indole;
(E)-6-[6-(4-Methylpiperazin-1-yl)-pyridin-3-yl]-4-(2-phenylvinyl)-9H-pyrido[2,3-b]indole;
4-Biphenyl-4-yl-6-[4-(4-methylpiperazin-1-yl)phenyl]-9H-pyrido[2,3-b]indole;
(E)-4-[2-(3-Fluorophenyl)vinyl]-6-[4-(4-methylpiperazin-1-yl)phenyl]-9H-pyrido[2,3-b]indole;
(E)-4-[2-(4-Methoxyphenyl)vinyl]-6-[4-(4-methylpiperazin-1-yl)phenyl]-9H-pyrido[2,3-b]indole;

4-(4-Benzyloxyphenyl)-6-[4-(4-methylpiperazin-1-yl)
phenyl]-9H-pyrido[2,3-b]indole;
6-[4-(4-Methylpiperazin-1-yl)phenyl]-4-[4-(3-(trifluoromethyl)phenoxymethyl)phenyl]-9H-pyrido[2,3-b]indole;
(E)-4-(2-(2-Methoxyphenyl)vinyl))-6-(4-(4-methylpiperazin-1-yl)phenyl)-9H-pyrido[2,3-b]indole;
(E)-6-(4-(4-Methylpiperazin-1-yl)phenyl)-4-(2-(2-(trifluoromethyl)phenyl)vinyl)-9H-pyrido[2,3-b]indole;
4-[4-(4-Chloro-3-methyl-phenoxymethyl)phenyl]-6-[4-(4-methylpiperazin-1-yl)phenyl]-9H-pyrido[2,3-b]indole;
6-[4-(4-Methylpiperazin-1-yl)phenyl]-4-phenylethynyl-9H-pyrido[2,3-b]indole;
(E)-4-(2-(4-Fluorophenyl)vinyl))-6-(4-(4-methylpiperazin-1-yl)phenyl)-9H-pyrido[2,3-b]indole;
(E)-6-(4-(4-Methylpiperazin-1-yl)phenyl)-4-(2-(4-(trifluoromethyl)phenyl)vinyl))-9H-pyrido[2,3-b]indole;
4-(3-Fluorobiphenyl-4-yl)-6-[4-(4-methylpiperazin-1-yl)phenyl]-9H-pyrido[2,3-b]indole;
4-(4-Benzylphenyl)-6-[4-(4-methylpiperazin-1-yl)phenyl]-9H-pyrido[2,3-b]indole;
4-Biphenyl-3-yl-6-[4-(4-methylpiperazin-1-yl)phenyl]-9H-pyrido[2,3-b]indole;
4-((2-Methoxyphenyl)ethynyl)-6-[4-(4-methylpiperazin-1-yl)phenyl]-9H-pyrido[2,3-b]indole;
6-[4-(4-Methylpiperazin-1-yl)phenyl]-4-((2-(trifluoromethyl)phenyl)ethynyl)-9H-pyrido[2,3-b]indole;
4-((4-Fluorophenyl)ethynyl)-6-[4-(4-methylpiperazin-1-yl)phenyl]-9H-pyrido[2,3-b]indole;
4-(2-Fluorophenyl)ethynyl)-6-[4-(4-methylpiperazin-1-yl)phenyl]-9H-pyrido[2,3-b]indole;
(E)-4-(2-(2-Fluorophenyl)vinyl))-6-(4-(4-methylpiperazin-1-yl)phenyl)-9H-pyrido[2,3-b]indole;
(E)-4-(2-(2-Chlorophenyl)vinyl))-6-(4-(4-methylpiperazin-1-yl)phenyl)-9H-pyrido[2,3-b]indole;
6-(4-(4-Methylpiperazin-1-yl)phenyl)-N-(3-nitrophenyl)-9H-pyrido[2,3-b]indol-4-amine;
6-(4-(4-Methylpiperazin-1-yl)phenyl))-N-(2-nitrophenyl)-9H-pyrido[2,3-b]indol-4-amine;
4-((2-Chlorophenypethynyl)-6-[4-(4-methylpiperazin-1-yl)phenyl]-9H-pyrido[2,3-b]indole;
4-((2-Methoxyphenypethynyl)-9-methyl-6-[4-(4-methylpiperazin-1-yl)phenyl]-9H-pyrido[2,3-b]indole;
4,6-Bis-[4-(4-methylpiperazin-1-yl)phenyl]-9H-pyrido[2,3-b]indole;
4-(4-Benzylphenyl)-6-(4-(4-(1-methylpiperidin-4-yl)piperazin-1-yl)phenyl)-9H-pyrido[2,3-b]indole;
(E)-6-(4-(4-(1-Methylpiperidin-4-yl)piperazin-1-yl)phenyl)-4-(2-(2-(trifluoromethyl)phenyl)vinyl))-9H-pyrido[2,3-b]indole;
6-(4-(4-(1-methylpiperidin-4-yl)piperazin-1-yl)phenyl)-N-(2-nitrophenyl)-9H-pyrido[2,3-b]indol-4-amine;
(E)-6-(4-(4-Methylpiperazin-1-yl)phenyl)-4-(1-phenylprop-1-en-2-yl)-9H-pyrido[2,3-b]indole;
(4-{6-[4-(4-Methylpiperazin-1-yl)phenyl]-9H-pyrido[2,3-b]indol-4-yl}-phenyl)phenyl-methanol;
(4-{6-[4-(4-Methylpiperazin-1-yl)phenyl]-9H-pyrido[2,3-b]indol-4-yl }-phenyl)phenyl-methanone;
4-Chloro-6-[4-(4-methylpiperazin-1-yl)phenyl]-9H-pyrido[2,3-b]indole;
(E)-N-[2-(2-{6-[4-(4-Methylpiperazin-1-yl)phenyl]-9H-pyrido[2,3-b]indol-4-yl}-vinyl)phenyl]-methanesulfonamide;
6-[4-(4-Methylpiperazin-1-yl)phenyl]-4-(4-naphthalen-1-yl-phenyl)-9H-pyrido[2,3-b]indole;
(E)-4-(1,2-Diphenylvinyl)-6-[4-(4-methylpiperazin-1-yl)phenyl]-9H-pyrido[2,3-b]indole;
(E)-6-[4-(4-Methylpiperazin-1-yl)phenyl]-4-(1-phenyl-but-1-enyl)-9H-pyrido[2,3-b]indole;
(E)-6-[4-(4-Methylpiperazin-1-yl)phenyl]-4-(1-phenyl-but-1-en-2-yl)-9H-pyrido[2,3-b]indole;
4-[4-(2,4-Dimethoxybenzyl)phenyl]-6[4-(4-methylpiperazin-1-yl)phenyl]-9H-pyrido[2,3-b]indole;
(E)-4-[1-(2-Methoxyphenyl)-prop-1-en-2-yl]-6-[4-(4-methylpiperazin-1-yl)phenyl]-9H-pyrido[2,3-b]indole;
(E)-6-[4-(4-Methylpiperazin-1-yl)-phenyl]-4-[1-(2-(trifluoromethyl)phenyl)-prop-1-en-2-yl]-9H-pyrido[2,3-b]indole;
6-(4-(4-methylpiperazin-1-yl)phenyl)-4-((triisopropylsilyl)ethynyl)-9H-pyrido[2,3-b]indole;
(E) and/or (Z)-6-(4-(4-methylpiperazin-1-yl)phenyl)-4-(2-(triisopropylsilyl)vinyl)-9H-pyrido[2,3-b]indole; and
4-ethynyl-6-(4-(4-methylpiperazin-1-yl)phenyl)-9H-pyrido[2,3-b]indole.

9. The compounds of claim 1, selected from the list of:
4-(4-Methoxy-phenylsulfanyl)-6-[4-(4-methyl-piperazin-1-yl)-phenyl]-9H-pyrido[2,3-b]indole;
4-(1-(4-methylbenzyl)-1 H-1,2,3-triazol-4-yl)-6-(4-(4-methylpiperazin-1-yl)phenyl)-9H-pyrido[2,3-b]indole;
6-(4-(4-methylpiperazin-1-yl)phenyl)-4-(4-phenoxyphenyl)-9H-pyrido[2,3-b]indole;
4-(6-(4-fluorophenyl)pyridin-3-yl)-6-(4-(4-methylpiperazin-1-yl)phenyl)-9H-pyrido[2,3-b]indole;
(2,5-dimethoxy-4-(6-(4-(4-methylpiperazin-1-yl)phenyl)-9H-pyrido[2,3-b]indol-4-yl)phenyl)(phenyl)methanone;
(2-hydroxy-5-methoxy-4-(6-(4-(4-methylpiperazin-1-yl)phenyl)-9H-pyrido[2,3-b]indol-4-yl)phenyl)(phenyl)methanone;
4-(4-benzyl-2,5-dimethoxyphenyl)-6-(4-(4-methylpiperazin-1-yl)phenyl)-9H-pyrido[2,3-b]indole;
2-benzyl-4-methoxy-5-(6-(4-(4-methylpiperazin-1-yl)phenyl)-9H-pyrido[2,3-b]indol-4-yl)phenol;
4-(4-benzyl-3-(trifluoromethyl)phenyl)-6-(4-(4-methylpiperazin-1-yl)phenyl)-9H-pyrido[2,3-b]indole;
4-(4-benzyl-2-(trifluoromethyl)phenyl)-6-(4-(4-methylpiperazin-1-yl)phenyl)-9H-pyrido[2,3-b]indole;
4-(4-benzyl-3,5-dimethoxyphenyl)-6-(4-(4-methylpiperazin-1-yl)phenyl)-9H-pyrido[2,3-b]indole;
(2,5-dimethoxy-4-(6-(4-(4-methylpiperazin-1-yl)phenyl)-9H-pyrido[2,3-b]indol-4-yl)phenyl)(phenyl)methanol;
4-(4-benzylpiperidin-1-yl)-6-(4-(4-methylpiperazin-1-yl)phenyl)-9H-pyrido[2,3-b]indole; and
4-(4-benzylpiperazin-1-yl)-6-(4-(4-methylpiperazin-1-yl)phenyl)-9H-pyrido[2,3-b]indole.

10. The compounds of claim 2, selected from the list of:
4-Biphenyl-4-yl-6-[4-(4-methylpiperazin-1-yl)phenyl]-9H-pyrido[2,3-b]indole (R510a);
(E)-4-(2-(2-Methoxyphenyl)vinyl))-6-(4-(4-methylpiperazin-1-yl)phenyl)-9H-pyrido[2,3-b]indole;
(E)-6-(4-(4-Methylpiperazin-1-yl)phenyl)-4-(2-(2-(trifluoromethyl)phenyl)vinyl)-9H-pyrido[2,3-b]indole;
4-[4-(4-Chloro-3-methylphenoxymethyl)phenyl]-6-[4-(4-methylpiperazin-1-yl)phenyl]-9H-pyrido[2,3-b]indole;
(E)-4-(2-(4-Fluorophenyl)vinyl))-6-(4-(4-methylpiperazin-1-yl)phenyl)-9H-pyrido[2,3-b]indole;
4-(4-Benzylphenyl)-6-[4-(4-methylpiperazin-1-yl)phenyl]-9H-pyrido[2,3-b]indole;

4-Biphenyl-3-yl-6-[4-(4-methylpiperazin-1-yl)phenyl]-9H-pyrido[2,3-b]indole;
4-((2-Methoxyphenyl)ethynyl)-6-[4-(4-methylpiperazin-1-yl)phenyl]-9H-pyrido[2,3-b]indole;
6-(4-(4-Methylpiperazin-1-yl)phenyl)-N-(3-nitrophenyl)-9H-pyrido[2,3-b]indol-4-amine;
(4-{6-[4-(4-Methylpiperazin-1-yl)phenyl]-9H-pyrido[2,3-b]indol-4-yl}-phenyl)phenyl-methanol;
(4-{6-[4-(4-Methylpiperazin-1-yl)phenyl]-9H-pyrido[2,3-b]indol-4-yl}-phenyl)phenyl-methanone;
6-[4-(4-Methylpiperazin-1-yl)phenyl]-4-(4-naphthalen-1-yl-phenyl)-9H-pyrido[2,3-b]indole;
4-(4-benzylpiperidin-1-yl)-6-(4-(4-methylpiperazin-1-yl)phenyl)-9H-pyrido[2,3-b]indole;
4-(4-benzylpiperazin-1-yl)-6-(4-(4-methylpiperazin-1-yl)phenyl)-9H-pyrido[2,3-b]indole; and
4-(4-benzyl-2,5-dimethoxyphenyl)-6-(4-(4-methylpiperazin-1-yl)phenyl)-9H-pyrido[2,3-b]indole.

11. A method for treating non-Hodgkin's lymphoma comprising administering to a subject in need thereof a compound according to claim 1.

12. Compounds of formula (II)

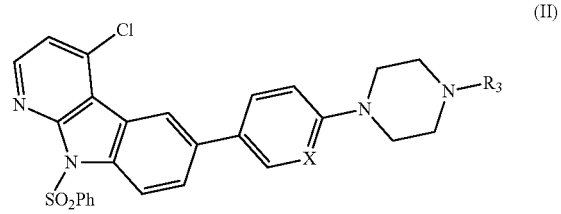

wherein R3 and X are as defined in claim 1.

13. The compounds of claim 12, selected from the list of:
9-Benzenesulfonyl-4-chloro-6-[4-(4-methylpiperazin-1-yl)-phenyl]-9H-pyrido[2,3-b]indole;
9-Benzenesulfonyl-4-chloro-6-[4-(6-methylpiperazin-1-yl)-pyridin-3-yl]-9H-pyrido[2,3-b]indole; and
9-Benzenesulfonyl-4-chloro-6-(4-(4-(1-methylpiperidin-4-yl)piperazin-1-yl)phenyl)-9H-pyrido[2,3-b]indole.

* * * * *